(12) United States Patent
Ryan

(10) Patent No.: US 8,338,100 B1
(45) Date of Patent: Dec. 25, 2012

(54) ISOLATED GENOMIC POLYNUCLEOTIDE FRAGMENTS FROM CHROMOSOME 12 THAT ENCODE HUMAN CARBOXYPEPTIDASE M

(75) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

(21) Appl. No.: 13/244,474

(22) Filed: Sep. 24, 2011

Related U.S. Application Data

(62) Division of application No. 12/795,909, filed on Jun. 8, 2010, now Pat. No. 8,058,052, which is a division of application No. 10/608,463, filed on Jun. 27, 2003, now Pat. No. 7,754,424.

(51) Int. Cl.
*C12Q 1/68* (2006.01)
*C07H 21/02* (2006.01)

(52) U.S. Cl. .................... 435/6.12; 536/23.1
(58) Field of Classification Search ............. 435/6.12; 536/23.1
See application file for complete search history.

(56) References Cited

U.S. PATENT DOCUMENTS

| | | | |
|---|---|---|---|
| 5,411,860 | A | 5/1995 | Vogelstein et al. |
| 6,184,212 | B1 | 2/2001 | Miraglia et al. |
| 7,754,424 | B1 | 7/2010 | Ryan |

OTHER PUBLICATIONS

Andersen et al., Mammalian Genome 7:780-783. 1996.
Bureau et al., Genomics 28:109-112. 1995.
Fang et al. "Comparative analysis of p73 and p53 regulation and effector functions" J. Cell Biol. 147: 823-830. 1999. (abstract, Medline accession No. 2000029768 in Examiners search result Feb. 11, 2011 of U.S. Appl. No. 12/795,864).
Muzny et al. NCBI Locus AC025423, gi:14578057, 2003.
Oliner et al., Nature 358:80-83. 1992.
Oliner et al. NCBI Locus NM-002392, gi:4505136, 1999. on Dec. 1, 2004 List of References by Examiner in related U.S. Appl. No. 10/608,463).
Rehli et al., J. Biol. Chem. 270: 15644-15649. 1995.
Ries et al., Cell 103: 321-330. 2000.
Sigalas et al., Nature Med. 9:912-917. 1996.
Tan et al., J. Biol. Chem. 264: 13165-13170. 1989.
Watson et al. "Recombinant DNA" pp. 137-138 2nd Ed. Scientific American, New York. 1992.
Zauberman et al. "A functional p53-responsive intronic promoter is contained within the human mdm2 gene" Nucleic Acids Res. 23: 2584-2592. 1995 (abstract, Medline accession No. 1995380270 in Examiners search result Feb. 11, 2011 of U.S. Appl. No. 12/795,864).
U.S. Appl. No. 10/608,463 Non-Final Office Action, Dec. 1, 2004.
U.S. Appl. No. 10/608,463 Final Office Action, May 25, 2005.
U.S. Appl. No. 10/608,463 Non-final Office Action, Mar. 8, 2006.
U.S. Appl. No. 10/608,463 Final Office Action, Aug. 25, 2006.
U.S. Appl. No. 10/608,463 Final Office Action, Apr. 16, 2007.
U.S. Appl. No. 10/608,463 Non-Final Office Action, May 14, 2008.
U.S. Appl. No. 10/608,463 Final Office Action, Jan. 2, 2009.
U.S. Appl. No. 10/608,463 Notice of Allowance, Feb. 23, 2010.
U.S. Appl. No. 10/608,463 Notice of Allowability, Feb. 23, 2010.
U.S. Appl. No. 12/795,864 Notice of Allowance, Feb. 11, 2011.
U.S. Appl. No. 12/795,864 Notice of Allowability, Feb. 11, 2011.
U.S. Appl. No. 12/795,909 Notice of Allowance, Jul. 6, 2011.
U.S. Appl. No. 12/795,909 Notice of Allowability, Jul. 6, 2011.
U.S. Appl. No. 13/116,140, Non-final Office Action dated Feb. 1, 2012.
U.S. Appl. No. 13/116,140, Notice of allowance dated Jun. 19, 2012.

*Primary Examiner* — Tekchand Saidha
(74) *Attorney, Agent, or Firm* — Cheryl H. Agris

(57) ABSTRACT

The invention is directed to isolated genomic polynucleotide fragments that encode human carboxypeptidase M and human mouse double minute 2 homolog, vectors and hosts containing these fragments and fragments hybridizing to non-coding regions as well as antisense oligonucleotides to these fragments. The invention is further directed to methods of using these fragments to obtain human carboxypeptidase M and human mouse double minute 2 homolog and to diagnose, treat, prevent and/or ameliorate a pathological disorder.

5 Claims, No Drawings

SEQUENCE LISTING

<160> NUMBER OF SEQ ID NOS: 4

<210> SEQ ID NO 1
<211> LENGTH: 443
<212> TYPE: PRT
<213> ORGANISM: Homo sapiens

<400> SEQUENCE: 1

```
Met Asp Phe Pro Cys Leu Trp Leu Gly Leu Leu Pro Leu Val Ala
1               5                   10                  15

Ala Leu Asp Phe Asn Tyr His Arg Gln Glu Gly Met Glu Ala Phe Leu
                20                  25                  30

Lys Thr Val Ala Gln Asn Tyr Ser Ser Val Thr His Leu His Ser Ile
            35                  40                  45

Gly Lys Ser Val Lys Gly Arg Asn Leu Trp Val Leu Val Gly Arg
50                  55                  60

Phe Pro Lys Glu His Arg Ile Gly Ile Pro Glu Phe Lys Tyr Val Ala
65                  70                  75                  80

Asn Met His Gly Asp Glu Thr Val Gly Arg Glu Leu Leu Leu His Leu
                85                  90                  95

Ile Asp Tyr Leu Val Thr Ser Asp Gly Lys Asp Pro Glu Ile Thr Asn
            100                 105                 110

Leu Ile Asn Ser Thr Arg Ile His Ile Met Pro Ser Met Asn Pro Asp
            115                 120                 125

Gly Phe Glu Ala Val Lys Lys Pro Asp Cys Tyr Tyr Ser Ile Gly Arg
130                 135                 140

Glu Asn Tyr Asn Gln Tyr Asp Leu Asn Arg Asn Phe Pro Asp Ala Phe
145                 150                 155                 160

Glu Tyr Asn Asn Val Ser Arg Gln Pro Glu Thr Val Ala Val Met Lys
                165                 170                 175

Trp Leu Lys Thr Glu Thr Phe Val Leu Ser Ala Asn Leu His Gly Gly
            180                 185                 190

Ala Leu Val Ala Ser Tyr Pro Phe Asp Asn Gly Val Gln Ala Thr Gly
            195                 200                 205

Ala Leu Tyr Ser Arg Ser Leu Thr Pro Asp Asp Asp Val Phe Gln Tyr
210                 215                 220

Leu Ala His Thr Tyr Ala Ser Arg Asn Pro Asn Met Lys Lys Gly Asp
225                 230                 235                 240

Glu Cys Lys Asn Lys Met Asn Phe Pro Asn Gly Val Thr Asn Gly Tyr
                245                 250                 255

Ser Trp Tyr Pro Leu Gln Gly Gly Met Gln Asp Tyr Asn Tyr Ile Trp
            260                 265                 270

Ala Gln Cys Phe Glu Ile Thr Leu Glu Leu Ser Cys Cys Lys Tyr Pro
            275                 280                 285

Arg Glu Glu Lys Leu Pro Ser Phe Trp Asn Asn Lys Ala Ser Leu
290                 295                 300

Ile Glu Tyr Ile Lys Gln Val His Leu Gly Val Lys Gly Gln Val Phe
305                 310                 315                 320

Asp Gln Asn Gly Asn Pro Leu Pro Asn Val Ile Val Glu Val Gln Asp
                325                 330                 335

Arg Lys His Ile Cys Pro Tyr Arg Thr Asn Lys Tyr Gly Glu Tyr Tyr
            340                 345                 350

Leu Leu Leu Leu Pro Gly Ser Tyr Ile Ile Asn Val Thr Val Pro Gly
            355                 360                 365
```

His Asp Pro His Ile Thr Lys Val Ile Pro Glu Lys Ser Gln Asn
    370                 375                 380

Phe Ser Ala Leu Lys Lys Asp Ile Leu Leu Pro Phe Gln Gly Gln Leu
385                 390                 395                 400

Asp Ser Ile Pro Val Ser Asn Pro Ser Cys Pro Met Ile Pro Leu Tyr
                405                 410                 415

Arg Asn Leu Pro Asp His Ser Ala Ala Thr Lys Pro Ser Leu Phe Leu
                420                 425                 430

Phe Leu Val Ser Leu Leu His Ile Phe Phe Lys
            435                 440

<210> SEQ ID NO 2
<211> LENGTH: 491
<212> TYPE: PRT
<213> ORGANISM: Homo sapiens

<400> SEQUENCE: 2

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300

```
Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
            325                 330                 335

Asp Lys Gly Glu Ile Ser Glu Lys Ala Lys Leu Glu Asn Ser Thr Gln
        340                 345                 350

Ala Glu Glu Gly Phe Asp Val Pro Asp Cys Lys Lys Thr Ile Val Asn
    355                 360                 365

Asp Ser Arg Glu Ser Cys Val Glu Glu Asn Asp Asp Lys Ile Thr Gln
370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
            420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 3
<211> LENGTH: 99680
<212> TYPE: DNA
<213> ORGANISM: Homo sapiens

<400> SEQUENCE: 3
taattacaac tttaaacacc aaaccacagt catgttggca ctcagaattt gaatccttat      60
ctactgggct ccagaatctg tactttttaa tttatttact tatttctgag acagggtttt     120
gctccgttgc ttagactaaa gtgctgtggt acaatcacgg cttactgcag ccttgacctc     180
ccgggctcaa gcgatcctct tgcctcagcc cctgagtag ctgggaccac aggtgtgtgc      240
caccatgccc aactaatttt tgtatttttt gtacagatga gctttcgcca tgttggctag     300
gctggtattg aacttctaga ctcaagtgat ccacccacct cagcctccca aagtgctagg     360
attacaggtg tgagcccaga atctgtactt ctaacaacaa aaatagtttc taatacatac     420
aaaatacttg ataggcctga tggaggataa aggaattaat aaagtatatt ttgtgtcctc     480
cgggagctta ccatttagtg gaggaaatat gtattcccac aaataactgt ggggcaccaa     540
gttatgagta cttttacctc cactccaatc tgccactggc tactgagcaa tggtccaagg     600
ttagagcatc atatttagcc atagtataca ttggcatgct tactgggttg tgtggcagca     660
ataaatggca actgaaccaa agatgcagg agtctagcaa gacttttac ttctggagca      720 atttcaggct tccaaatcct tactgaatta cccttaattg caatttctcg tattactgag     780
atgatgagag tctaatcatt gagactattt cctcctaact tgttgctat atgcaggcaa      840 ccaagcttca ttctgactgg gggttacgct aacttggatt ttaaaccca attctgcagt      900 tcaagagaga tgataaatgg agtagaggga cctcctccct accctccccc caaaccccc      960 aaagccttcc caactcccta tatactctaa aagacagaca ctagaaacta acaacacat     1020 aatctgatgg gctgatcaat aatgcattgg ttttattacc tgaatatttt ggggttactt    1080
```

-continued

```
tttcatgtca gtctctcatg tcaaaaattc tcatttccct aatgcctacc ccctcaggcc   1140
ctcatctctc ttccatcttc ctcacgaatg ataatttaag gtcataaaac agatagcttc   1200
acactttcaa tataaactcc aaaaaataaa ttgttagcgg tatttatctg acccctatat   1260
tctagctatt atagtcagat aataaaatcc agggtgctcg agggaacaga tcaaggggac   1320
agttagaaaa cttaagcttc agtgtttctg ttgactctag aaaggcaaaa ctaaaataac   1380
tcatctgtag cctgaatatc attcccaata ggagttagat aaaagcctat cttggcaaag   1440
ctcaaagtcc ttaaagtttg ggtcttattt gtttgtttgt tagactattt tggatcttga   1500
gagtttgctt tgggatgggg aacagctatt agagctgttt ggcgagtggg tatgctagaa   1560
atgggttgaa attatgacat tagtataaat ttttataaaa atctaatttc tagactgggc   1620
aacatagcaa gaccttgtct ctactaaaat aaaaaaaaat tttaaaaaag ctggccatgg   1680
tggcacacac ctgtagtccc agctacttcg ggggctgagg cagtaggagc ccttaagcct   1740
gggaagtcaa ggttgcagtc agccctgatt gtgcaactgc attccagcct gggcaacaga   1800
acaagaccct gtctcaaaaa aaataataat aaataaaatt agtcattata taaaaattct   1860
ttctttttctt ttttttttt tgagacagag tcttactctg ttgcccaggc tggagtgcaa   1920
tggcgcgatc tcagctcact gcaagctccg cctcccaggt tcaagtgatt cttctgcctc   1980
agcctcctga gtagctggga ttacaggtgc atgccaccat gcctggctat ttttcatatt   2040
tttagtagag atatggtttt gccatgttgg ccaggctggt cttgaactcc tgatttcagg   2100
tgatctatgt gtcttggcct cccaaagtgc tgggattaca ggcatgagcc attgcacccg   2160
gcctcaaaat tatttctaat gtgtgcaaag atatctgata aaaactacat gactatgtaa   2220
aataaaacat actatttcct ctgcctggac tttctatttc ttcacccttc aagttacagc   2280
ttaaacagat ccatcttctg gaagcttttt tgaactccac ttaactccat ttcaactcaa   2340
tgagcacctt ctgtgctctt gaatgcaggt ttctgatgac tttggaggtt gtgccactgg   2400
aatagaggga aaaaacttct aggactttca tggagagctt atgtgttcat gaatattgag   2460
cagaacagga gttatttgca tggactgagc aaacagaaga ccaaaataat cttttttatga   2520
ttttttgctt aaaacgttgc ttattctttg tgttttttcag agtcaagaaa actttttttat   2580
ttggagctat ttcagctttt taacaactga gtaaaataca ctccagtgag caaattttgg   2640
agcgcatttc tttctctcta ccttatttct ctgtaatttg gaaactatgt ctacgtatac   2700
ttaatttatg gtagtatcgc tatttgcata agttcagtaa gcatctgttt tcttttgtaa   2760
caggacacta ttagagacac tagttatttt accaaggctt tgactggaat gacatgtttt   2820
cagacttttc agactgcttt gaggaattga ggttgagcta cagagctgat aaaaattcct   2880
tggaaaaact ggccaccttg tttttacaag gttcccaacc tgtggtaagt aaaaatgtcc   2940
ctttctgata ggcctaggaa tcccaagtta ttttggtacc tctagaaatg aggaattcat   3000
tcaattcata caggtatctg caggcacaaa taaatctttg gctgggctca agatgctttt   3060
aaaaggtcta atctgagatt ccttattaaa aaaacatcca gcaaagccaa ttttttaaaa   3120
aggcctatat agcaaataat tattcatgtt atgtttcatg caaacaatta ggcctagtat   3180
aaataaaacc aaagcttatt ttgcaaataa attggtcctg ctatgatttg tctttggtaa   3240
aaatggggga aaactggaga gggaaaaatt atgtttcaaa aaaaacctat agcatgcctg   3300
ttattagatt ctagccttgg ctgggcacag tggctcacac ctgtaatccc aacatttgat   3360
gaggccgagg caggaggatg aatcacttga gcccagaagt tcgagaccag cctgggcaac   3420
atagggagac cccatctcta caaaaaatta tttaaaaatt agctgggtgt ggtggtgcac   3480
```

```
acctgtagtc ccagctactt ggaaggctga gatggcagga tcactttagc cctagaggtc   3540
gaggcttcag tgagctctga tcatgccact gcactccagc ctgggcaaca gagtgagaca   3600
ctgtctcaaa aaaaaaaaaa aaaaaaaaaa agaaagaaag aaaagaaaag aaaaaaattc   3660
tagccttgtc cattgtttgt gagcctatac taatgactca catctgattg gttcttgggg   3720
atatttacct gaatccctca aggcttcaga tcagttctgc aaggactcct gaagctaaga   3780 cttt cacacc ttgcattagg tctcttgtag tttactgttc tcttaagtgc tatactaacg   3840
atgtggataa gaatactaac gttttt gtta taccaacatt ggggacccaa caaggcacct   3900
gggaatacat acagacaact gcaaaatggt ttcactcctc ttaccttggg ggcaacccctt   3960 gccccaacta tacccctgt caacaggaag agcagttgtc agccttttcc catctcccca   4020
gctcacacct caggattgag gtgtgctgaa gcacaaggga gggaactgaa accacctttg   4080
caaagattat gacagcaaga aaagtctaac ttgactgact ccatcttgct tctagtctca   4140
caggctggct gtctttgcta attcctgggg gcacaaagag ctaaccatgg gagggattta   4200
gtttatagtt tcacttggaa gcaaggatga taacagtccc tccctaaaac taatctcctc   4260
cttgcttaga gagtgaaaac taatgaaagg ccacaagatt agggttattg gagggacctg   4320
aattctgcta aagtataggt atactttat aatcccttac tgctcaggag tcatgtggcc   4380
agaggtcaca agatttgtga cttccccaat tgctcttata gataacatca ctactgtaga   4440
acttaagatt ggtctcttga gatgttttc agattttgt attctggcca tcaactgatc   4500
ctacctggac tcatgactca tgactcaact ggtcctgtgg cccccaccca gaggcagact   4560
cagctcactg ggacagtttt ccacacccct atgatttttt tcccaactaa tcagcagtac   4620
ccattaccta gtccccgccc accaaactat ctttaaaaat cctaacgtct gagttctcag   4680
aaagactgat ttgagtggta actccagtct ttctgctctg ctgccttgtc acttctttat   4740
tgtaatttaa aaaaaaaaaa caaaaaacaa ggtgaaggag ccaggcatgg tgtctcatgc   4800
ctatcattcc tgtattttgg gaggctgagc tgggcggatg acttgaagcc aagagtttga   4860
gaccatcctg tgcaacgaag tgaggcccca tatctacaaa aaataaatta tctgggtgtt   4920
gtggcatgtg tctgtagtcc caactgctca gaaggctgag atgggaggat tgcttaagcc   4980
cagaagttca aggcttcagt gagctatgat tataccactg cactccagcc tgggcaacag   5040
agcaagaaac tgtctaaaaa gaaaaaagt aagtacgttc tgatagtatg tctcataata   5100
tcctgtaatt ttcttctgt ataggcatc aaaatggcaa ctgagtgact gcttatctct   5160
gtatcatctt tcccaataca atatgaactc tatcaaagtg aggactatgt ttctctttta   5220
caccatggta ttcatagtgc ttagcatatt attagatgtt cattaaataa ttatcaacag   5280
aaggaatgaa tgaaccaatt aatcatgagt catgaggaga caaaagaatt tgtttggcta   5340
ttgtctgagt atatttataa tttgactttc cagaggtcat tgttgaatag atatgatgta   5400
tgctgttttc aaaagggtca ttgaaaagta aatgattaga tgaacttaca aattattaac   5460
tatcttcaaa cagtctcttt gtcactctgc tatatataca ttttccctt cttcccacac   5520 tcccccctgcc tttctttctg ctacaggtac agggtattaa caaagatggc agattctttc   5580
tcaaatatac agttttt aaa aaaaaaaaaa tccagaaatg gttttctcga catttgaaac   5640
aaagctagaa aagaaataaa tttcagtaag tatattgttt cctaagagac aagagtatga   5700
ctttcatctg ctgttatgtc agattgtttg atatcacaca atccagatta aatgcagcta   5760
aataggactg tctttgcttt ggaatcggc cttattagag ccaagaagct ttcttgcaaa   5820
tctataatat aaacaaagta tagtaggaga agtaagcatt attttgcact caaagaccat   5880
```

```
gagtttaaga gaaaaagtca ctattgtaac aattgctttg taattgtaaa ttatcacaaa    5940
tttatggttg ataaaggtct attccactat tgcaaatatg ttggaaggag ctgggatgtg    6000
gaaataaata agataaatat aaacatatac tatctgttgt atccctttct gtcttgttca    6060
tcttcactag atggtaataa taataaaaat gaattcagct tgggacttat aaagcattta    6120
taacaggcca gacactgttt gttctaaact ctttgtatat gttaactcat ttaatatatg    6180
caaccctgta aggtcactat aatcctctaa gatcaatacc atgagttagc ccagtttaca    6240
gaaaaggaca tgaatgcacc aagaggtgca gtgacttgct cagggcacac agtaagcgac    6300
agagctgggg tttaagctaa gatggtgtgg ttccacagac cttactttta ataatttact    6360
attttagtta ttacatataa tctcttgatg ctatattctt cctagaataa cacttataaa    6420
tcagcaagca tgcactgagc tctgacctag atgccatggg ggaaacaaaa aatgacacca    6480
tttgatgctt cactcactct atttggggtg tcttcctgaa ctgaaattaa tttcaaacgt    6540
ttagattttt cctgacattg tttctcagct gatgtgttag ggcatactgg agtgtcaaac    6600
tttgatctga ttcatttta attttgcttc accaacagta gatagaatgt gaagctaaga    6660
aggtcatgct gtgcagtaca gaatgtggta caaaccacta ggggataaga cacaagaagc    6720
agaaagtaat attatgccag ctccccaaga aagatcacag gtttctttga acatgtgaaa    6780
ttctttagtg gagattttg gctcttgtag aatgtaagct acctaagggc agagatttgt    6840
tctgtcttgt ttacagtcgt attccctagg agcaagtgca gtgcctgaca cagagtaaac    6900
aataaataat tgataaggaa atgaatgaat aattaaaaat cagagagtgg ggcaaagcag    6960
aaataggttt actctcacag tgacatagtg ccaacaaggg acaatagtgt gataacggtg    7020
catgatttta tagtcattgc tgtgtatttt tatattcttc ctatggtacg cttttttgatt    7080
atgtagatag cattttttta gtccttttct ttctttgtgc catgaaaaat tctaggattc    7140
agaaatttat cacgaacaca aatgtgtata caaatccttt ctaaatctct caaaggaata    7200
ctaatgcatt tacagttgca catccaaaat aaaagaacta ctctgtttgg ttttttgatag    7260
acaacttgca taacaaacag aaaacacagc cacaatttct agagaaatgc ttattaaaaa    7320
gacatacagt tctaaaaaac aaagtctact aataaaaaaa taaaggaaca attttaaaa    7380
gatgcacagc caagactaca gagtccttgt tttaaacaga gaatgcttga gttgagacat    7440
attcttcaa tctctgagtc ccactgttta gacatcaccc gtggtagttt agggaaagga    7500
tcatcttgga ccttaacaaa aaccatccag cttttcacta acaattttct tatctctagc    7560
tataaatagc aatctttcct ttctgaagaa ttgcaaggtc actttccttt tttatcaaaa    7620
acaaacaaat ccggttttgc tgggggtact gatctgagtt gggggagcta ctttgaagga    7680
ggtaggttta gtactggggg aggtaccagg agatcccagc ttaagataaa tgcccaaact    7740
ccctcagata catgagaagc agcagacaat agaaagaatc attgagcagc attagtataa    7800
ggcattatat tctacttgtg aaatttcaag aaaatgtgtc tttaaggcct aggcaggcag    7860
atcacttgag gccagaagtt cgagaccagc ctgggcaaca tggtgagact ctgtatctac    7920
aaaaaataca caaaaaaata gccatgcgtg gtggtacaca cctgtagtcc cagctacccg    7980
ggaggctcag gtggaggat tacttaagcc tgggaggtta aggctacagt gagctgtgat    8040
cacgtcactg cactccagcc tgggcaacag agccagaccc tgtctcaaaa acaaacaaac    8100
aaacaaaaaa caaataaatg taaaataagt tttaccttat tgggcgagtt atttctgagc    8160
gaccatttga tgcttcactc acactatttg gggtgacttc ctgaactgaa attaatttca    8220
aatgtttaga ttttccctga cattgtttct cagctgatgt gttagcttta tatacacaca    8280
```

```
cacacacaca cacacacaca cacacacgta ctcagcacat cttcaaatta cttctgtagc    8340
acaaaaacac acaaattgac caatggaaca gaaataagcc agtcacaaaa agacaaatat    8400
tgcatgattc cacttatatt aggaatctaa actagtcaga cttttagaaa gaatgttggt    8460
agccaggagc aggagagaga gagaaaaggt gggttgttgt tcagtgggta tagagtttca    8520
gttttgcaag gtttgaaaaa gttctagagc tctattgcac aacagtgtgc atagagttaa    8580
cacaactgca ctgtacactt agaaacagtt aagatggtaa ttttatatgt tttatagcac    8640
aataatttaa aaaatatagg aaggacatgg tctcagaata aagggccatc ttttatcata    8700
aagaaaaatt tgcaacccaa ttccaacatg ttaaggtgtt ctcttcttgt tgtttcattg    8760
agaactgcta aaagtctcag tgcccttctc atttggatgg tggtcctact caaacgtttg    8820
gagaccaaag ccccatttgg taataagaag gatgtgttgc ctggcctggt gctctgggca    8880
tatacacttc aggagaacct ttcgtaggta ggggttaagg attggaatct gtcctgacag    8940
aacaatgtct tcacacaatt aacacatagt tcacatacta gatgaaaaca aattccaagt    9000
ggactacaaa tataaatctg ggggagggag agagggatga ataggtggag cacaggggat    9060
cactagggcc atgaaattat tctgtatgat actgtaatgt tggatacatg ccattataca    9120
tttgtaaaaa ctcatagcat atgcaatata aactatagat ttagttaata ataatgtgtc    9180
aatattggct catcaatttt aacagatgtg acacgctaac gccaagatgt taataataag    9240
ggaaactgtg tatgtgggta gggcaggaaa agggtatatg ggaaccctat actttctgtt    9300
caatttttct gcaaatctca aactgctcta aaaaaattaa ttttaaaaaa tgagatgaaa    9360
gaagaaaaat gaaaaaataa aaataccaaa gaaataaaaa tagaagaaaa tataaattaa    9420
tttataattt aagaataaac tttctaagaa tatatcaaaa aactatgaat ccagaaggaa    9480
aagactaata cacaaccaga aaaatgagca aaagctatta atagactatt ttttaaaaga    9540
agaacaataa atgttcaata agactatgag agaaatgttc agtcacatta atactaaaac    9600
ttaaaattat gagatttcat ttttatctat gaaattggca aacatttta aaagagataa     9660 tagtaatcat gaggagccaa acaggcattt tcacatatca ccagtgagga ctgtaaattg    9720
gaatgacctt tggtcagaaa aaattttca aaacttggaa agcaaaatat gattgcataa     9780
tttgttttca tgttaggcat tgcctaacca gtccatctaa ggtgaattga atcctgactc    9840
gttattacag atttgcacat tttacaactg taaattcaaa tgttagtttg tagaaaattg    9900
gtgagatgct atattttgt ccaatggaga tataatttct gtcctgcaca gatgaaaata     9960
attttgctct gtaaagatag caccaaacat tatggtttat caccctgtaa gacattaatc   10020
agatttatat ctaatttagc aataatgtag aatgattta gtattctttt ttatatattt    10080
atgtatatat ataggatgta tatttacata tgtatattat atatagtatg tatatacata   10140
atataaatac aatatgtata taggtatgtg tacacataat acatatacta tatgtatata   10200
tgtacataat atacataagt atatacatca tatacatata tgatgtctat atgtatagac   10260
atcatataca ttatgggatg tacatacata tatacataac atatacatat attatgtata   10320
tattattata gatatatgta catatataca tacatatatg tatgtagtaa atgtatatat   10380
agatacatat gtgtatacat atatagatgt atgtacatat atctatgtat atacttatag   10440
atgtatgtac ataatatcta tatatatact tacagatata tttatataat atctatatac   10500
ttacatatat gtactatgta tatttagata tatacacata tttatacata tatgcatata   10560
cacatataca tatatatgta tgtacatata taaatagata tacataatat atgtatatac   10620
acatatagat atatatgtac acatatagat atacgtgtgt gtgtgtgtgt atacacacat   10680
```

```
attttctcat gtctttcttt gaactggctt tgttatcctg ctggtttcct cattaataag   10740
ttaaaattaa aacttgaact gtgcttactc tatatttgta tgagaatact ttttaacatt   10800
ttttaaatta tacatttgac atttttatagg agtataactt ggccaaatat tttaagtctt   10860
aaaagtgtac atgcttttta acctagcaat tacatgtcta agaaatgatc ctaaggaggt   10920
aaggacatgc tcaaaggttt agctctgaga atgtttctag atgtgctgtg tataataaag   10980
aaataccaga aacaaatgtg ccacattagg gcgctggtta atacctaaat gtgtgtgtgt   11040
ttgtttgatt gttttggggt ttggggattt ttttttttta agacagagtc tcattctgtc   11100
acccagaatg gagtgccatg cgatcatggc tcactgcaac ctcaaacccc tggggtcaag   11160
caatcctcct gccccagcct cctcagtagc tgggactacc ttgccccatc cctaaatgtg   11220
ttttaagaat ggttgtttcc aggtaagtaa aatttgtaag tttaaaattt ttctttttatc  11280 ttgttcagat tttcttgtga cactttcaaa gaaaaagtt tgaaagtcac aaagtctagt    11340
tatactgttc tcattcttgt tgacatctat tgaggtactt agccccgact atagttattc   11400
cctctgtccc aattcctgct actatcttag ggaaattcag agtccttaaa cagaaccaat   11460
ccaacactct ggctttttca ttccttaatt tcccatttcc agtgatcttt acctcctctt   11520 cactttgta attcactcta agatattttg atcctgtttt cattcagaat tagtcattgg    11580
tcctctctaa cactttgtg cttttttcctc tgctttgctt ttaaattaaa atgccttcat   11640
tgttttccca atttaaaaaa gcaatgcatg tttggtggaa aaacttttca gaaaatacag   11700
aaagatgtaa aaaagaaaat taaaacattg caactcgtgg atttgcactc agcatgttgg   11760
taaccttaga aacacattgc tgggaatagt tttttttttgt ttgctttatc taaatgagat   11820
cttactattt attttacttt tattatctgc ttcttgcctg aacaatttgt ctttccaagt   11880
gaataaatgc agatctacat tgacattatt atggctgaaa acaattaat tgtacagcta    11940 taatattctt taacccaggg tgtcttaact tcagcactat tgacattttg ggctgaataa   12000
ttctttgttg tgggaggctg tgttgtgcac tgaaggatat ttaatgcctc cctgccctct   12060
gtatcagcac tagatgccag tagctcccat ccctagttat gacaatcaaa aatgtctcaa   12120
gatattgcca aatgtctgct gtgggcacta ctgcctcaag ttgagaacca ctgatctaac   12180
caatctgctg ttgtttgaca tttaggtttt atctactttg tcacaattta aagcagcagc   12240
acttatgaag ctcctaacat atacaaactc aacacatctt caaattactt ctatagcata   12300
aatttctagc aaggaatggc acatacaaaa ttttgatgtc tattcccaga tttccctcca   12360
gaaagattgt attaatttag aacaccattg aaacagcata aatgtcattt cctgagatcc   12420
tgtctacttc caggtattgt caatctttt aatcttgctt tgtgataagc aaaacaaagt    12480
attactttac cctttaact tgtaattctt tgattgctta ccaggttggt aacctttact    12540
atatttatta gctatttgtg ttactgcttt tatgaactgc ttattcatct cctttgctca   12600
ttctttattt tgtaagagca ttaattcctt cttccagctt gtaatttttc tcataacctg   12660
atttaaacct ttcttcttat aacctttata aggttttctg tacagaagtc atacatttgt   12720
atgttttcaa attattagcc ttttttattat ggttttacct ttaatggtgc catacttaga  12780
aagatcacct ctaggtccag gcctggtggc tcacacctgt aatcccagca ctctgggagg   12840
ctgaggcagg cagataattt gaggccagga gttcgagacc atcctggcca acgtggtgaa   12900
accccgtctc tactaaaaat acaaaaatta gccaggcgtg gtggtgggca cctgtaatcc   12960
cagctactca ggaggctgag gaaggagaat tgcttgaacc cggagggtgg aggttgcagt   13020
gagctaaaat tgtgccactg cactccagcc tgggcaacag agcaagactc tatctcaaaa   13080
```

```
aaaaagaaga aagaaagaag atcacctcta aaatctctaa acttcagtat tttactctat   13140
taggctaacc tttttatttg ctgttatctt tcatactctt aacactaaat tttttttct    13200 ctcttgacca gtgcaccta aacttgaatg tacatataca tcatctggaa atcttattaa    13260
aatgtgtgtt ctgattcagt aggtttggag tggagtgaca gattctacat ttccaacaag   13320
ctcccaggtg atgccagtgc tgtccctggc ctgcactctg agttactagc tcctaaacct   13380
tcagcactca gtcctctgta cccctacct ccattctctg actccttcct gaagttgcct    13440
cccttcctac ctagtgtgaa ccccaatggc agcaatttca actatagctc atctctgttt   13500
ttccagaaca acaatcctgg caatctccat tccagtattg atgaagccac catttcttcc   13560
agtctccagc cacagcaccc tgcaggaaat cagatagtgt ccacgtactt ctcttaaaaa   13620
gataggattt ctaaggtaca tcagcaagcc ttcactttgt tcccacccag ttcccttcc    13680 cattcctaga gtaactttgc ctaaatttaa tcttctcaag ctccagtccc cctcctcaga   13740
cctcttagtc aatgaacaac aatgaaaggg aaacgtcttc aacccttcca gtggaaataa   13800
catttagcat agtgactact gcacaattaa aaaaaaaaa acctactcaa agactctaca    13860
atgtcatact aagacttcca actcttaggc caggcaaggt ggctcactca gtaatccca    13920 gcactttggg aggctgaggc agaaggatca cttgaggcca ggagttcaag actagcctgg   13980
ccaacatggt gaaacctggt ctctattaaa aatgcagaaa ttaggcatgt gtggtgtaaa   14040
aatacaaaag ttacgtaggt gtggcgatgc gtgcctgtaa tcccaggtac gttagaggct   14100
gaaacacaag aatcgcttga acctggaagg cagaggctgc agtgagctga gattgcacca   14160
ctgcactcaa gcctgggcaa cagagtgaga ctgtatctca aaacaaacaa acaaacaaac   14220
aaacaaacaa acaataaaac aacttctctt taagaaaaaa aaaagatgg ccaggcacgg    14280 tggctcacgc ctgtaatccc agcgatctgg gaggccgagg caggcagatc gcccgaggtc   14340
gggagttcca gaccagcctg gccaacatgg tgaaaccccg tctctactaa aaatacaaaa   14400
attagccggg cctggtggca ggtgcctgta atccgagcta ctcggtaggc tgaggcagga   14460
gaattgcttg aacctgagag gaggttgcag tgagccgaga tcatgccatt gcactccaga   14520
ctgggcaaca gaattgagac tccatctcaa aaataaaga aagaaataaa aaattaaaaa    14580
aaaaattcca actcttggaa aattcccttt aaagagttac gaattaagct ggtttattta   14640
tgtaataaac gcttcgcaca gttcttacaa tgtgcctgcc aaccttattt aggtaggtac   14700
aattaagact tccactttac acaccagaaa ataaggcaca gagtcgacac agccactgag   14760
tgtcagagca agaattggca ctcatcccgt gagcgcctca gttctttttt tttctttata   14820
tatactttaa gttctagggc acatgtgcac aactgtggca catatacacc acggaatact   14880
atgcagccat aaaaaaggat gagttcatgt cctttgtacg gacatggatg aagctggaaa   14940
ccatcattct cagcaaacta tcgcaagggc agagcgcctc agttcttaaa ccactcttct   15000
atgctgcggc agaatcactg gaagtctcag ggagtcctga gtgcgcaatt ctaggaaaag   15060
tatctatatc tgtaagaaag aaggggcagg gaatctaacg gttctcagct cttgaaggca   15120
cattagattc attcaaggtc ctctctaaaa atacactttc ttgggcctcc acgagaaaaa   15180
ttctattcaa ttagtcgtgg gcttgcatcc gtattttag tctgtaaaag tggaatgtta    15240
tctcaaatca gtggttttca aactttttat attctgcgga ccttgacacg ggcccccaat   15300
accctgacac ggttacttac aatccgggag agagtgggag aaaggggag agagggaagg    15360 ggagaggggg agggagaga gagagaatga atgagaatga atcttttaga gaggtagagg    15420
gggttggccc gtgccacaaa ccacctctca ggtttgagtg aagccttcgt tctctctcgt   15480
```

```
gcagagacca tgccatcctt ccagaaagga gcattttagg acgttttagg acgagagacc   15540
tgtaattggc ctaagactca ggtgcaggtg gaggaagcat cggatttaca acagtggtcc   15600
tgccttcttc gatgtgactt ccagttttaa attcaattct aatttacaca aatcccaccc   15660
actatgtaaa cttgttggaa aatgtcctgc actctgcact tcgtggcatt taaaacttcc   15720
acacacgcgc gcgttctttc tcgaagcccc gtgattgctt agcctcgctg ggcagcttgg   15780
cactgctggg agcttggctc gccctgccgg ggccgacgcc gcccgtcccg caggagcccg   15840
cgcggggctc agggcactca ggactccgca tgcgtcccgg ctccaggtgg gccccggcac   15900
cgccaaccgc aggaaacccg ccgagcccta aacgtctccc aagcggctgc agtctgcgac   15960
agagagtgtc cctcggtgga gcgcctgtg gctgcccagg ctacagccgt ggccgaggcg    16020
aggacacact tctgacctgg ggctccagca aagactgtcc gcgagcggcg actccatgcc   16080
cgcagccctc cgcccagctc agccgcccgg ccgcgggcac cagcagccgc gccacgaaag   16140
ggcgcaccgc gcgggcgccg tctctcctag gtgcgaaggc ggctgaggcc ccgcccggga   16200
ggcacccgcg cggctccgga gtgggccgga gggacgtccg ggggcggggc ccgggcgcgc   16260 ccgcccctctg accgggctat aacacccggc cccgccgggc ggccgcgggt gggtagaggt   16320
gcgcgcctgg gacctggtga ggctgggggt gcgcggggcc gggcgcagct gtggcagctg   16380
ccggacggcg gaggcgccag gaggaggagg agagggaggc gcgggcggct gggtcgaggg   16440
caccgaggct gcccgtgctc ccggtctctg gttgcacggc tcactcccga aggtgttgct   16500
tccagctttt gcctccttag gaggcaggga gcgtcagtgt cggagaccc tgagaccgga    16560 gtaccgagac gtagctggtg atgccccgc ctgccctcat gtgttctcag gttcttctta    16620
tttttattca tctctagaac atggacttcc cgtgcctctg ctagggctg ttgctgcctt    16680 tggtagctgc gctggatttc aactaccacc gccaggaagg gatggaagcg ttttttgaaga  16740 ctgttgccca aaactacagt tctgtcactc acttacacag tattgggaaa tctgtgaaag   16800
gtagggtccg tctcgtgaac actttgccaa accctcagtc ctcccttca gtattcatta   16860 aatatgcccc agcttcctgt ctgctcttcc acgcacctac tctgagtggc acagaacaag   16920
tcaaccggta ccgtgcgtgt tggttgtttt ctgcttttgt tgggaggaat agtaggaaga   16980
actgaatttt actggacttg tccattgtaa ttcagtgtca ctgagtcctt tccattattg   17040
gagttcttct gtcttttttgg atcttgcaga cattggttat ttgggatgta tgttttagtt   17100
ccttttcaag ataaactccc aagtaagtcc gtttatccgt ttcagttccc ctttgtgtgg   17160
gcttctttat atatgacttg gactgttaat gtcatttctt catgtctctt ttaaactgaa   17220
ataatgcagt tttgttggta agatttctgt gtcatctgta gttagccttt tatttaaagt   17280
tatgcaaaac tatcatttct gcaagtttct tttaatctaa gtagtacagt tctgttggtt   17340
agatttgtgt cgtgtataat tagccctatg gcttaaagtt atgcaaaaaa gtggttctat   17400
gattaaaggc tgttttaaa atgtatccat ttgaagaaga caatgctaga taatgaatat    17460
atattagtag tgattgaaac tcttcccagc attttcatat ttatcattaa taatttattg   17520
ttctaagtta gaaactacat aaagttattt tcattttat agacagcaag tttgaatcag    17580
ataaattaaa taatttgttc aaggtctccc agatggtgaa ttttatagcc aggactggca   17640
cccatccggc caaggcaaat aatttgatca gatatcgtta tttcatcttt ctttctttct   17700
ttctttcttt cttttttttt tttttttttt tttggtcaga gtctcgctct gttgcccagg   17760
ctggagtgca gtggcgtgat ctcggctcac tgcaacctcc ggcttcctga gttcaagcaa   17820
ttctcctgcc tcagtctccc gagtagctgg gattacagga atgcgccacc acagctggct   17880
```

```
aattttttg tatttttagt agagatgggg tttcaccata ttggccaggc tggtctcaaa    17940
ctcctgacct tgtgatcctc ctgcttcggc ctcccaaagt gctaggatta caggtatgag    18000
ccaccgtgcc cggccgagat accattatta cttaatcatc ttttattatc ctgatgttcc    18060
caaagaggtt accagaaaac ttagtcctta aatcaaaagt ttcataaatt ttatgcaatt    18120
tggatctcaa cttttttgtaa ggtgtgttca aactctacct tgattttagc tctgaacttt    18180
tgagtcaatt gagagtctca taattaccat attcttcatc attttttcaaa aaaatcaagg    18240
ctatggcttc tatattaaag aaaaagtatt atataaatgt atttatgtgc aatgcgaagt    18300
caatatcctg ggctgtgtgt aatagtaact ttgtttttaa acagcattgc caaagagatg    18360
gtgccagaat tactctatat tgctctataa tccaaaatta tagaggttgg gtgtgtgaga    18420
aatcatatct tgaatcagca tacgtattca gccttctgaa atcattttc cctagggcta    18480
gagtagagca atttaaaaag atctaggaat actaattata ttaattaaaa atatatagaa    18540
cacaactagc ttgagttatt gttcagtcat catttcaacc acaagatgat gaggatgttg    18600
ttaattttaa gtactaagtg atttggtaag gttttgtatt ttcaaacaca atgtgcttgt    18660
gacagttggg ggctctcttt cctaatatga atcagcagtt gtgatctatc ctgcatgata    18720
tcaaaccaca atcacagtga aagtcagcag gcttaatttt gttttaatt ttaccttgta    18780
tgcactcttg cggttaaagg cttgaggagt tatcatgtaa aaataaaatc tgacactagt    18840
ggttaaatat ttgtgttgaa tatgttgttc tgaataataa ctcggattaa gaaaaatccc    18900
aaatctgcca tttggctcca actggtagat gaaactgtat gccagtaact gggagtcagt    18960
tgccaaagtg tcactgcaca ttagtgtgac aattgagaga tggtgctcct ttgttggtgg    19020
tcttttttcac tagatatttt ccctaaccat tctgccctct gatgtaagat aagtttgctt    19080
agaaaacaga atttatgacc aggcccagtg actcatgcct gtaatcccag caccttggga    19140
ggccgaggcg ggaggatcac ctgaggtcag gaatttgaga ccagcctggc caacatggtg    19200
aaacgttgtc tctactaaaa atacaaaaaa ttaaccagac atggtggtgt gcacctgtgg    19260
ttcccgctac tagagaggct gagaccgag aatagcgtga acccaggagg cagaggttgc    19320
agtgggccaa gatcatgcca ctgcactcca gcctgggtga caagagtgaa actctatctc    19380
aaaataaaag aaaataaaca gaatttatta tacacgtgtt atttatttat ttatttatat    19440
tacatgtatt aacgtgggca gtcttaccca gaagggaaag taatattcct aagtaactaa    19500
atacatgttt agttttttgta aaacttaaa tatatgtgct atgcctatgt aaatatatgc    19560
atatcacata ttttctttgt tgtaattgtg gattatattc tgcttgtttt ttcatttcat    19620
gttatttcct tagatatttc catgaattga caaagtcggt agatgtgaat tcgttgctgt    19680
ttagtattct atcctcttga ttatgtgaat tttcttagtc attcacctct ttgagcatct    19740
gtatagtttt tggttaactc tgttataaac agggatacta taaaaccatt gatacatgtc    19800
atgataatta ccttctatta ttattggtga tttttaaaaa cgtttttatt ttgaaacttt    19860
taaaatccac acaaaagtta aacacatcta tacccagctt cagccatagt agaccatatt    19920
tcagttgagc cttttgaagg aaatcccact gcctagtgac atagtaaaga aaatcttagg    19980
tgaaacaaga gaagcaaaaa agtactgatg acttagttca gaaaaatcag aaaaggtaca    20040
gtgttcatca gttcgttcgt tcaatcctcc gttcaattaa ggaagcacct cccattttt    20100
gccccaaccc ctttgtctag aaggatgcct ggcacataat caataatcta tatctattta    20160
tttaatggat caaatatttg ctgagcaaaa ggcatgggaa gcaaacaaac gtgtgtgtca    20220
ttcattccct gccattaggt agctcatttt caaatacaaa tgtatttact gtgaatttct    20280
```

```
cagggtagtc tctccacaca caccccaaaa ttagtttagg aacattttat tattttttta   20340
aaaaatgaac ccttgtgttg agggttgact atcaatagat agcaatgaaa gaactgctct   20400
gctacataca aaaccccaaa gggccatttt aaatgagatt tcctaccatc tattttaaga   20460
atcttgcatt gactgggtgt ggtggctcac gtctataatc ccagcacttc aggagaccag   20520
cctaggcaac atgggagact ccatttctta aaaaaaaaaa aaaaaattta attaaccagg   20580
cataatggtg catgcctgtg gtcccagcta cttgggaaac tgaggcagga gaatcacttg   20640
agcctgggag ttcaaggctg cagtgggcca tgatcgtgcc accgtactcc agcctggcct   20700
acagagcaag accctgtctc aaaaaaaaaa aaaaagtatc ttgtcttgcc tcctgctaag   20760
tctgatcatc attgtatctg aatacagtag gcgggataat aacaccttcc ttactagtga   20820
taatactatt agagattttt taaagccagc caaatttagt agtctctgtt atcaagtact   20880
ttccatgtag taaatagttt aagacattat ttcgatctca gcaactcaaa gtaggcctta   20940
tcctcattta caaacaggt aaaatgaggc acagagaggt taattaactt gctgaagata   21000
acatagctaa gtattagaag attcaaactc agatctgcct atttcccaag cacctctcta   21060
ttctctttta aaaagcagct tgacatttaa gtctttaatc catcttgaat taattttgt   21120 ataaggtgta aggaagggat ccagtttcag cttctacat atggctagcc agttttccca   21180
gcaccattta ttgaataggg aatcctttcc ccattgcttg ttttttctcag gtttgtcaaa   21240 gatcagatag ttgtagatat gcggcgttat ttctgaggtc tctgttctgt tccattgatt   21300
tatatctctg ctttggtacc agtaccatgc tgttttggtt actgtagcct cgtagtatag   21360
tttgaagtca ggtagcatga tgcctccagc tttgctcttt tggcttagga ctgacttggc   21420
aatgcgggct ctttttggt tccatatgaa ctttaaagta gttttttcca attctgtgaa   21480
gaaagtcatt ggtggcttga tggggatggc attgaatcta taaattaccct tgggcagtat   21540 ggccattttc acgatattga ttcttcctac ccatgagcat ggaattgttc ttccatttgt   21600
ttgtatcctc ttttatttca ttgagcagtg gtttgtagtt ctccttgaag aggcccttca   21660
tgtcccttgt aagttggatt cctaggtatt ttattctctt tgaagcaatt gtgaatggga   21720
gttcactcat gatttggctc tctgtttgtc tgttactggt gtaagactta aacgttagac   21780
ctaaaaccat aaaaacccta gaagaaaacc taggcattac cattcaggac ataggcacgg   21840
gcaaggactt catgtctaaa acaccaaaag caatggcaac aaaagccaaa attgacaaat   21900
gggatctaat taaactaaag agcttctgca cagcaaaaga aactaccatc agagtgaaca   21960
ggcaacctcc aaaatgggag aaaattttcg caacctactc atctgacaaa gggctaatat   22020
ccagaatcta caatgaactc aaacaaattt acaagaaaaa aacagacaac cccatcgaga   22080
agtgggtgaa ggacatgaac agacacttct caaaagaaga catttatgca gccaaaaaac   22140
acatgaaaaa atgctcacca tcactggcca tcagagaaat gcaaatcaaa accacaatga   22200
gataccatct cacaccagtt agaatggcga tcattaaaaa gtcaggaaac aacaggtgct   22260
ggagaggatg tggagaaata ggaacacttt tacactgttg gtgggactgt aaactagttc   22320
aaccattgtg gaagtcagtg tggcgattcc tcagggatct agaactagaa ataccatttg   22380
acccagccat cccattactg ggtatatacc caaaggacta taaatcatgc tggtataaag   22440
acacatgcac atgtatgttt attgcggcac tattcacaat agcaaatact tggaaccaac   22500
ccaaatgtcc aacaacgata gactggatta agaaaatgtg gcacatatac accatagaat   22560
actatgcagc cacaaagaat gatgagttca tgtccttttgt agggacatgg atgaaattgg   22620
aaatcatcat tctcagtaaa ctatcgcaag aacaaaaaac caaacaccac atattctcac   22680
```

-continued

```
tcataggtgg gaattgaaca atgagaacac attggacaca ggaagggaa catcacactc   22740
tggggactgt tgtggggttg ggggagcggg gagggatagc attaggagat atacctaatg   22800
ctaaatgacg agttaatggg tgcagcacac cagcatggca catgtataca tatgtaacta   22860
acctgcacat tgtgcacatg taccctaaaa cttaaagtat aataataata aataaaata    22920
aataaataaa aataaaaagc agcttgacac agatggggat gattccatgg aagttgaggt   22980
cattagtaga gggttttagg accatggttt gggcacattt gacctgaagg tatagctcta   23040
ccaaggatct agagctgttc aattcagtag ccattagcca ctaagcaatt gaggagttga   23100
aatatgacta gaccaaactg aggtgtgcta gaaagtgact ttgaagactt aatacaaaaa   23160
aggaaaatat ttcactaata atgttttata ttgattacat gttgaaatga taatatttta   23220
gatatgttaa ataagaaata tttttttaaa ttaatttcaa ggccaaaagc agtggctcac   23280
acctgtaatc ccagcacttt gggaggctga ggcaggtgga tcgcccgagc tcaggagttt   23340
gagacccgct ggggcaacat ggcaaaaccc catctctacc aaaaatacaa aaaattagct   23400
gcgcatggtg gcatatgcct gtcatcccag ctacttggga ggctgaggtg ggaggattgc   23460
ttgagcttgg gaggtggagg ttgcagtgaa ccaagattgt aattgtgcca ctgcactcta   23520
acctgggtga tagggtgaga cccccatctc aaaataaat aaatatataa ataaaaatta    23580
atttcacctg tttcttttta cattattgta actagcagaa gattaaaatt atatatatga   23640
cttgcattat attttgatcg gactgtgctg ctatagagtg caatttgtta ttattaattt    23700
tttcctgcgt acaaaaggaa ttctagttca tttagaaaat ttggatcata caacaaagca   23760
ccaaaaagaa aattaaaatc tcaccatcca aaggaaacat ttagtagact gcaatcatac   23820
tacacagttt tgagccttt tacccccctg agtcaaatat cttatttgt ttgtccatgc     23880
aaacatgtta tctctaaaac ttgattttta atttctgttt tgtgtcctgt caatagatat   23940
tttattgtt aacttatgcc ccactggtga atatttagtt tgtttctaaa ctttcgctgt    24000
tatgatcaat gctgtagtga acatccttgt agctaagaca gcaaaatct gagcacaggc    24060
tttggaatca cctgcccaag ttcaaattcc ggattctcag ttttgtagct acgtgaccat   24120
gggtctttag aataattcct ggcacatagt aagtgctatg taaaagctgc tattattatt   24180
attattaata catacccaaa aaggaaatta ctaagtctaa agctgtttta agtatttgat   24240
atatatacca aattgccttc caaaaagatt gtgttgattt ataatttctt gggaaatgca   24300
tattaagaaa aataaaacaa ctcttctaaa acttacacta gtcataaatc aatactgtca   24360
ttagtgcttt gaaagatgat tgtagtatgt atttctcatt gttatgttgt aagtatgagg   24420
gagaatttat ttctcttgcc cctttcccta agaactctca ccttcccatc attaacagac   24480
attcactgaa ttcctctact aggagtccta taccatttca gatgttcaga aatctcccta   24540
acattggtta agattcttgc tcctaagagg aaagtactat gttcacatac acagatctct   24600
catgatcact tgccctcaac tggatagatt ttagccggtg atttaccctc agaaaacagc   24660
attgtatata aaattttggc acaacacttg gtcatccgtc acactctgct catttcccaa   24720
atatgctcgt aaaaccagtt tgcttgagat cctgtataaa atgccattg tgatgcaaat    24780
actgacatat tgaggatgaa tatgaagaaa accactaaaa tctaggaaat tcagctataa   24840
tatacatgtt tgtgatttaa agttatatgg gtttagtaag ccttccccct ttaacataat   24900
acgcagagta cctttctgag acatttatca gctatcagcc ttattcttat tcttgaaaca   24960
ttcagggttt cttaaagaca ttgccttttt ttttttcta tatggagtct cgctctgtcg    25020
cccatgctgg agtgcagtgt cacaatgtcg gctcactccg cctcctgggt tcaagcaatg    25080
```

```
ctcctgcctc aacctcctga gtagctaggg ttacaggcac ccaccattgc gcctggctaa    25140 ttttggtag  agacagggtt ttaccatgtt ggccaggctg gtctcgaact cctgacctca    25200
taatctgccc atctcagcct cccaaagtgc tgggattaca ggcgtgagcc actgcgccct    25260
tcctatcact tatcttgtca tgcttacatt attccccaca atttaggtt tttttttttt    25320 tttttttaa  gtagagacag gtgtctcact atgtagccca ggctggtctc gaactcctga    25380
gctcaagtga tcctcctgcc tcagcctccc gtagctctag gattaaagga atgagccact    25440 gtccctccg  cccacaattt tctaatgtcc tccatagggt aagatgagct tacaattatc    25500
tgagcctaaa accaaaatct tttttgtata caaatacaaa atatttcccc ccaacagttt    25560
taatatatac tgaacttttc agggatgcca ctatatgtaa attgagggga aattatattt    25620
tgttttgctc ttaacgtgac tgagagatat ttcatattca gagaatcctg acaacagtga    25680
acaaagagcc aaaccaatct gcatttgtaa tctatatgtt cacggtgact ctcaagtata    25740
gatacaagca tgtgatttct ttgtcttcta gtggagtacc caagttattg catatggata    25800
ccatatctta tgtaaattgc attctttttt tatttctgct ttatatagtt tgaacactat    25860
attgatcttt tgaaattatg tatgtaaatg tgttagaatt gtatgccagc atgataaaat    25920
agaagttgca aaatattgga tatgaaagca agaggcatca tctgatagag ttaagaacta    25980
ttggtgtaaa agcacaaaga gagctgttaa ggacccactt gaagctcatg tggccagcat    26040
ccaaaaggtg cttagtttct gttcttaatc cctgaacgtg tgtatctgac ggtaacactg    26100
tggttacagc agtatctaca tttgagatgt gataactgcc attagtcctg attcctcctt    26160
tcagtttgtg tgtttagaac acccctttct ctaagaatgc aaagtaagaa agtaagatgt    26220 aaaaaaaaa  acaaaagaaa accttaaagt gaaattactc aaaacacaca cacacacaca    26280
cacacacaca cacacacaca cacacacaca cacacactct atatcaaata ccaacatgca    26340
tttgggttaa gggaaggaga ctaagtcaaa tttagtcaaa tcttcctgtt tggagctagg    26400
cttggtcctg tagtcccagc tacttgggag gtttacacag gagaatcact tgaacccagg    26460
agtttgaggc tgtactgcac tatgatcgca cctgtgaaca gccactgcac tccagcctgg    26520
gcaacacagc aagagtctgt ctctttaaaa caaacaaaca acaaacaaaa aacacttctg    26580
tctagtgatt taaacaatt  gacattcttc ctagcaatta aatgtaatac tgtatagtag    26640
tttgtgaaga ggttagtaag tcctaatttg aatttgtgtt aaaataaaag acacaaaatg    26700
cacattaaaa atgtttctca tctctgtttt ctgaggactg ctgcatgtca caggtttaa    26760 aaatacacat tttctatctg tgaccttca  catacatacc tttgtcaagc tcaactggag    26820
ggcttaatct ccactgcatc aaaaaaaaa  aaaaaaaat  gctgccaact tcaaacaaat    26880
tgccttggag ctggcttcac agagttatca cgcacttacc cggagttgaa gataactacc    26940
ttgacagtgg ggatacaaag gcagtaatga tagtgcctac taccccagtc tttagtctat    27000
cacagaattc aggagaagcc aattaagtaa tccttctgtt tgtttaaaga actttcaatt    27060
agttgcttat ccagttttta aattattctg atgcaaatcc gtgaaaacta gaaccacact    27120
taaaaatcac aactaaagta tcatgaattg acagttattc aaacacataa ctaagcctcc    27180
tttcccacat aatacacacg cacatataca aatacaggca ggtgaaattt agcataacat    27240 catgtttta  gagcacgaat aaatgttaga gaccatttga tcattcatta cgttaattga    27300
aacttagttc aaaatgttgc ttcctccagg aagcttttt  ctattccctg gcagagtca    27360 gaatctcctt ccacacctct tctcctcttg agcatcttcc agtaactcta tgttcacata    27420
gaggccaagg accaggcttt gttcagcttt gtatcctagg cactaagatg tgcttattac    27480
```

```
atgtaacaga tactctcaag gacaaagatt aagagttatt atgtgcttat taaatgaaac   27540
atatgaatgc aaatatattg tatgtagtat attaaataat acataagtat ataggatgta   27600 cattttaaa  tatacttta  tattgttaca tatattatat gtaactttat acacttttat   27660
atagttacct atattgtatg taagttcttc agtccctcaa gaaaatgaca ttgttttctt   27720
atgaactttt tgttaaaatt agttttatat tagtagtaaa taatatgata acttagagag   27780
gtagaattgg gggaccacaa ttatgcccca gttcaagata agtcactggc atgtaggaga   27840
aggcctcaga gaagttacgg actttcaggc agtaaaggac acagttgaat tattcactgg   27900
ctagcctaaa atgggtctac ccccacccct tgccttcagc ccctaaaaac actgaccaaa   27960
catgtaataa gaaagagta  attataggag gttcaccacc atcacactca cccctgcctt   28020
cattaagaag tgtttaggct ggttgcggtg gttcacacct gtaactccag cactttggga   28080
ggctgaggcg ggtggatcac ttgaggccag gagtgcaaga ccagcctggc caacatggtg   28140
aaaccccatc tctactaaaa ttacaaaaat tagccgggca tggtggcagg tgcctgtaat   28200
tccagctacc tgggaggctg aggcaggaga atcgcttgaa cccgggaggt ggaggttgca   28260
gtgagctgag agccgagatc acaccactgc actacagcct gggtgacaga gcaagactct   28320
gtctcaaaaa aaaaaaaaaa gtgtttaaat aaatgcctct ggctttattt gaacagtcca   28380
ggaataattc aagggtctgt cacagaattt tgacaaagaa aaaaggtggg agggatcatg   28440
tgaagaaggc ctttttttcc ccaagagtta agcaggggcc aggcacagtg gctcaggcct   28500
gtaatcccag cactttggaa ggccaaggca ggccgattgc ttaaggccag gagtttgaga   28560
acagcctggc caacgtggca aaaccccgtg tgtactaaaa aaatgcaaaa aaaaaaaaaa   28620
ttagccaggc atggtggtgc acacctgtaa tcccagctac tctggagtct gaggcgggag   28680
aatcacttga acccaggagg tggaggttac agtgagccga gactgtgcca ctgtactcca   28740
gcctggccca cagtgagtct ctgtctaaaa aaaaaaaga  aaaagaaaaa gaaaagaaa   28800 aaaaaagctt aagcagagat atgaaaccct tccattttaa gtgtctttc  ccccctctat   28860 actcagaaat gttgtactta ttttaggtga aggcagatga tatgtctaac tattcttgct   28920
gtgagtggtc cagaagggca cagttttgga aatacacaga tgaactgttg aaggtagttt   28980
caccttaatt tttagtcctt gttaaatatt tattcccttg tccattgttg gtgactcagt   29040
tgagcccact cgttaaaatc cttttcacgg ggatagtcac tcttatgaaa acatagacac   29100
ctagagacat gtgggaagcg tagggtcatt taacatgtgg cgattctaca gcagttttcc   29160
cattgtttaa ctggagagat ttatttacag cttgtgttag gctgttcttg ggttgctaga   29220
aagaaatact gggtaatta  taagaaaag  aggtttaatt ggctaagcgt tctgcaggct   29280
gcacaagcgt ggccccagca tctgctcagt ttctagggag gcatcaggag gcttttactc   29340
atggcagaag gtgaagcagg accaggcacg tcacatggtg aaagcagaaa caagagaaag   29400 aggggtggg  aggtgccaca cgcttttaaa caaccagatc tcgtgagaac tcactcatta   29460
ttgtgaggac aacaccaagc catgagagat ccactcccat gacccaaacg tctcccacca   29520
ggctccacct ctaacatggg ggatgacatt tcagcatgaa atttggggga acaaatatct   29580
aaactattca caccttacta ataatactaa atgtgcacag ttaaatttca gataaagatt   29640
gttcaattgg ggcagacacg taattttttc cattgctctt tgggactcag atgaataatc   29700
ttagtgtggt agagataagc ctagctggtt tgtcatgtgt tactgtcagt tcctttcaat   29760
ttatgaagaa acagaaagat aaattgggaa atgtcacatt ctagccttga cgaactttt   29820 agttggactt ggccatcttt cgagttgtaa gaacatgtac ttctaagggt acaaaatgtg   29880
```

-continued

```
tttccaaact ctatggcata cagttctagc ataacaccat gtcagtcaat tgcagaaact    29940
tccaaacatt ttttacactg agagctcttt ggtcaaataa ttcttgcttg gaagtaaatc    30000
ccagtctgtg tgtgccaggc actgtgttag gctagagaca gagtcatgag caaatagcat    30060
ctctgctctg atgtttctta catgtgctag tgagggaggc aaacaaaaaa caaggcgagt    30120
tcagattttg atcattgcta tgaagcaaat acatagttta gtataatgga gagtgacagt    30180
tactgtggaa cataggttcc atgaaagcat ggagcctatc ctacttgtca ctgtatttc    30240 agtgcctaaa acatagcagt tactgtttga gagaatgttg tatggaaaga atgacaggag    30300
gcctgcctga aaagatggta ggttaaagtg agatctgaa aggtgacagt cagctagatc    30360
ttatagcctg attacaaagt gcacaaagtg caagtgatgt gcaaaggcct cgaggtggaa    30420
agagtagaac agaagtgaga ccagggtggc tggagcccag tgagcaaggg aaagtggtc    30480 tttgagcaag ttggaaggta cacaggggac agagcataga gtgccttcta agccaattct    30540
aaagtggaga gtttgaattc tgttctgaga ataatgggaa accattgaag ggttttaaga    30600
agagagtgat gcaatctgat gtgggtttta gaaagataac tttagctgct gaatacagaa    30660
aatggccaga atagaagcag ggagactaat ccagttacag tagtcctggc aaatgttgat    30720
gatggtgatt tggattaaga tgctctgtta ggaatggagg caagtgaaag gattggaaat    30780
ctgttttgga aataaaacca agagtacttg ctaatgggtt gggttgggtt gggttggatt    30840
ggattggatt ggattggatt ggattagatt ggattggatt ggaggaggaa ggcgtgtgag    30900
cagaagagga aaatcaagga tgatgcttag gttttgtgct cgactgagtg tatgaagtgt    30960
tcttatgtta gatggacaaa actggaagag gacagatttg ggatgaaatc aagggctctg    31020
attcagacat tttctttaga aattgtgaac tcctcaggag gtatccagtg gagacggttg    31080
ggtatataag tggagctcaa gagagaagtt tggctgcaga aagaaagttg ggagtcatca    31140
acatagaaat ggtattgaaa cctgcaggac taataaaata atctagcaag agagtagaga    31200
taaagaaaag aaggccagaa tcgagctata gcaccgtcac acagttagtc tgatagagta    31260
gaggagccaa gaatggagat gggaaaagat cagtaatgag gtagaaggaa aattaagagt    31320
gatgtcacag atgtcaaaaa ggggagtggc tcaagaaggc agttgttttg gggagtacca    31380
tgaccaccta ctagtgattt gctggaagga ctcactcacg actcaatata gaatcatatt    31440
caaggctaag atttattaca gcaaagggta tggtgcagga acagcaggat acagatatat    31500
ggtggcaaaa ctagagaagt cgtagtaggc tttcttgtcc tctctctgta gggattccac    31560
atgtttctca ggaatgcatg tttctctcca gctgtaaact gcagagacat atgcaaaacg    31620
cctccaccca ggaaagccca ctcaagtctt aggggttcag agctggtcaa gggagctggt    31680
cgtgtagcta tgtaaccagc caggatgcag accccaaact aggtactagg atgcatcagg    31740
aatcttcatg tcaactttaa acaatgatac tgtcttgata tattttgacc actgccttga    31800
gggcacaaaa ataacataac taattagtaa gcatttcagg gagtttagtg ctcaggattt    31860
gggtcagggt cattgctgtg actgcaggtg ttcccaaaga caagcaagaa ctgagtaaaa    31920
catactggct atgttaactc tttcctctag aggtcatggt taatgttgaa tgcaggtgaa    31980
agtcaaaact gagagccata aagttaattt ctatatccca aagtatagtt agtgaaatta    32040
tatttctctc cagatagatt cattccactt atttagtaaa catttattga atgcctaata    32100
tagttcatgg catgtgctag catgagacta taggggtaaa taagttagac atggcacctg    32160
ccctgaagga gttgacaaac caataaaacgc agatgtcatt agctgtgtgc gagaatatga    32220
cagaggtctc acggctgaga cctgaaggat aagagatcag ccaggtgaaa agggaaaggc    32280
```

```
gaggcaataa atagcacgtt caaaggcctg gaggtgaagg agcatattga ctttgaggag    32340
caaaagaagt tcagtgtggc tggaggggag aaaggagaag gtgagtgtgg ggtagattat    32400
ggaggacctt atacaggctg ttaaacacgt tttgcttcat ccacggggag atataatcct    32460
aagggttttt gcttgatagg aaaatgacag atttgttttc ttgattgaaa aatttctgat    32520
aattttacag ttagttttgc attgcaacag agattctctc tctctctctc ttttttttt    32580 tttttttttg agacaagagt ctcgctctgt cacccaggct ggagtgcaat ggtgcgatcc    32640
cagctcactg caacctccgc ttcctgagtt caagcgattc tcctgcctca gcccccgagt    32700
agctgggatt acagggtgt gccaccatgc ccagctaatt tttgtattta tagtagagat    32760 ggggttttcac catgttgtcc aggttggtct cgaactcctg accttgtgat ctgcctgcct    32820
cagcctccca aagtgctggg attacaggca tgcaccaccg tgcccagccc agagattctc    32880
tttaagaaat ttggtgcaac agtcatttct gggacaaaaa gtagtgagaa aatacaaaca    32940
caccagggta aataaaccag agcgccacaa aatgtaatat taagtgtgta aaaataataa    33000
tccctgagag ctatcagtgt gaaaagtttt tatttgaatg ccgtaattga atggaattgt    33060
tcatttaaac cttcaagtga atttatttt atgtctaaaa cttattagaa atgtttcaat    33120
ggtgattata tgtagtttct tttttgcctt caacagagca cagatcacac agaaaggaat    33180
gatttttttt ttaatcagca attttggaga caaattctat gaatgccaac ctatacagaa    33240
actgacaagc attaattatt cagaatgtaa agagaaatgc cagagtatta aggaacagat    33300
acctagattt aaacataatt ttggaatatt ataattatta tgaattacaa ccacttatat    33360
ttgaggcagt atgtaacagc tgtgtgcgtg agcaggaaca tgagagggaa cgtaacctgg    33420
tctcattttc tagacaagcc attcaagagg agcaaagaga gtgggaaaat gaaagcaatg    33480
ccactactga ttattgaaca tctttatctg ccatgcactg tgctaggccc tttacacatt    33540
ttccttcttt aagctattta aaaactgcga taagttcctt acattcccat tttataggca    33600
agagcaaata gattttacag atgaagaaat tgatgtccca aaatgatatc ttggtaggtg    33660
atagattcgg ttcggtaacc caaatgtgtc ttttagcgat ttatgtattc attcaacaaa    33720
tattcattga gttcctactg tctaccagaa cttttgtaag gggatgcaaa gaagaacaga    33780
cccaggtctt tccctttatg aactagggca gtgggcctta cacccaactg ccgtaatggg    33840
aaaagcattg taatggggct tgttcgtta cagtcaacag tgcagtgtag ggatgctttg    33900
taagctggcc tacagggtga ttggtaaagt tgagaaaggc ttatcaggga ggctgacatt    33960
tgaacaaagg tttggatatt accaggcaga gagatggagg tggtaggaat tccaggtaaa    34020
gcgactggga aaacacatgc tgtgcttggg tggcaggagc agtccaggga ggacatggtg    34080
ggactgtgct gcaagaagcc ttgtatgcca aggagatgag acttcccttg tacatacagc    34140
caaggataag aatttgatga cgatttctaa tgtatcttag catctaagtt cccttaattt    34200
gtgctcactg gaaaccacag agtttagaa ggcttttgtc attgtggttt aaaagaaaaa    34260
aatagattgt tcaaagaaca gtgatacata gggaaaatat tttgactcag gaacgtaatt    34320
tctcactaaa attggcaata tttgtagccc catgggaact atgtttccat aggacattct    34380
gttcgctgtc cttgggaagc tatctaaaaa aagaagaaaa aaacacaata aaaagaggta    34440 tttgggatc agtaataaaa gttgtatact ttattgaatg tgttactgtg tactagctac    34500
ttatccatat tattttaaat cctgacacct attaaataat aggtagtatt atccctgttt    34560
tacagatagg aaactgaggc tcagaaaaaa gtgcttgcc tgagactact tagctagtaa    34620
ggagcagagc tgggaattca aacccaggtc tgtcaggatt caaaacccca gttcttccag    34680
```

```
tctctagagc ctggtctcta gagcctggag acttctgtgg aggtgaccta ggccacttca  34740
ataggtgagg agacagagga ccgcttgggg atgcattcct taaatcagag cagctgattc  34800
tatgaatgcc aacctaatac agaaactgac aaacattaat tgttcagaat gtaaagaaaa  34860
ctgccagagt atgaaggaac agacatctag atttaaacat aattttggaa tattgtaatt  34920
attattaatt acaaccactt acatttgagg tagtgtgtaa cagctgtgtg catgagcagg  34980
aacttgagag ggaacgtatc ctggtctcat tttctaggca agccattcaa gagcagcaaa  35040
gagaatggga aaatgaaagc aatgccactg ccgattattg aacacctttta tgtgccatgc  35100 actgtgctag gctcttttaca cattttcctc ttttaaatta tataaaaact ctgtgataag  35160 ttttttttaag tatacagact tttgtgctaa attggaaaac ccgtactgga acctggggt  35220 gggggcgggg cagaggtctt ctaatgactg gccttgtgct ctttaagctg cactagctat  35280
cccactttga aaagaatgtg tgaaacacag ttgcagtcat gcatactcca tctccaaaga  35340
atggattcat tcttcaggcc atagtatact gactataatt ttctgtttgt aattacccag  35400
attccaagcc tgtttatagc atttatacct gaggaatgga atagtgagga tttgaagagg  35460
ccgcagtcct tgaggttttc tttgataata atatctgtgt agctgcatca aacacaaatt  35520
tgatattctg tgtatctgta gcacaggtca tgtgactgta aattcttttg atatcttgtt  35580
gcatactgag gtcaaggaac tggctcttga tgtaattccc cgcatcctca tgggagttgt  35640
taccatcata ctctggaaaa caaatgctga gatggattaa cttttttacac tgggtttccg  35700 catgggattt tataggaata aaggttccac taccagcagt gagtagcctg aagtctgcca  35760
cattgaccag gaacctttgc aagaataaac cgaggatgtg ccctctgcag gtgaatgtgc  35820
taggctctct ggggttgcca aggagtttga gtccccatcc ttgagtcccc atcaactaca  35880
tctagttgat gtacacgtga tcctttgcaa aggttctgag ccctctaaaa ctgatcaaaa  35940
ttgcatctgt tagaaaatat taaatatatt ctatatatca agccaaatac taggagcttg  36000
tgtaagcaac agagtatctt ggtggatcac gtgggtgttg ggttaggcaa aagatcccac  36060
tgttggccct ccccacaccc acatccttac tatgctctgg gcagacagag ttactccaac  36120
tatctcaaaa tgcccagaaa cccttaacca cctctactga tttgcctgta ttcaggagcc  36180
tccttcttca cagctgagat tcagacttca ttgagggaca aggtgaatga gagggtaggg  36240
gacagtaggg ggcagaatct ggtcatcagg aactttggac tttccagtga gcacagactg  36300
agatacctca ggtgctaaga ctgcagcacc cctggaggaa gactgtacac tagacaacaa  36360
caaggctggt tggcaggaca gcatctaccc agcatcctta acatccggga ggagatgatg  36420
gtgccgtgta gggacacttg accctgccca tagcagcctc agccctgtg catcctggga  36480 gtgaagtgat caggtcatgc aagtaactac atcagtcctc accactggga tcattgctac  36540
agaggggaag gcttttccct gtgtgttgga gatggagata gaagtgtatt aatggaggaa  36600
aacaaaataa gcttttacat ctgctaaatt aacagaatcc caggctgcca aaaccctgag  36660
gcttgctcaa tcagcagtcc aaactgtatt tcctctaagg gacaaattat gagctgctgt  36720
aaaggtacac acagtctagt gagaaaccat tcaattttga gggggaaact ctagggaaat  36780
agagtaagtt aaaggagtag agtgtgccag tatgagaagg caactctcct ggagtttgag  36840
ttccaaaact cagtgggctc ataggtcatg gtgtgatctt agaagtcata agtgaccaac  36900
aaggagttta ataacgcctt ttcttatact ccctcttttt acatagcctt tataccaagt  36960
tatcatctgg cagtcatttt agatataggt ttctaagtta gacggtaggg tccaaatgaa  37020
gtgtttggca aagtcatctt aattttttaa aacttgatat gaaaaagatg gtggtatcag  37080
```

```
gtattgaaat tgaggagcta tcagaatagg gaaaaattcc ccatttatgc ccatactcac   37140
aaatacacaa atatttataa acaataatga tacaggcagg catggtggct cacacctgta   37200
atcccaccac tttgggaggc caaggcaggc agatcacctg aggtcaggag ttcgaccagc   37260
ctggccaaaa tggtgaagcc ccgtctctac taaaaataca aaattagccg agtgtgttgg   37320
cgcatgcctg taatcccagc tacttgggag gctgaggcag gagaattgct tgaacccagg   37380
aggtagaggt tgcagtgagc tgagatcgtg gtattgcact ccagcctagg caacaagcgc   37440
gaaactctgt ctcaaaataa taataataat aatacaactt attttttttcc ctttggggg   37500 cttttccagca aaaccagaa agcctattag acaaatttta aaagagctgt aacactataa   37560
taagactgtt taataatggt tgagaacaca gagcccgaag aacacagatt gcctgggttc   37620
aaatcctggt tctgctgttc agtggctgtg atcttgaact actgtcttac cctatctgtg   37680
cctagttcct attttgtaaa atagaaataa tagttctacc tcgtaggttg tcgagagggc   37740
taaataagtt aataaacata aagtgctcag aatatgattg gcacataagt gctatggaaa   37800
tatatgctac tcttactgca gttacataaa ttgtgatatt tggcagcctt gaagcgtggc   37860
cctgccatat gctttgtgtt taaaaccctc aaactactgt ttattgaggg catctttgat   37920
gtcaggcaca gggctaggca atgttcctgc tgtatctcaa tgaatctaca caacaccta   37980 tgaggtaaat accaatttac agctttagat actgacttgc cagtggttaa gtaacttgcc   38040
caaggccaca aagcaagtac ctggtagatt caggactgaa gcttcaagtc tagagagctt   38100
ggctccagcc gcagctgcag tttgggctga ccttgttcct gccagcacac tttgggacct   38160
gggccataca agttatagca tcctggacag accctctatt ttatagaaaa ggaacctgag   38220
gccctaggat taaatgaatt gccagaggtc actctccaaa gagactctga ggtccagatt   38280
aggaaacctg aactaacatt gaagccgtgt cttctgtat aagatccaac tgcttgtggt   38340
atgtttggcc aaaaagactc aggttaaagt cagataccaa ataatatatt gacatctagc   38400
atatttatgc ccagatgccg tatagcaaat catccttcac tttaattagc ttatagttat   38460
atactcgaca atgtgaatga acagagaaaa acaaggtatt tttttttcat cttctaaatt   38520
tgcttgggaa attcctccgt gtcttttaca ggtttaaaaa tcatgtttaa cgataatgta   38580
gttatcttag gaaaagacc aacccatttt tatcactctt tatcattggg ccatcacaga   38640
tgagagcttt ctatcttata gaatcatttg cacaaagtat atatgaggat atacagcatt   38700
gtatttgtag catttcttat aatagtaaaa aaatgaaatg atacagtcat ctagttaatg   38760
ccactgagtt gtacacttag aatggttaaa taacaaattt tgttatatgt gttttgccat   38820
atttaaaaaa aataatagtt taagaaacta gtgacttgta tacttaaact gagtggattg   38880
tatagtatgc aaattatgtc tcaataaaga tattttttaa aacccataca tttatccata   38940
gagaattggt cagattatgc caaacccagt caatggagta ttttacaacc tttattaaag   39000
aattaggtag atttatatgt tttgacatgg gaggatgtcc agaatatatt gtgaagtaaa   39060 aaaaagttg atgtgcattt ccatatgctg tatacacacg tctacagttt tgtcttatga   39120
gtaacactct tgtaaatgtc attatgcaac ttggcttttt cacttatgtg tgttatgtta   39180
gaggttagta catatagaga tacctcattt ttttaactgt ttcaaactat tctgtggtat   39240
aatcttatct tagtttattt agtcatttcc atattgatga gtcttaggt catttataac   39300 ttttagatat ttcgaagaat gctgcaataa atactgttaa acaagcacat tagctccata   39360
atttcccaag ataggcacta ctaaatcaaa agtacatgc attttttttcc tcaagtttct   39420 ttcttttcatt gatgatgctc ttcttcctcc tcttcttcct cttcttcttc ttcttcatta   39480
```

```
ttattattat tattatactt ttaagttctg ggttacatgt gcagaatgtg caggtttgtt   39540
acataggtat acatgtgcca tggtggtttg ctgcacccat caacccgtca cctacattag   39600
gtatttctcc taatgttatc cctcccgtag ccccccacc ccccaacagg ccccagtgtg    39660
tgatgtttcc ctccctgtgt ccatgtgttc tcgttgttca actcctactt atgagtgaga   39720
acatgcagtg tttgattttc tgatattctg atagtttgct gagaatgatg gtttccagct   39780
tcatccatgt ccctgcaaag gacatgaact catccttttt atggctgaat agtattccat   39840
ggtgtatatg tgccacattt tcttaatcca gtctatcatt gatggacatt tgggttggtt   39900
ccaagtcttt gctattgtga atagtgctgc aataaacata tgtgtgcata aaggtatat    39960 gcattttgt gcttgatgga tactgacaga ttaacctaca agaggatgta ttatttacac     40020
tcccagcccc acgtgagtat gtgtatttcc ccacatccta accaacacta attttttcc    40080 attctaatgg gtgaaaaaaa aaatctccat tttaagttgc attttcactg agcatggtgg   40140
tacacaccta cagttccaga gacttaggag gtcaagatgg gaggattgtt tgaggccagg   40200
gccaggagtt caagactagc ctgggcaaca tagcaagatc ccatctctaa cgaaaatttt   40260
tttaaaaact agccaggcat gatggtgcat tcctgtcatt ccagctaccc aggacaccga   40320
ggctggatga ttgcttgaac ccagggccat ggtcccacca ctgaactata gcctgggtga   40380
cagagcgaga acctatctct acttaataat tagtagcatt tacatgattg aaaatcagaa   40440
tgaacatgtt ttcacattaa ttcaacatta gataaacatt gaggtactgc cccagatgaa   40500
caaacacaaa cccctgcccc tgtggaactt ctgttaaact ctattggtca tttctatttc   40560
ctcatgccat ttgcctgttt ttctatttat tcatgctttg ttatgtgtgt ggcaaatatt   40620
ttcacctctt ctgtggcttg tcttttgagc tccattttca gtatctttgg ccttacagaa   40680 gttttttaatt tttatgagat cgtattcgtc agtcctttc tttatgcttt tatgttccat   40740
gcctcactta aaaaggccct cttccccca aggtcataaa tatattctat accctttca    40800 atattttat ggttttagtt tttatgttta gcacctaact ccatctggaa tctattttg     40860 ggaatcgagt ggtatgtaga tagatttcat gtctgacaat atatatttt gagcactcaa    40920 atttttaaaa agtatgtatg actttggtaa gcagaaagag ccaagaggag tttgaagaga   40980
cactcagaaa gtggatgtcc attctgggtg ggcccaggag tttgcaattt tagcagatac   41040
ctccagagaa aagagaaagt gatgagaaaa aaaaaaaaaa agctgtgtcc tgtggagtag   41100
attcaggtca taatggctgt aggtagagac acagcagaaa gagtagcccc gggttggcct   41160
tgtatcctgg tacctacagc accttaggaa atacataaaa tacatgaaat gtcacagctt   41220
tgcaagaact agaagaccag ccagaatgaa tcagagaagg gattcttcag tgtttctact   41280
tgtaatggaa ttttttaatcc ctcatctggt acaaaaatga gtttgagata atagtccatt   41340
taaaaataac ccaagccggt gtggtggctt acgcctgtat tcccagtact ttgggaggcc   41400
gaggcagggg aatcacctgt caggagttca tgaccagcct ggccaacatg gtgaaacctc   41460
gtctctacta aaaatacaaa aattagtcag gtgtggtggc gggagcctgt aatcccagct   41520
acttgggaag ctgaagcagg agaatcactt aaatccggga ggcggagatt gcaatgacc    41580 cagatcgtac cactgcactc cagcttgggc aacagagtga gactccatct caaaaataaa   41640
taaataaata aataaataac caacccagcc ctggattaat gatgaattt cattctggct    41700 agcaaaggtt agcaaaagtg gatgactaca tgtaggcatg ttaattaaca cttttttagat  41760 tctggaaaaa gaatgttgtg tggcagaaat atgggtacaa atgtgcaagc cttctgtaga   41820 tgattctttta aaggcaggtg gagtgggagc cgctgggcta acctacccca aatcactgca   41880
```

| | | | | | |
|---|---|---|---|---|---|
| cttcctttct | tcccttgtca | ttaaaaccat | atgacccctt | tagtgtctgt | gttgcactca | 41940 |
| tgagttcaga | agttccaatg | catctatcaa | acacatgtgt | ttgcctactg | tgcatgttgt | 42000 |
| tctaagtgct | ccttcactgc | ttctgacaac | cctatgaggt | actattataa | gcctccttt | 42060 |
| acacatgagg | aaactgaggc | tccagagagt | taaataagtt | gcccatagtc | ccacaggcag | 42120 |
| tggtggcatt | gggatttgga | ctcaagttgt | ctagctccag | gttcgcagaa | tcaccctaat | 42180 |
| aatgtgccct | ccaaattggc | tatttcagca | actgcagtgt | tcaggaaaga | attatactct | 42240 |
| gatgagcctt | catgaggcag | ggttgaaaaa | cctgtgtcag | gaaagatat | gacaccttac | 42300 |
| tggttatcag | accatgctag | aaggagcctc | tttaaaatcg | aacaacagag | ccactgctct | 42360 |
| ggtgcaagca | gcactctcac | ccagccctct | gacctcagtc | acagtgtgag | ctctatagtt | 42420 |
| cctggcaaac | tttagccatg | gggtcaaaaa | tggagaagcg | tgccttcagg | tataagatgt | 42480 |
| gatgtgttca | tgcagggatt | agctctgttt | aggcttaatt | ctggaagcca | gggttcttaa | 42540 |
| tttggttccc | attccctgac | ggaatactat | gcagtcctga | taatgaatga | tttacattta | 42600 |
| tacaacagta | tgcatggatg | caccacaggg | gacagtgcct | ggaaataggc | acaagggtgc | 42660 |
| tttgaggctg | ctgtctacac | aaatgtgtgt | ttagtttatg | aaaatccaca | gtggcgcctg | 42720 |
| taatcccagc | actttgggag | gctgaggcgg | gcggatcatt | tgaagtcagg | agttcaagac | 42780 |
| cagcttggtg | aaaacccgtc | tctactaaaa | atacaaaaca | attagccagg | tgtgatggcg | 42840 |
| gatacctgta | atcccaggta | ctcggaggc | tgaggcatga | gaatcacttg | aacccaggag | 42900 |
| gcagaggctg | cggtgaacca | agatcgtgcc | actacactcc | agcctgggtg | acagagtgag | 42960 |
| actttgtctc | tcaaaaaaaa | aacaaaatct | acagtgagct | cttcagcata | tagctttctc | 43020 |
| tgcatattgt | attccatgta | ttcattgtac | tggattcaat | gtacagtatt | ctatgtatat | 43080 |
| tgttatttca | ctgaagagtt | ttttcttaat | ggcgtgaatt | agagtcagct | gaggtatttg | 43140 |
| tgaaaaatgc | agactcctga | actcacgcct | caagattcct | gttctggatg | gggcccagga | 43200 |
| gtttgcagtt | ttttacaaat | acctcaggta | attctgctgc | aggtcatctg | aagatatacc | 43260 |
| tgtaagaaca | tagcaaagct | gcagacctgg | tctgctgttg | atgtgcttaa | tactgggcat | 43320 |
| caataggact | ctataagtag | agcaaaagaa | tgacttgaga | atgactaggc | tcacacattg | 43380 |
| ggatggtagg | aaaacagcct | ggtgcactgc | aagggtaaca | ccatcttgaa | gcgaaaccac | 43440 |
| cacgatgacc | gatgcttgag | tcctgcatgc | caaggtgttc | ttgcagcaag | gccagaaaac | 43500 |
| aatgcctgta | gcacagataa | cccctcataa | acatgcttat | ctgacttccc | cagtggtcac | 43560 |
| cagtgttccc | caggaggatc | tgagacatga | ccagctgtct | ttactctaaa | cacttgctat | 43620 |
| ataaggatc | atttctggtg | ggtggacaca | gggactcact | ttctggagca | gcccaagaca | 43680 |
| tcgcttctat | ttgtaagtcc | ctattaaata | ttttttctga | agaactggat | ttatcagcct | 43740 |
| ctttcttaag | cctcttagtt | ccctctgcct | ttgtgggtag | gtttgcgtag | acctactcac | 43800 |
| caagaaacaa | ggctatatct | tacatgtatc | catgattttt | tttaatgcac | aaaaatgtaa | 43860 |
| aaagactata | taaatacct | acaacaagat | ttctgttggc | caggtacagt | ggctcatgct | 43920 |
| tggaatccta | gcattttggg | agggtgaggc | gagtggatca | cttgagccca | ggagttcaag | 43980 |
| accagcctgg | gcaacatagc | aagaccctgt | ctttacaaaa | agtacaaaaa | ttagctgggt | 44040 |
| atggtggtat | gtgcctgcag | tcccagctac | tcaggaggct | gatgtgggag | gattctttga | 44100 |
| gcccaggagg | tggaggcagt | ggtgagctga | gatcacacca | ctgcactata | gtctgggtga | 44160 |
| cagagtgaga | ccctgtttaa | aaaaagagag | agagagagaa | aaaaaagat | ttctctgaat | 44220 |
| ccttctcatg | cgtatcatga | gagatgtttt | aaaatgtttc | tatattttgg | ccgggtatgg | 44280 |

```
tagttcacgc ctgtaatcct agcaccttgg gaggctgagg cgggtggatc acctgaggtc    44340
aggagttcaa gaccagcctg gccaacatgg tgaaacccccc atctctacta aaaatgcaaa   44400
cattagccag gcgtggtggt gcatgcatgt aattccagct actcgggagg ctgaggcagg    44460
agaattgctt gaatccggga ggtggaggtt gcagtgagcc gagatcacac cattgcactc    44520
cagcgtgagc gacaagaatg aaactccatc cccccaaaaa aaccactttt ctgtattta    44580 atgcacagtt taaaaatgcc agacctggct ctattctact taggtttctg ttcattagat    44640
aggagtcatt catgtatgac tgaatcacta tgaggatcct cctctctctc ttcttcccct    44700
tccacccaca tgccaggctg tggttcagac tgccttctgc tttctcacgg gtctctgttg    44760
tgtgatcttg tgcccacctc tctgtgtgtt aaatggagag agtggcttga acagtaccct    44820
catggttggt cttcaagagc tcatctaatt ctgaatggta gttgggcatg tctgaaggta    44880
ttagcaattc tgttgctcag cattgctgat gtattgagca atgtgaaaac cttggcgaat    44940
cttgttgcca tcttccccta agaatctgcc tcatcctgaa gcccaaccat ttgactctgt    45000
ggtaaaatga agtaacttca gtaaggtcca tgtctaccaa tttcttaatc tcatttgagg    45060
taaatagatg cacattatca gaaaggactg gccactatgt actgcaaatg atgggcacag    45120
agttgtgatt gtcccagcag acttgagatg agctagggat acatcagtcc attatgagac    45180
ggtatctgtt atagtcaaga gtgtctctgg aatggcttct tgtaattatt tggactttct    45240
accaaggttt ctgtgccata gcctatggaa aagtagattc ctttcaagag acctgacttg    45300
ccaagcatgg tggttcacac ctgtaatccc agtgctttca ggggccaagg cggtgggatc    45360
acttgaaacc aggagtttag gaccagcctg gcaacaaag tgagacccccc atctctacaa    45420 aacattagcc aggtatagtg gcgcatgcct gtggtcccag ctacatggga gggcaaggcg    45480
ggaggatcac ctgagcccag gagttccagg ctgcagtgag ccacgttcac accactgcat    45540
tccagcctgg gcaacagagc aagacccagt caaaagaaag aaagaaagaa agaaagaatg    45600
agagaaaggg agggagggaa gaagggaggg agggacggag ggacggacgg cgggacggac    45660
agagggaagg agagacagag ggagggaggc ctgacttgta tatttatgtg cacgaaatcc    45720
gttctaggcc tctgaatatg gcacctggcc cactctttct tgagaacagt ttgccagtga    45780
gcaatgtgcc tcatgtcctt tgtgaaactg gcagagcata aattattaat ttaaaataca    45840
caaactaaga tcaagataag atgtgctttaa atgaacgggt aaactcaaat ggcttattaa    45900 cacctttcatt tcctcatgct gcttctgaaa tgggcatttc tcaacttaca ttttaaggta   45960
ggagctgatc tgagatgcaa gttaattata cagtttgtcg aagccaaaga gttgggtttg    46020
ggagattttc tgacctgaaa atgttcagtg gcggtgccca tgtaatcttg ggcctactct    46080
gacagacagt tcagagcctt aacattcagt gttggtcctt tggatatatt gaacataagc    46140
tacagtttac gggtatgaga ggacattatt gactgagact tcaatagttc caagggggaa    46200
aaaaaagaga aagatggctt ttttaaagct actgtcttca gctcaggaaa aaacatgtga    46260
tcagccgact gtaaatgcac agcttgagaa atttagcaat tcccaaaata ggttcaagtt    46320
tctttgtgag catgtaggcc tacttgcagg taacattgac tttgttaaca acgtttgtta    46380
acaataacat tgtaggcagt taatgtctca gagctcttat agatacaaaa gaaataaac    46440 ttacaacttc cagaaagcat cttctcattg atgagtctaa ataatgctca tctattggag    46500
aagcaacttg ttaatagtga cttttttgtca cttttgtaga gtggggagag ggacatggga    46560
gatgaagctc ttactttatt tgggaagtga gatgtctcaa gttctttatt ctaaaaaagg    46620
taaacatcag ttgcctctga ggtagtaata aagaaggtc tgttttactt tggaggaaca    46680
```

```
ttaaccttag agtaaaacaa acgaaaacac agttcaaagc ccaggctgtc tgagcccatc    46740
tcgtcatttg taaaatgagg ataataatac ctgccttact tatctcatgg tgtttctgtt    46800
gaggattaaa tgataaagca ctttggaaat tatgtaaaat atctgtattt taagcaggta    46860
tgatttcccg aaatccttga gttttttcctc tgattccatg attatgacat cacttaaata   46920
tgccacccct ctgctatcct aatacccccaa atctcagtga aacactggaa aagtccgaaa   46980
ccaatagaga tttctaaagc agatcccctt attatgcccc tcaattagtg atcattgtta    47040
gtgggtctgc tcagagcatc attgccaagt gctttgataa gctgaagaaa tctgttgata    47100
atttcttgag gcatggtatt tcagtgtgtg gaatacttgg gtactagttc ttgggagttt    47160
tttaaagtaa aatacttata tttgtgttga ctttgcaaca gcaggtacag caaatttcac    47220
atggtacctt gctacagaaa ttaattagta ccactcatgg tttaaattat gtagaatgat    47280
agtatgctca tattcttctt ggctgtctta aaaatgaata gaaacaaaaa ggtaaacaaa    47340
gctcatattt acctctcctt ggaaagaggt tgagtgattg tcatgtagct tctcatttat    47400
caagtatgtg ttatgatttc gttaaaggat aaattgaaag gattcttaaa gcaacaaagg    47460
tttggtcctg cattgatgca tattaagtaa agtagagctc ctcagttggc attcccaggc    47520
tgggtgacac agaggtgcct ctttctgata ctctccttcc cagctcctgt gccatcccct    47580
cccctctccc cttctctctc ctctctcccc ttcttctcct gtaatacttc tgctacttgc    47640
tctgttctac ccagagactg aaggaagtga gtggtgatct aattgagact gaataagtcc    47700
gaacatttat tttccttccc cttcactcca tccaaagtcc aatcctgagg aagacatgga    47760
ggttatgatt aaacttgccc aacactcaaa ctttactgac tgcttattct tatgttaatc    47820
acttggcctt tgctagatta atgactgagt gaccagaagt ctcaatgatc ccataaatcg    47880
tatgatttta aactatttgt gtagcttttg ctagttgtaa taaaaatttt cacatgattt    47940
tttttccaaa tagagaggtt taataaagct aatgtgcttg accaggtttt ggagagttta    48000
catactaatt tcttaacccc tttctaatat ggttagtata gctctgtgtt ttcatcagag    48060
agaagcagac tgtgaattcc tcaccttggg gcttccattc tccctccagg tggcctcacc    48120
tttcaggtga acaacctgac ctctctggct cctaaatccc acccttacaa gccgcaggag    48180
ccggtgcatg ggggcatagt ttcttacctt tacctttttc aaacctttcc ctcctcacca    48240
gctttttttt aagactttat tttcttagag cagttttaga gcaaatttgc tgtacctact    48300
gtggcaaagt caatacaaat ataaatattt acttaaaacc caagaaccag tacccaaaag    48360
caaaattatc taaagcaaaa ttgagaggaa ggtacagaga tttcccacat accccttgtc    48420
cctatcccca cacgcgcata gcctctccca tgatcaatat ccccccaccag agtggtacat   48480 ttgttacaac taataaaacct acactgaagt aggggtttgg acaaatgtat aatgacattg    48540
tagtatcata cagaggagtt tcactgcccc aaataccccta tgtgccatct tttcatcctt    48600
ccctcctcac tagcctttgg caaccactga tcttttttatt gtctccataa tttcgcctgt    48660
ttcaaaatgt catatgcttg gactcatata gtatagcctt tcagattgg cttcttttac     48720 ttagtaatat gcatttaagt ttcctccatg tatcttcatg gcttgataga tcatttcttt    48780
tcaacactga ctcgtattcc attgtctgag tgtaccacag gttatttatc ccctcaccta    48840
ctgaaggacc tcttggttcc tttcaagttt tggcaatgat aaataaaaat gtaaatagct    48900
gtataatttt tatatggacg taagttttca gtttattttg ttaaataaca aggagcttgt    48960
ttgctggatc atatggcaag agtaggttta gttttgtaag acacttgcaa actgctttcc    49020
aaattggcca ttttgcattc ccaccagcaa tgaatgagag ttcctgttgc tccacatcct    49080
```

```
cgccagtatt tggtgttgtc agtgttctga attttttgcca ttctaatagg aatgcattga   49140
tatctcattg ttgttttaat ttgccttttcc ctgatgacat atgatgtgac atatgatgac   49200
atcttttcat atgcttattt gccctctgtt tatcttcttt ggtgaaatgc ctgctgtttc   49260
catcttttgt ccatttttta attgagttgt ttattttctt attgttgggt tttcagaatt   49320
ctttctgtat tttggataac tctttcatca gacatgtctt ttgcaaacat tttctccaag   49380
tctgtggctt accttttcat tctcttgatc cctccagctt tttatttaga aaattttcag   49440
tcctatagaa aaaatacaa aaatagtaaa ataagcactc acacattatt catatacatc    49500
caccagttgt taatattttg ccacatttgc tttatctctc tcatgagctc catctgttga   49560
ttttactgaa ccattagaag tgataaatgg catgtcacat catcccaaaa aacaccaata   49620
tgcatctcct aagcatgact tcttactgcc taatcatgac acatcattat taaactaaaa   49680
ataataactc agtaatatcc aacaacatac tgcattttta aagttctcca gtagttccca   49740
gaatcaaatc aagcaaggct cacccatcgt ctacagtctc acaatctagg acagttcccc   49800 tgccttttttt tggcattgac cgattcatat tgaaccaatt ttatgtcatt ggttgattcc   49860
taatgaacca tttccttgtc tacaagctct tggcttgccc tcttacagtg atgagttgga   49920
gtctctccat gacagcacca gactggaaat tcttaacatg ctttccaggc tcattaacat   49980
tgagatagtc aaaatctaca cgatgtcctc aataattttg agaacaggcc atgaaagaaa   50040
atgttgtgaa aaatgtgttt atggttaatg attcaacaca gttaacagag gtgacttggc   50100
tttctgccct gccctcatgg caacatgcgg cttcccagtt cagcactgtc ctctgctgtt   50160
agggcctggg aattctgaat gagattcagt ccttggagtt gaaaaagtaa tttacctgat   50220
gcttggtggt gtgaatgttt gtgacagttt ttgtgctaat acattttgaa ggacatgttc   50280
tctcaaaata gccccttcca ctttctgaat ccacactcca gttttctttt taacttcagt   50340
gagtggtagt ctatttgacc tgatgtgcag atcttctggc acatacattt ctgctgtctc   50400
ttggcataac aaattggcag tctatcccta tgttatgtac actgtttata ttgaaaattt   50460
gtctttaatt ggtctgatac tacatcatct gctagggcca gtagtttgtc atcagccaat   50520
ttgtacacct gaggccctca acaaacacg tgcttacaat gtttctggca ctatttttaa    50580
agcttgtaag aattaaatga gatagcacaa caaccccatg agggtaagta ccgttaatcc   50640
cataatatgg atgaggaaac tgattcattt agagggatta agcaatttgc ccaataccac   50700
atggctagta agtgacagag ctgggtttta gctctgacac tttgattctg gaacctgcac   50760
atttcatcat tatgtcagat gccctgaaga ggatactgta tatcatctca tctcacatgc   50820
tgtgttcagg caggtgacgt gctgctcaat gctggttttg atgtctttac taaactactg   50880
atctattttt gagatttaaa tctcaaaaca gtgatactag tgagaagtag tccacctttg   50940
ttaatccacc aaatgttccg gttagggaac ctaattttgg taacttcaag gcctctcctg   51000
ctattgggag ctaagcatcc ttcactctgg actctcactt gcttcacttt agaatgagag   51060
ctttttaggg taaaactcag gaagtaggat gactgaaaga aaagcctttc ttctccacag   51120
tagcttatgg ggaaactagt aaattaattg ccattattcc ttgccactaa aggatgagtt   51180
cttatggtag caataaatag acaatagggc tgtgcagacc tccaacaaac tgtcttttct   51240
ggggtcaaaa ggggtctgaa ttaacctctt cttaaattac agctctgtga cacctgcagg   51300
cactcataac aaataagaac accaggccag gcacagtggc tcatgcccgt aatcctaaca   51360
tcttgggagg ctgaggtggg tggattgctt gagctcagga tttcaagacc agcctagaca   51420
gcatggcaaa accccatctc tacaaaaaaa aaaaaaaaat acacaaatta gccaggcgta   51480
```

```
gtggtccatg cttgtagtcc cagatactca ggaggctgag gtggctgact tgagccctgg   51540
gaggtcaagg ctatagtgag ccatgattgc accactgcat tcctgcctgg ctgacggagt   51600
gagaccaata gggcagcaag aaacaaaacc tcaacactga accggaatgt ccatgacata   51660
ctgtaaaaaa agaaacctca aatggacaat aactgtatag tgctagttgt aatgattgtg   51720
cctttttttt tttttttttt tgaaacggag tctcgctctg tcacccagac tggagtgcaa   51780
tggcacgatc tccactcact gcaacctctg cttcccgggt tcaagcgatt ctcctgccca   51840
agcctcctga gtagctggga ttacaggcac acaccaccac gcccggctaa ttttttgtaa   51900
ctttagtaga cgaggtttt ccccatattg gccaggctgc tctggaactc ctgaccttgt   51960
gatctgccca ccttggccaa gaatctctt taagtattca tttgtacttt aaggtaatgc   52020
tcgatctcgc tcttagtaca gctgaattgt ccttcaaaaa gatgatctgg ttatgtttga   52080
cctcttcctc aagggaccaa aaagggaagt tctcagcttt ttatagtatg aggtccctag   52140
aggttttcac tttggggatt taaaaacaag ttcctgtag ctatatggag gaaaaaaaa    52200 aaaaaaccta aagggaaca tggaagaatt ataatgattg gggcatgata attatgtcca    52260 gttttaaaa ctccattctt aaaaatgtct tataatttat aggttaaaaa tttaaatgtt    52320
tagaggaagc aggacaggtt tatgagtctc tgacctggga atggagtggg aggaatagag    52380
aaggtggggt tgcaagagga gaaaggcaga ggaatttcct accgtcttcc tgttttttgt    52440
tgatggttag tgattaatga gacaagctgt tctgtttctc tgggagtctt gactgtcttg    52500
aagaaaaaaa agaaaattta ttgcaaccca atgcagcttc agattttcc tctattttt     52560 tttttcaatt aaaaacgtaa ctgtccctaa tttaggaact gaaattccca aacctcccca    52620
ttcacctatt caggaagaaa tgaaatggaa cctaacatct acatttcttg ggtataaatt    52680
caaaacttta atactatggg gatgaacatg taagcaaatg caactctatc tccccataat    52740
gttggaagaa tctaacttga aaccagacat ttggtttgga tcttggcact ttcttgcatg    52800
gaaatattcc aagaaggtgc attgactctt gatttgatct agaaaactgg gttcttttcca   52860 gagcccaccc aggatggcac ctcatagact aactatggac ttttccatca atactggaaa    52920
acagtttcat ctaatccccg gaccaaaggt gactcggact ccaagtgagc ttcctcaggt    52980
ttgtttgtta atttatccaa tcatccattc actcagcaaa catttatcaa tcatttgcta    53040
tgtatatgcc agacactaca ccagattttg caagcacaga gatacaaaat cccttgcttg    53100
caggaaaacc tttggtttca ataaatgata ggagaggggt tgcaggggta ctatctatga    53160
aagttcaaag gaagcatcta acttagggtg gtaggggatg gggctgagca gaaggatcag    53220
gaaggtgttg gatggcagga ggcttttagc tgagccttga aaaggcaagg ggaggttggc    53280
cgctttgatg gggtgggcta aggactatcc atgcagaaga aagagcaggt attaaaggtg    53340
tcaaggcagg gagttacctc ctttgggaac tacacataaa gaagaatggc tagggcctgg    53400
tgtatgggat tggggtggga aacccaaggc aggaagaaga cagatcccaa gaggtctggt    53460
gtgcatgctg aggggatcag gtgccatctc aatgccatgg ggagtcattg aaggaaaagc    53520
agttagagcc atgggatcca gttcacatat gatcaatcac ccaaacaaag gaaagtttac    53580
tcaacaacat gttttcattt ggacttcatt ttgtcaaagc atgaaagtga tgtcagaaat    53640
agaaatgagt gtattcatgg cacaccacca cacccagcta ttttttgtac ttttttgcaga   53700 gaactcctga cctcaaatga tccacctgcc tcggcctccc aaagtgctgg gattacaggc    53760
gtgagccact gtgtctggcc taaaacacat tttctaagat ttctttactt ctgggccacc    53820
tccacaaaat tttatggttc tgggaacccc tatctgaaaa agcacaggta tcagcaataa    53880
```

```
gtataatgaa cactcactag agggaaagtc attttggttt gggttggtta tggaagcagt   53940
gtcatatgaa aagggctgga ctgtactgca gaaatagaag acccacaaat tgctatggct   54000
tataacagaa aaataaagat ttagatgtca ctcatatgtc cattattgaa cagttgtgac   54060
tctgctccct gtcaccttcc ctccaggacc gaagctgaca gagcaccctc tatccaatca   54120
ttgcctgtct tatgtcagag ggaaggaga tggcaaatca tgcatcagcc cttaaagctc    54180
tgcccagaag tggtacatta ccatttctgc ccacatttca ctggccagag caggtcacat   54240
gatatgcctg agttcattag ggcaccagat gttgggcaac caataataca acccaccact   54300 gaggtctttta ctaagaagat gacctgggcc ttagggaatg gccatgattt acctggtaga  54360
cacagcaggg gagcaaaagg aaaatatgac aatattttta tgaaatcaag acttggccac   54420
atgaaacttt tttttttttt ttttttttg agactgagtc tcgctctgtc acccaggctg    54480
gagtgcagcg gtgcgatctc ggcttactgc aacctccact tcccaggttc aagtgattct   54540
catgcctcag cctcccaagt agctgggatt acacgcacca ccatgcccag ctaatttttg   54600 tattttttagt ggtgacagtt tcactgtgtt agccaggctg gtctcaaact cctgaccaca  54660
agtgatctgc cctcctcagt cttccaaagt gctgggatta caggcatgag ccaccacacc   54720
tggccgtgac acccttagaa aactaacttc aaggcagaat gcttcacagt gacaaatctt   54780
aggatgccac tttatagaaa tattctgaag agagaaaaac ccaggtgagt cagagcagcc   54840
tggggaaact tcttagaacc aggattttgt ggaattcaga ggattttaaa aggcagaaaa   54900
tccaatgaag ccatttttaag ctaaaacaat gtaaataagg tggggctgtg cctagggtac  54960
tagggtgcag aaaggaacct gcctcctgtg ggcgcatttg tgttagcagg tagtgggaaa   55020
ttcgggtgga gggcaggtga tggaggaccc tgaacaccga gggaagactc tggatgttat   55080
gtgccaatat ttatcaagaa aacgcagtcc tggagataca ccaataattt tgaaatgtt    55140 acagtagata ctaattgaaa cctacagtgc gccaggcacc gttaggttag cagtgaacaa   55200
aaccagcaac ctaaacaaaa tggtgaacac accaggcagt gcccttgtgg gttacatttt   55260
ggtgagacag atagtatata gataaacaaa tatacaatct caaagagtga aaaagttgtg   55320
aagaaagatg acacaggatt agagagtgac tagggtgtat atggtggcag tggtggtggt   55380
ggtgcagcca aggggtgggg tggaggacaa gacagctgtg aagactggtg agcatggagg   55440
agtccctggt aacaaccagc gctccacacc ctaccctcag agtgccattg cagggttagc   55500
atactccact gagtaaagct tccttgtcca ggcaatcagt tagaagagcc aggaatgctg   55560
ggcccaaaga ggttggccag agagaaaagt gcaggggaca tggttcccag atccacgcag   55620 aaccctggg gaccactgag ttccacaacc tcaacaaggc ccagggttat actaacacag    55680
caggtggcct catttttagac cccacaccag aatctgtgca acgggaaatt ccagtgcagc   55740
agaagttgga gtcaaatgcc tgcctatttc tcattccatt tgggaagcc taaacaggga    55800 agccttctgt gttcctctca ttcccatatt aaactgaact gcaaaactca tggctctaag   55860
tagactttag aattgaccta ggcagaagaa atagcccagc cccttcatta cttcagagca   55920
gaatagagca cttactctta tcacagcagc acaagacccc tgggacacct gactccctga   55980
gacccttcct tgacaggttc ccctgtccat aaacaaagtc aggaattccc agcccactac   56040
acagaatatg acagttaagc ttcattggga tcctgtggct gacctgggc aggctagagg    56100 gcatcacatc tgtacaggct ctcagctttg cgagttcaga aacagactgg gtgttcatgt   56160
ggactggccc aaacctgaaa ctctacagaa atcgcagtgc atgccaggtg gtttgccatg   56220
aaaaaaggtg tgtgtcccag agacagggtg tgtatggtac aaatggatt tgtccacgtc    56280
```

```
tttccttccc ttgccagtcc agccacccta ctgtcttttt tttttttttgt cagttttttgt   56340 tttttttttaa tttaagttct gggatacgtg tgcagagcat gcaggttcgt tacataggta   56400
tacatgtgcc atggtggttt gctgcacctt atcaacctgt catctaggtt ttaagccctg   56460
catgcattag gtatttgtcc taatgctctc cctcccttg cccccaaccc tccaacaggc    56520
ccaggtgtgt gatgttcccc tccctgtgtc catgtgttct cattgttgaa ctcccactta   56580
tgagtgagaa cgtgcttacc ctactttctt ttcggtttgt ttttttgttt gttttgagac   56640
gagttttgct tttgttgccc aggctgaagt gcaatggtgc aacctccgcc tcctgggttc   56700
aagggattct tcagcctcag cctcccgaat agctgggatt acaggcatgt accaccacgc   56760
ccagctaatt ttgtattttt agtagagaca gggtttcgcg atgttaggca ggctggtctc   56820
aaactcccaa cctcaggtga tccgcctgcc ttggcctccc aaagtgctgg gattacaggt   56880
gtgagccacc acgcccggcc tacctaccct actttcttag cctatttgct gactagcatt   56940
caaactgagt gcagggagaa cacctagcag cctgatccca gaagtgcagc tactccacat   57000
tccacagctc tggggcagag tgactaaggc tcacctgtag tccttaaatg gagagcaatt   57060
tgggatgtac cagctaatca aataaaacca aggcagcaaa caatagccat cacttctcaa   57120
accatcctca ttgtgcccct cgactccctc cttccatttc cagttctccc cagagggggag  57180 acagacaata acctcaacaa cagaagccag tacacagcaa gcttgcttca cacgttcacg   57240
tttcttttgt ttttctttga tgttttttct ttgatgtttt ccattttcca tctctgaggt   57300
gattagcagt acagcatagt ggttaagaac agagcaggga ctccacggat agactaccca   57360
gtcttgtcct ttgttacagt ggttcttaag cttcaggtg actgggaatc acctggagag   57420
cttattaaaa cgtagatttc cagccgcgtg aagtggctca cgcctgtaat cccagcactt   57480
tgggaggcca aggtgggcag atcacttgag gtcaggagtt cgagaccagc ctggccaaca   57540
tggctaaacc ccatctctac taaaaataca aacatgagtt ggccgtggtg gcacacatct   57600
gtagtcccag ctactctgga gactgagaca tgagagtcgt ttgaacccag gaagtggagg   57660
ctgcagtgag ccgcgattac tctaatgcac tccagcctgg gggacaaaac aacaaagcga   57720
gactctgcct caaaaaaaaa cccaaaaaaa caaaacaaca cagattactg ctccccaacc   57780
ccagagtttc tcattcagca catccaggat ggaacacaag gatgtgcagt tctaactagt   57840
tcccaggtga tactgatact cttggtacca tgaccacact ttgagaacct ctgccttatg   57900
aagtttccaa agactgttga cttgtgtgtg aaaggataac cctataccta ccacttgtgg   57960
ctattagggt taaatgagtg aatatacgta aaatgctttg agctgtgaat aataaaatgc   58020
aagcatagct agtctgggaa cttcgcccat gcctttttgc tctgttttgt ttgttaacct   58080
ccatttgttt tgtttgtaat aaaccactta gccaggtacc tcttcctctc cttcaaatac   58140
agagggcgtg tgaactttgg agaatgagtg tttaaactga cctaaataat atgtgatttt   58200
caactcttct gtggattcac tcattattca atgtgggctt tgcgtgccat atgtgataaa   58260
cttcttgtgt gtgggggtata gtgggaatgt gcatacgtga aattgatgtc agatctttgg   58320
atcgttgtta gggaagataa aaggaactca cactacagtg cagccttgcc agtagggctg   58380
ttattcccac ttacgtggaa gaaactgaaa ctcagttcat tgaggaaact ctctcaagct   58440
tggacttagg tcagaggtga cttgtaagga tacacacaga gaaacatcca agcctgggaa   58500
accagctgat ctattactct gtgtaccaga actttatgta tcagaccaaa cacacaacaa   58560
gcctcacgaa aaactggaat gtgcttcaca tcactgcagc tttgtcccaa tgactgggcc   58620
acccaaggtc tctgcttctc cctaggcatg tcccattgag actctccaca tagagatagt   58680
```

```
ctgatggagt tgtgacatta acacccaatg tggaatgtcc cggtggggtg gcctcggatt    58740
cagttgtctt gttctgtaat cagtcatagc caggaagaaa gcccagtctt gctccaggag    58800
caaaccgtag cagcatgctg ctgaaagaac tgcctgggga cttttccccc agagtggggt    58860
tggctttggc ctgtctagta cttcaggga cattgaggca gccttagatc ctcagaagag    58920
cacagatctt tggaatcaga cagacttgga tttgaaccct gtttctgcca cttaagtttc    58980
ctcaactatg cattgtggct atcacacacc tcacaggtgt gaagatcaaa taacataaag    59040
tgcttagcag agtgcctggc acatagtatc tgcacttaat gaatgatagg gtttggtttt    59100
ttttttttta aattaaaaaa actggaaaga tggaaggtg aaaataatta ctcagcttta     59160
tcatcctatc atttagcctc ttatccctga cagtgtgcca ttttcaatcc tgtagggatg    59220
cattcattat tattaattttt ttaagagaca ggtcttgctg tgtcccaggc tggagtgcag   59280
tggcacaatc ataattcact gtaacctcaa actcctggga tcaagggatc cttgcacctc    59340
agtctcctga gtgtaaggtt cttgtattgg ttggaaccct gagagcgcgc caacagaaaa    59400
cacgaggcgg tgtgaagcaa catgctgttt taatgagcac ctgggtacag gcaggctgaa    59460
gcctaaaatg gcatcagccc caagtgagga cagggcagag gttttatagt ctcttgtaaa    59520
caggaagtgt cctagtctga cgtaactgct atgttgtacc caggtggcct gtttctcgat    59580 cagggggtaca tgtcttcgtc cagggtaggt gtcttcctgc cggctctctt cctgcttctg   59640
ctatcttgct gacacacgct gctgacacaa gtggacttgc gccttgggac tgggcctgag   59700
aagggaggag ttattcatct ccttaagctt tcaggccccg gggagaatct tataccgcgt    59760
agctaggatt acagacacat gccaccacac ccagctaatt tttaaagttt tgtagagat    59820 ggcatcacac tgtgttgccc aagctggtct caaactcctg gcctcaagta atcctcccac    59880
ctcagcctcc caaagtgctg ggattacagg catgagccac cacacctggc ctcatccatt    59940
atttaattta aggctttata tgctacgaag ctataggttt ttaatagaaa gtctgtttta    60000
catggttgta attatataat tttgcattct ttttccatac tataaaatat tttaatgtta    60060
taaattctgt acgtaatttt agtgaacatg ctataattta cataaaattc cttatcattg    60120
gacacctaac aatagagaat tgattgaata aatggtagtg cattcatata ataaaatatt    60180
aatcagccat ttaaaaaggt ggattagaag tatacttctt aacatataaa catgttcacg    60240
attatgtata aaatgaaatg agtgtaccta aatatcaact acctctcaag tctgtctgga    60300
cattttccta cctcagtctc agcaactttc aaactttaat gagcctccca atcaccaaag    60360
gaacttgtta aatgccagtt tcacgcttta ccccaagagt ttgactgaga ctggggctca    60420
ggaattggca cttttacaag gatcccaggt gcctctgatg tgggaaagac acctcaccta    60480
tttctgcctg ttgaagctat acttaatttt ccaagcttct ccttcttctt tctcctgaag    60540
tcctgtagta ttttgtagca cttgtctgct ttcttgtctt agagatctta gcaaatgctt    60600
ctaaattgta aaactttcc tgatcctcca accaaaccta gttatgcacc catgtcacag     60660
ccccagaatt tgtgttaaac cctgtgtgag ttgctgaata taaatactga aatctctgga    60720
atccaaactt catttacttt gtggtggaga gagagtggct gagtacttca gaactcttta    60780
gaacacctgt tatagcagga acttttggga ataaaggtgg tctttctaac cttgatttaa    60840
aacaaaaaca aaaacaaaac cttgtttaga ttacttttac ttacctgaca gtcaggttgt   60900
gaaaagtaaa tagtttgtcc tttgtgcatt tgctctggtc taggccagag atagccagta    60960
agctggagag ggcagttaaa acccttcaag aggcctgtca ttccaaagaa tagttttctt    61020
caggtctgtt ggttggtttt cattctcaga ctgtgtcact gaggttgttc aaggtaagat    61080
```

```
tcttatcttg cagttcactt agggaccact tatgctaaaa ttgagactga gttactcatc   61140
aaagtacttc ttcacttaga tttttatcag tgtgatttcc ctccttcttt aaataatatt   61200
ggatatccat atcaagtcag gtttatgtca tcttacatta tcttttatgt aataggccag   61260
cttgcagatg catagttata aataactatt gataaatatt atattgagat gacactgaaa   61320
ttttgtcctt gcttgtaaga gaactagatc atattctgta taattagtta acacaaaaga   61380
attcctcaga aacaaacttt aaaagccagg tataacagct cactcatgaa aagttccttg   61440
tttcatatga aaatggtaac tttgtagaag taaagctcca gacaacaaag aattgacagg   61500
gttggggaat ggaaggttaa tgaaattggt taatcaaatg cttctgatgg ggaatcacca   61560
catgtagtgt acttgtccac atggcaaact cggaatcact cttcagaacc ttgtgtagag   61620
gcatcatcta taaaccctg catctgtaag cttttttcat cagcccctc cttggaaaaa   61680 atttcttttt ttattctatg cccacaacag tacactacac acacatctat catatgtcac   61740
actctagtat atgcttgtgt gttactatta tccaatagat cagaaattca ttgggcatag   61800
agcatgtggc ttatttgtgc aatctgaccc aggttcagtg cctggatata gtagtattca   61860
ttaaatagat gtatgaataa gaattctgca ctgaacaggg tacataaatc atataaactg   61920
cattttgtgg gtgttttctg agaactcctg cagttaaatt taaagcatca ccttatgaca   61980
aatttccata aaatattgtt ataataaatt atgaataaat gttgaaaata acaagcccag   62040
tatctgctgt tccctgagtc cctgatggca actgcatgct ccccagtctg tgggactcct   62100
gatttaaaga gctagatctg aacttctgca gaaacctgct caacatttgc ccattggttg   62160
ctgtgaaatt cctctcctgg gctcttaaat tccacagagg cttaattatt acagatattt   62220
aaactttgta catacatgac ggatatcaaa catacccaca tctctaaggt aaactgtatt   62280
aaaagtgcca gacaatttta aaattgaaag ggacttcgtc attttactg gttaggaaac   62340 caagcctctt aagagacaag cagttttgt tagtgggagg agcactagaa ttgaagtcaa   62400
atagaccaga gttcagttct tggctcaggg gctcaaatca cagcctctga tcggcagtgt   62460
gatcataagc cctttactta atattttga agatcagttt tttcatttgt aaagtttggt   62520
taataatccg tctcagtggg tcacaacaag ggattacttg agattacctg agccagagca   62580
gcacacataa tatctgcaca aagcaaatcc tcagtgagct tttgtctctg ccctttcttg   62640
cccagatcac acagagctaa gacttagacg cttttctttgg gttgtggttc ccagttcacc   62700
tgacaggact cacacatatc aaggatgctc ccaaggggct gtgtcacatc agcatttaaa   62760
tacagaattc aggatctcct gctttaaaaa caatctccct tctgagttac tctttttaaa   62820
ttttatttat ttatttattt attttgaga cggagtctcg ctctgtcgcc agggctggaa   62880
tgcagtggcg cgatcttggc tcactgcaag ctccgcctcc ggggttcaca ccattctcct   62940
gcctcagcct cccgagtagc tgggactaca ggcgcccgcc accacgcccg gctaatttt   63000 tgtatattta gtagagacgg gattcactg tgttagccag gatggtctcg atctcctgac   63060
ctcgtgatct gcccgcctcg gcctcctaga gtgctgggat tacaggcgtg agccaccgtg   63120
cctggccctg agttactttt attgctgttg tttttttttc tttccttgta ctgcgagtta   63180
tgacaccctc ccagtcaacc atcaactata atttaacttt atataattgt gtgaattagc   63240
aagatcctag gaggctccag gatctcaaag gctccaggat ctcagggtaa tgtatataca   63300
cattttagaa gagtaagatc tacatcgcct aataagtctt cagcttttaa aaatcacatt   63360
ctaaaataat aagtgaaata tttgtgctga attgaaaggg tttccataaa ttctgacggt   63420
aaacgatgag tgttttaagc atggagatgt tagtcataca aacttaagtc accatgaaac   63480
```

```
aggcgatcaa gtgggggaag cagcatcctg tttcctagtc ttaccagagt tcatttgtca   63540
ttttaagaga caacttactt ttccatcttt tcttcttttc ctgtaaaggt agaaacctgt   63600
gggttcttgt tgtggggcgg tttccaaagg aacacagaat tgggattcca gagttcaaat   63660
acgtggcaaa tatgcatgga gatgaggtac gtatgtggct tgaatttctg aaatgtcacc   63720
agagaagctt cccctagggt ctcttgagct ctgtataaat gctaccgagg aagcctggag   63780
aagtctccag catgcattgt acaaagaagc aaggcccaga gaggtcttcc tgtgaggcct   63840
gtgggaggtt aaggaatcag ggtccaacaa ccaccacagc tgtatggttg tgtacccagc   63900
accctgtcag agtagctgga gcttgttttg tgtttggggc cggaagaaca acagttcccc   63960
agccctgaac ttctgccagc caatccctgc atctcctttc tgggttaagt tttcccacct   64020
cctggtcagc atgaaggtga cccagcaaag gagctgtatt gtatccgaac ccacaaccat   64080
cagaaactcc caaatagcta cccaaattcc tgagatctgg cttttcaaat gcttttgtta   64140
ctctctctta aatctaacac tcattgtctt cagtgctcca gtttagacaa tcacacttat   64200
gattctctcc tactcaccat tcaacaaaca cttggctggg tgcagtggct cacacctata   64260
atcccagcaa tttgggaggc caaggcaggt agatcacttg aggtcagtag ttcaagacca   64320
gcctggccaa catggtgaaa ccttgtctct actaaaaatg caaaaaatta gccaggtgtg   64380
gtggcgcata cctgtaatct cagctagtcg ggaggctgag gcaggagaat tgcttgaacc   64440
caggaggtgg aggctgcagt gagccaagat cgtgccactg ctctccagcc taggcgacac   64500
agtgagactc catctaaaaa aacaaaacaa aacacaattt taaattcctt aataatatct   64560
tgcctctttt ccaacttagc agggataaac tctccttta tttttaggtt ctacaaaata   64620
ccatttacca ctgttaccta cccagccatt cttgccaggc agttgaagat gttcacctct   64680
gtttctcacc ttgcttcctc agaatatttt gagaccatga caactgaaat attttctgtt   64740
taccaggact ctataaaact gagcgatcaa agagtcccca gccatcccag taaggaaact   64800
ttgcacagga atgtgggtat taccctgtaa aacacaactt ataactttag ggactttctc   64860
atttacatac atattccaat aagtactacc tgctgacttg ttaaaacact tctggatttg   64920
caatagtatg ggtggcatgc tctaatcagt gctgagcttc ctgttctggc ttaagccctc   64980
cccaaactct ataggaactg gatctaccct tcatggtaca ctccgcctgc ccttgccagg   65040
catgctgccc aacctgtcct gctgagagag gatacttctt gcagctgcag ctaagatgca   65100
agcacctgcc cctagcaaag gaataagttt ttgaacccga ttttgggggtg ggtgcaagtt   65160 tagcccatct gtgactttt gagcatcacg ggcggcttct ttaaaaaaga ctacgttgca   65220
aggagtctga ccaaagttag ttttaataaa acaactgttc gttatagaca gcagctcaga   65280
ctgcgtttcc cttttgctat cttgtctatt gatcgaggtc ccttgatcaa ggtccctcag   65340
aatgcttttt tttttttttt tttttttccg atggaatttc gctcttgtct cccaggctgg   65400
agtgcaatgg catgatctcg gctcactgca acctccgcct acaaggttca agcaattctc   65460
ctgcctccgc ctcctgagta gttgggacta caggcatgca ccactatgcc cagctaattt   65520
ttttttgtat ttttttttt ttttagtaga gatgggggtt tcaccatttt ggccaagctg   65580
gtctcgaacc cctgacctca ggtgatccgc ccgcctcagc ctcccaaagt gctgggatta   65640
caggtgtgag ccaccgcgcc tgactcagaa tgcatttgta acaagagaca tatggcattc   65700
attgtcttta gtagtttttt tattgctggc atttcagagg ttccagctat ctactcagaa   65760
attagtcctc agaactgaaa ctcccaaaga taagcaagag tcctttccgt cccctacccc   65820
cgaatttgtt tattctttcc atgcactttc ctaaatttct ggcatcttgt tgtctggtgt   65880
```

```
atcgttcaaa tcagggctcg ctagtgcgct ctgattcttt gagaaatgct gagggctgag   65940
actaggcagc ggggaaaagt cccagtgtat tttggggtgg gaatctgaag cacttttacc   66000
cccttatgtg acccagctcg tggcaatgtc tggggggtct atggggctag taagaaattt   66060
attattctga atttgagacc ttatctattc tgtcctcccc atgccgctag gagctgaaga   66120
aagtgatggc ttaacattgg agcagagaag tccttctgaa tacaggatat aacaaccccc   66180
tttttcctcc catagatctt ttgaaattga aagcatttttt aagaagcaac agagctaaca   66240 tttttagggca gtgattctta acctttttttg gtgtattcct tgctattctg ttataaattt  66300
gacctgactt cagggtctgt ggattaccta ggagtttatg gaccttaggt ggagaatccc   66360
agcagggaac acatacacac tgagtggcag ggtggacaga attggccaca ctattttttaa  66420 aatgggaccc cacccccact gtgcgtgtgt gtgtgtttgt gtgtgtgttt ccacacttaa   66480
tactatggct agatgacagg aagcatcagc tgcatcaggg agactcagct ctgctgatta   66540
cacctgccat tttccccat gtattttttat tttacttatt tatgccttgt tttagaattg   66600 ggtcttttttt taaattagaa attgtctggt ggccaaaaag catatgaaaa agtgtctaac   66660
aacactaatg atcagagaaa tgcaaatcaa aaaccacaat gagatatcat ctcataccag   66720
tcagaatggc tattaataaa aagtcaaaaa ataacagatg ctgatgaggc tgcagagaaa   66780
aaggatcact tacacactgc tggtgagaat gtaaattagt tcatccactg tggaaagcag   66840
tgtggtgatt tctcaaagaa cttgaaacag aactacgatt caacccagca atcccaatat   66900
atacccaaag gaatataaat tggtctgcca taaagacaca ttcacacgta tgttcattgc   66960
agcgctattc acaatagcaa agacataggg ttagtctaga tgcccaccaa tggtagactg   67020
ggtaaagaaa acatggtaca tatacatcgt ggaatactat gcagccatga aaaagaacaa   67080
agatcatgca cttgcttata gaacaagatc tataagcaaa ctaaacagaa aatcaaaaac   67140
cacatgttct cacttataag tgggaactaa acattggata cacatgggca caagaagggg   67200
aacaatagct accagcatct acttgaggat ggagggtggg aggatggtga ggataaaaac   67260
ctacctgtta gatactatgc ttattaactg ggtgatgaaa taatccatac accaaatccc   67320
cacaacacac aatttaccta tagaaccaat ctgcacttgt accctgcac ttgtaacatt   67380 tacctataga accaatctgc acttgtaaca tttatttttta aaataaatgt taaaaaaaaa   67440 aaaaaaaaa aaagcaggcc gggcgtggtg gctcacgcct gtaatcccag cattttggga   67500
ggctgaggtg ggtggatcac ctgagtttag gagttcaaga ccagcctggc caacatggtg   67560
aaaccccatc tctactaaaa atacaaaaaa ttagctgggt gcagttgtgg gtgcctgtaa   67620
tcccagctac ttggtaggct aaggcaggag aatcacttga acccagaagg cagaggttgc   67680
agtgagccaa gatcatgcca ctgcactcca gcctgggcga cagagtgaga ctgtctcaaa   67740
aaaaaaaaaa gaaaaaaaaa ttattacaaa atcaacatat gttcatgtta gaaaagtat    67800 aaacaaaaca ttatatactg accttcccaa aattagtgct cttaatttct tatttgtttt   67860
tccagatatt tgtgtgtgca tgtactttta ccaaaagaga tatgctattt gcaacacttt   67920
taagtaaata ctagctacct ttttgtacca ataaatcttt atcctatctt tatcttatcc   67980
cccactttct agtttctcca attgtcctca aatgtctcta aaattaccca aatcaggatc   68040
cagtcctggc tcatgcatcg catttagtgg atatgttgga tctcttggat ctcatttaat   68100
ccagtatctt tttattatga tactaggctt gataaagagc ccaatcagtt gtctgccctg   68160
tagaatgcca catattctgg attttttggtt tgcttcttta tagtatcact gcagttgtac   68220
ctctagtccc tgactttact tcaaactgga aattaaatct aaaggtttgt tgaatttaat   68280
```

```
gtggctaata cacatcttag gagttgtgac gataggttca tttgattgat gctgagggtt   68340
caggctaatt cacctggcta cactcaggaa tgccaaaagc aaactccggg tagcaaaatc   68400
aacttaaaat ggcccatttt cagccaagta ttgttacaaa ataagtaaag ttaaactcac   68460
tcctcatttt gcatgaattt cacgtattct cttattcttg caaaggtcat tgttctacta   68520
ggatcatggc tcatactgta gatatttttc ttgtcttcag tgaccttcca ttgtctcaca   68580
tgctttctat ggcacaggct cactatgcca cattaatcag gctggcaagt tgcctcctca   68640
aacagtgctt tacaagaaaa taataacaat agctaacatt tatggagcac agatgacaat   68700
aagtgcattt taggcctcgt ttctttggat cacctctgca gaaggcatgt ttattagtcc   68760
catgtaccat gaagggggcc caggtttatg cttggtcacc agctgtggga acccggagcc   68820
tgaacaccaa gctttgccca gctgtggatc cactcctttA ctctctcttc tctgttttta   68880
aaatgttctg ttttatggtt ttcattctta agtatagatc tatgatctat ctcaaattaa   68940
tttcactggg atggatacta agttgttgca gcaccatttg gtgagaggat ttgggcttgc   69000
tgttatgtaa aagagtaaca agctcttgga gggcaacact ggaataagta tcttccagtc   69060
acctacctgt ccctttcttt ccctactct tcacttctct ctccttgact gctggggagc   69120
tgacagacat agcactcgtg gtgagccttt gtcaccgatg tttattcatt ttttggagca   69180
gcatgggaga acatttctg gggttctttc tcattttaat aagactagta ggtgttttc   69240 tggttcatcc aggcacacac attatttgca cacatattgg catgttggat tgaagcctca   69300
attctaggtt taatttacgc aagctcctaa ttggcatcac ttggcatacc tacagttgaa   69360
tctttttttt ttaattggaa gggttgatgc cagtgcaggc tgaatggggt tctctgccat   69420
tcctgtatgc tacagatatt cagattgcct gggaacagga tccttgtccc ctcaccttcc   69480
cccatcacct cattctgctc ctggcttggt gtgtagtaaa ctataaccaa tactctaaaa   69540
tcagagctat actgaaaact gggaccatgc cctgaaacca ggagcatcta acatcctcag   69600
cctaaatgtg gatgcagaag agaagcctgg gaaaatcttc cccagccctc cctactcttt   69660
gttttgtgct tatcttctat cccatgtttt tcaaattttg cagaaaaaat acttttcttg   69720
ggtaatctct aggttggtaa gacatcttta attcctgcct aatggaaata ttgaagcaag   69780
gcatgactgt gtgcttaaag aattgggtgc ccaggccagg catggtggct catacttata   69840
atcccatcac tttgggaggt caagctgggg agattgcttg aggccaggag ttcaagacta   69900
gcctgagaaa catagtaaga ccttgtctct aaaaaaaaat ttaaaaatta gctaggtggg   69960
gtggtgcata cctgtggtcc cagctactca ggaggctgag gtggaaggat tgcttgagcc   70020
tgggaggtcg aggctgcagt gagccatgat cacaccactg tacttcagcc tgggtgacaa   70080
agcaagaccc tgtcttaaaa aaagaattga atgcctagag ttttaagcca accctagtaa   70140
cattaagcaa agtatcatag gtcagagcct gggttcaaac ccaggtttcc ttgacctcag   70200
tgccaagggt cttaaatact gtactgtagg agtaactatt gaatatgctt gtaaaataat   70260
ttaactaaat tgcaattatt ttttatttta gagttgggat ctcgctctgt aacgcaggct   70320
agaatgcatt ggtgtgatca tggctcactg taacctcaaa cacctgggtc caagcaatcc   70380
tcctgcctca gcctcccaca tagctaggtc tagaggtgtg tgccaccaca ccaggctaag   70440
tttttatttt tttgtagaga tggggtccca cagtgttgct cagactgttc tcaaactcct   70500
ggcctcaagc gatcctctgg ctttggcctt ccaaagtgtt gggattacag gcttgagcca   70560
ttgcgcccag cctaaattgc aattctgctt ttttggggag atgggggggta ggaatttttt   70620 taagccttag tttcttaaag agcaatgaag tatttttact aagatagact taatatgggc   70680
```

```
ttttgtaact gcccaacagg ttcattttgc ctgttgtcca gatagagcag atttatcaag    70740 acagggaat tgcgatagag aaagagttta attcatgcaa agccaactaa acaggagacc     70800
ggagttttac tattactcaa gtcagtctcc ccaaaaattc agagactggg agttttttaag   70860 gataattttg tgggttgggg gagagacagt ggggagtggt gattggtcag gtcggagacg   70920
aaatcatagg gtgtcaaagc tgtcctcttg tgctgagtca gttcctgggt gggggccaca    70980
agaccagatg agccagttta tcgatgtggg tggtgccagc agatccatcc agtgcagggt   71040
ctaaaaaata tcttaggttt tacaatagtg atattatccc tctgagcaat tggggaggct   71100
tggaatcttg tggcctctgg ctgcataact cctaagccat aatttctaat cttgtggcta   71160
atttgttagt cctacattca ggaaaaggct attatcatct ttgtttcaaa gttaaactat   71220
gaactatgtt agtttagcct atgcccagga atgaacaagg acagcttgaa ggttagacgc   71280
aagatggagt tggtttcatc agatctcttt cattgccata attttctcac tgttatgatt   71340
tttgcaaagg cagtttcact tttgaaaaat tcgcatcaca tttagaattt tatgattgtg   71400
gcattggttt atagtttatt gtattccaga aatataggtt gaaaagagaa acattccct    71460 gggtaatagt ggccatattt gtcaacctga aaataaagag ataaaggata aatgactttc   71520
acacaccttc taagtataag agacagttga tgagatgtag tttgcatgtc taaatgtttt   71580 acttagggggg tattttaatg gtttacgcag acagtgggac acaatatctg aaattatggc  71640
cgttctggaa aatctgggaa gtacagtcaa catgcagtag aggttcccaa cttatcatta   71700
aaccaaaaca caacattaaa gcttgtcttt ctaaatgccg ctgcccaagc tccttttcct   71760
accactatcc tcaggtgata gtaaaatgtc ctcagtaacg ctctgtggtt tgaataatta   71820 aattcttct ttttagattt aggcagagct cattgttttc caggtgaaat atctaattca    71880
ttttaagcat gttttaaatt aatgaactgt ttggtgacca gatatcccaa gtccctgtca   71940
tgagcgtaat tgttagcctg tgcctctata aaatgtgttc ggtatttaaa aatccttcag   72000
ataaaatagc ttgatcattt gtacatctcc ccttacaaag caccttaagt cctcatgtga   72060
atttcagaaa gttcttcctc aggatagtct tgatcttata atgaattttc aacagtagtt   72120
tattagcaat tatttattga atacatgata taccaggagc tggacaagct acaccaagaa   72180
cacagggata cagagaaaaa ccgtgaaggt ccctgacttc ggggcttcga tggtggagtt   72240
agagaaaggg aggtcagtca aggtcagcca agtgattgta acgtgtgtga cccgcattag   72300
ataacacagg tgtcatggtg aacccagact tgggaggtca agaaaagtat gctagataaa   72360
tgtcatgttt aggctgatat ttgaagaaga aggattagct aggcaggtca gacaaataac   72420
ttaaatctat aacacacaca ccactgtgga gccccacagc ccgatgactt tcccccaga    72480 agctgcatca cagggtagca tttcaaaaac agattccatt gttaggatag ctgaagattc   72540
tctctctctc tctctctcac acacacacac acacacacac acgcatgc gcgtgcacac      72600 acacacacac cacacaacac tgcctgggtt gtagattgtt ccttcaaaaa tttttttctg   72660
ttttttttaa taaacattct gtgaagaacc agaacactca tttgtatctg tgtggcaaat   72720
tccaacttga ctgaattgaa ctgcagctga tagagaatgt attttctgct ttctgggtga   72780
ctgccatttt aaccaccgga tgaaggagat ggagtgagag tctccggagg ccggtgtgtc   72840
catcaggccc ccgtttcttc atgagggctt ctccctgaag tctgtgctct cacaggaagg   72900
aagccagcat gctgggtgaa aggctgcctg ggcaattgga gactcttttg accacattct   72960 ttttaaaat ttggactctc cagggtttcc tgtcaaagac ttaattttca atgaaggag     73020 gtttatacat aaaacatgaa tgagtgtttg aaacatttat attaaggttg ggaagaatta   73080
```

```
atttgaataa tatttggcat aaatctgctg ttacagaggc aggaaaagat ggcccaaaaa   73140
gaaaggagga ttttgtttaa ctgcctctga aatttcatct gtttatctca gcatttaaaa   73200
aattatctga tgcttagttg gttctttatc ttattttcaa gattttatt tacccttgca   73260 attgagaact tgtgatttgt tgtggactat tgagacacac aaaaaatact ttggttacat   73320 acttgttttcc ctgaaagaat catgatttta ttattttttgt aaaaatgaca taggttttct   73380
ttaaaaagaa taagaggaaa taaaaatcat tcagaatact gtacccagaa atagccatca   73440
ttaatatttg tcagacatca ttgtagacat ctatatattt ctgtagtaag agaatgagag   73500
gaattaaaag aatataaaat aaaatgtctc atatgttata ttgtatgaaa ttttatttta   73560
tttgaattaa cagaagaata aaactgaagt gaaactaaaa taactggtga aattgatgct   73620
ttctcaaaat aagaaattga ttatcacatt tgtctttctt tttttttttt ttttgagaca   73680
gagtctcgct gttgcccagg ctagagtgca gtggtataat ctcggctcac tgcaacctcc   73740
aactcccagg ttcaagcgat tctcctgcct cagcctcccg agtagctggg attacaggca   73800
cctgccacta cacctggcta atttttatgt ttttagtaga cagggtttt caccatgctg   73860 gccaggctcg tctcgaactc cctacctcag gcgatctgcc tgcctcagcc ttccaaagtg   73920
ctgggattat aggaatgagc caccgcgccc agcttgatga tcagattttt ctaaagttaa   73980 gaaaaagat tattaaaaaac tttgaaattg tagtcatttt atgtgtatat attttaactt   74040
ttgatagtat tttatgtccc cttactatga aatgtgaagt aattaacact ttgaaaattt   74100
ctccctcaac ttctttttttt tttgaggtgg agtcctgctc tgttgcctag gctggatgga   74160
gtgcaatggc acaatctcgg ctcactgcaa cctctgcttc ccaggttcaa gcgattctcc   74220
tgcctcagcc tcccgagtag ctgggactac aggtgcccac caccatgccc ggctaatttt   74280
tgtattttta gtagagacga ggttttacca tgttgcccag gctggtctcc aactcctgac   74340
ctcaggtgat ctgcccacct cagcctccca aagtgcttgg attacaggca tgagccaccg   74400
tgcccggcct caacttttat attttgttct atacccatac taccaagact gcttaatcta   74460
attctgtatc taacagaata ccaactcaac ctagcctcct aatcatggtt tctttactct   74520
tccttttcac tttctttcgg ttgggtgaat ttcattgcca actcgtgtcg tgattgtttg   74580
catgctggag agtgtatgat tcagatagct aagagacaaa ttcacattta gagtcacatg   74640
gggattctga tatcacttcc tctctgttct tgacttggga ctcagatagg ccagggattt   74700
ttgccgattg aaccatacta tggcctctaa ccagcattta gacatttaag gaactatggg   74760
actcctggtc acttcctcct caccttcctg tacctattcc tccccaaacc cttctgagaa   74820
agcttcttaa accaacgatc ttttttcacat ttttttggtt ttttttcgag atggtgtgtc   74880
tcactctgtc acccaagctg gtggcgcgat ctcggctcat tgcaacctcc gcctcctagg   74940
ttcaagcgat tcttgtgcct gagcctcctg agtagtgggg attacagtca cctgccacca   75000
tgcccagcta atttttgtat ttttagtaga gatgggtttt caccatgttg gccaggctgg   75060
tctcaaactc ctgacttcgg gtgatccacc cacctcggcc tcccaaagtg ctgggattac   75120
aggcttaagc ctcacgcccc agcccctttt cacatttaaa gttactgtca cagttttatg   75180
ttaccagctc ctccccactg gctttagggg aggtcataag tagctcatca aggttacttc   75240
caaaggtgct ggaccttcaa aaacctatta tatcttaaaa ttgaaccca gtggggtgta   75300 caagtgactt ttttggttat tagcttgtaa ggactttttc cagtgacaat tttgactata   75360 aaacaaaaa tctggccggg cgcggtggct cacacagtaa tcccggcact tgggaggct   75420 gaggcaggca gatcacctga ggtcaggagt tcgagaccag cctggccaac atggtgaaac   75480
```

```
cctgtctcta ctaaaaatat caaaattagc cagacatgct ggtgggcacc tgtaatctca    75540
gctacttggg agggtgaggc aggagaattg cttgaatcca ggagacggag gttgtagtga    75600
gccaacatgg tgccactgca ctctagccct gggtgacaga gtgagactct gtctcaaaaa    75660
aaaggtagtg gaagaggaag ataaaaaatg agtaggaaaa aaagttgaag tcaggattgg    75720
acataatctg actctaaatt ttatggttgc ctatgaatct ataattcata tatcccaaat    75780
tttctttctt tcttttttttt ttttttttt gagacagggt ctcactctgt cacccatgct    75840
ggaatgcagt ggtgcgatct cttctcactg ctgcctcaac ctcctgggca gcacaagcga    75900
tcctcctacc tcagcctcct gagtagttgg ggccataggt ctgtgtcacc atgcctggct    75960
aatttcttat tttatgtagt gatgggatct cgctatattg cccaggctgg tctcaaactc    76020
ctgggctccg ccttagcctc ccaaagtgct gagattacag gcatgagcca ctgccaccag    76080
ccccaaattt tcttagtccc aatttcaatt attctgtgtt cattaggata acaaatgttt    76140
aaaatgtggt ctctttatgt gccagtgagg gaatcaagtg agaagtggtc atccaaggac    76200
cgcttatcct ttgtcacaat gttgaagtcc tacagtgaaa tcatgactgg aaattcttct    76260
gaggctccat gaaatctttt cttgcacagt gtctacatga atgtgcctgc agcactctcc    76320
tgattttctc acctgctgcc cctgagttct catttactaa cccctcaaca acatctgttc    76380
ttctgaagca gattccttga acctaaaatg atagggagaa tttgatgtag tctaagcaga    76440
tcttcctatg ataaggctga catttaaatt acttttttta aataagaaaa ataatgactc    76500
tctctcctgg ggagggatta taaagcaagt tctctcacag gccttcagtt tcccaagcct    76560
tattgatact gcaagctaat ttaggtggat atgacagctt ttaacatttt aatagtcatg    76620
cttttactta atatatatta gaaatatata tctagaaaag tgataatgat atgaagtttc    76680
tcaggagttg gaagccagcc ttagcaacat agcaagaccc tgtcttaaaa aaaaaaaaat    76740
ctacaatgtg atgattttaa gtctgttatc caccaataca tacatgataa gcttcatatg    76800
caccatgcat tctcatggaa atacgtgatt cctgtgcttc tctgtaactc aacctcttgc    76860
tctcccactc cagaagatac tttggaaggc aaccaaatga aaaatgttgt aagaatcatt    76920
attgcggccg ggcgcagtgt ctcatgcctg taatcccagc actttgggtg tctgaggcag    76980
gtggatcact tgaggttagg agttcaagac cagcctggcc aacatagtga aaccccatct    77040
ctactaaaaa tacaagaatt agctgggcgt ggtggcacac gcctgtaatc ccagctactc    77100
aggaagctga ggcaagagaa tcgcttgaac ccaggaggcg gaggttgcaa tgagccaaga    77160
tcgcgccaat gcactccagc ctgggtgacg gagttgagac tgtctcaaaa aaaaaaaaa    77220 aaaaaggaag cagcagcagc agcagcatta ttccactcta attcatttt gcaatatgta    77280 aactatttac aaataggtac tttcactctt actagcattt tcagcatac ctcaggactg    77340 atcgccacct gatggccact tggcagagca taagcatgct tgagaaagag tgatcttaca    77400
aactagtttg ggtctgagat atcatgtgta gagacccta ttggggaatt tgtaccgtag    77460
ggagtgcttt ccttattgcc tctgacctaa taatgtcctc ttttctcttt aacacatata    77520
gactgttggg cgggagctgc tgctccatct gattgactat ctcgtaacca gtgatggcaa    77580
agaccctgaa atcacaaatc tgatcaatag taccccggata cacatcatgc cttccatgaa    77640
cccagatgga tttgaagccg tcaaaaagcc tgactgttat tacagcatcg gaaggtaaag    77700
aggggctggt ctatctttac ttgaaaacaa cacaacacaa aggctcccga caggcacctg    77760
ttggccttgg caagaggaga tgtgtcatgg tgagagccct cagagccggt gtcatgtcgc    77820
tgatgtgcca aagctcaagg cacatcaggg ctgcctccgg cttgcaggaa gaaatgcaaa    77880
```

```
taaggctact tgccccggt gcccacctag cctctccatc ttcatttgcc actccttctc   77940
tctcccctgc ctcctcccct ctaggcctcc ttcctggaag taccaggtgc tttcttacct   78000
cagcatttta cacacaccgt ttccctgcct aaatagcatt tcctccaaga ctctttctct   78060
cgacctgtca tacactagat cccctgataa actctcacat cacctggcac tttactgtca   78120
gagcacaact tttaatatct aatttcttgc ttcatgtctc tcccccact acactgcaag    78180 ctacctgcag gcaggaatcc tgtccattgt gtttgtcgtt gttagatccg cagtgcctgg   78240
cagagcaccc aggcccttgg taatgaccgg ttgatttatt aggccagtag tccaagaact   78300
aaccataagc aagaacgggt cttgaaggag ctctgattta aacagtttat tttgtttcaa   78360
gctgccttgg gaggtttgga atttctcaga tgtctaatat acattcatat gtatgcaatt   78420
tacatatatg tgtttgcttt accaaagctg aacaaaatct caccacttga ttccctccaa   78480 tttaagttt ttcaaatata tttaaacatg gctgttccac gtttcacaag tacttctgtg    78540
taatgtgttt agtgttgttt ctgttatcag ttgctactta acgaaccacc ccaaaattag   78600
cgacttaaag caacagcctt tttatttact gttgattcca taggtcagga atttgggcag   78660
ggcagagcag ggatggctac tgtccgtgcc acaggtctgg ggctcagctc tggtctttct   78720
gagacaattt acctggagcc atggactctc cgtggactct ccacgtggcg accattggga   78780
tctcaaggtc ccaaaaggga gcatctaaga gcagaagtcc caaatacaaa cacttatcaa   78840
acctctgcct gcatcacaat agctagtatc tcattggtga gagcagatca cgaggcaggg   78900
gatgccatgg gatgtaagtg ccaggtgtgg gtcatggcag ccacaaggg cagccatcca    78960 ccacacccat actcacgttt ggaaagacac ctggagccta aaccaagggg caagacactg   79020
taagaatcca ctcccctcatg ccctatcaat aagccctaaa atattctttc ttttaaaggg  79080
aaaattataa ccagtatgac ttgaatcgaa atttccccga tgcttttgaa tataataatg   79140
tctcaaggca gcctgaaact gtggcagtca tgaagtggct gaaaacagag acgtttgtcc   79200
tctctgcaaa cctccatggt ggtgccctcg tggccagtta cccatttgat aatggtgttc   79260
aaggtaagca ggtgcgggtc cagttctggc ttcttaagtc cagagtgggg ctgaaaactc   79320
tctgcctctg gatggggatc agctctccct tcccctctta acttctctgg cagggtgaaa   79380
agagcttcat gttcccaact ctagccatcc ttcctgtgat tcttcaacag cagatgggca   79440
gtgtggctga actgacaacc cacagctgga catgcatcag tgaattagtg aaatttagat   79500
tctagaaaat acaatctaaa tagtcagatt ttgattctct gacaagagac aacatggcta   79560
aaataacata aaactggaac aactcacttt tttttttgct aatcatatat gaacaataat   79620
tgttgactct tcttaaaact ctgtgggatg aggacccaaa atattacagt agctttattc   79680 accctataa tacctaaga aattgtcctt acctccagaa attagcaaga gtgactgaga     79740
ggacacttaa ttttaagct gatttaggag tttggatttg tatctgactt atttgggggc    79800
tatcaccttg catatgttta ttataaagta gaaagaagaa tagaggaggt ggatgaagga   79860
tttctctcta gggaaattag agcatgtgtg tgtgatgcga ttatgtcttt gctaatatgg   79920
tgtttgtgtt tcctcttact ctcaagtcag tttaaaggtc ttggttcatc ttttaaatgc   79980
agcaactggg gcattatact cccgaagctt aacgcctgat gatgatgttt ttcaatatct   80040
tgcacatacc tatgcttcaa gaatcccaa catgaagaaa ggagacgagt gtaaaacaa     80100 aatgaacttt cctaatggtg ttacaaatgg atactcttgg tatccactcc aaggtgagtt   80160
tctcttcatt tcttccattc tccttattgc cttacccag aagtgccagc tggtttattt    80220
tgatccagca gttgttaaaa gaactttagg cacaataggc ccttcactct gtccttatca   80280
```

```
gctaatatca taagagcagt ggagatgact gattgtttga gagatgctca gacatgttcc    80340
tcattaccaa gggccttctt cattcattca ggtacttatt ctgtgtctgc ctactgtgag    80400
ccaggaactg aaagatgaac aagacacaca cctcaccctg gagttgaata ggggagacag    80460
acacgcagat aagtaattgt gatagcagtg caattagaat aaaaacagat ttagagaagg    80520
tgcagtgtac cccaagggtg cacagagcca aaatacaata gggagtagtg aagagcttgg    80580
agaaatgtga tgcttacatc ccatctaaca gggacagctg ctactagatc tagctaatta    80640
ttgtcatgca gccttgggga gccaatactg ccagatcttg cagtttgtaa agagaagctg    80700
aatttgtaca tgaagtatca tgattttaaa gccattttgc gggctcaaca aaagagctct    80760
tcagacagga tacagtggga ggagggcccc cagttctcca atcttggaat aagacagccg    80820
ggtaagggac aggatgagat tgtcatgtag gcaacatgga aggagagata ttcttattag    80880
agggaataat ataaacagaa acccggggta ggagggacct agggtggaag acaggagga    80940 gagacggact ggaactggat ttccatgcct caggggaaaa cattcccttt tagactcgtt    81000
agcctgaccc caccaacagc aagttgcggc atgcatttct gcgtgcaggc cacttccaaa    81060
ggtgccttcc ctaattgtca ctttggatgc acaggctttc aggtaatctt tcacaagctg    81120 gtattttat gcctgggtgg ctctctgtca gttttcctgg taatataaat aagcatagac     81180
cacaactgat aggcaacagg tccaggcagc attccaaacc tctctctggt gtccaagata    81240 cagcccctc tcctacctta gggcttctgc atcgtccctg ctctccacaa tttgtagcta     81300
agaaagggcc catcctgtcc agtggcagag ctgtccttca tgttcactgt ctaactttcg    81360
aaggcaaatc cagatgtgta ggaaattagc tagaaacggt tgctgctggg aattgttccc    81420
cagtgtgcct gtgtgtgagc tgtgtatcct tctcagacaa aaaacaggtg aagccagctg    81480
ccttgaggag cccagaagaa tgtgcctggc ctggcctgga tgttttgttg gccaggcctg    81540
acccgcctta tccagaactg cccccctccac gcttggcatt tcagttctg gctatctgct     81600 agggatccat aatgcctgcc tgttttgcta tttaaaacaa acccctttgaa agtaagggac    81660 cagaggagag aactggaaag tcagcatgag cagtggcagc ctgggctcca caggggccg     81720 ggccgttcac ctctgagagg cagtgcagca ctctttcttt gatccccagg agcactctgg    81780
catattgggg aagcccacag gtgctggcgg aaggtggcct gcactccagt gtctgtcatt    81840
tactggccaa aacccctgag cacttttctt taacatctgt gatcatgttt cctcatctgt    81900
aaagtagggg caattgctgt gaggattaaa tgagctgata caaagcactt catatggtac    81960
ctggcaatag tgaatgttgg cccatgattc ccccaaatta gcatgcttag ctttgcttag    82020
taagtgtatt tataaatgat ttgtagaaat attttaaagg aatcttattc tagcttatat    82080
ccatgtaaaa tgtaatttaa gaaagaaatg aaattcaaag aatcattttt gtaatgtagg    82140
atttcaaaaa ataaaaacaa aaaaggaccc ttccttcacc cgtcacttaa ttttgatgca    82200
cagttgaact tcagtcagct ctgatccagt tacccatatg gaatattta ggattgtcta     82260 gtcacgcctg ggtaatagaa tgtcaagccc tgattttaca agctaatatg tcaaattcat    82320
tttttcctgt ttacatgtag ctgtctgatt catttgtccc cgaggcacgt gatacttggc    82380
tccactccaa ttttagaccc taacaaaaat taaatatgct tgtgtttagg tggaatgcaa    82440
gattacaact acatctgggc ccagtgtttt gaaattacgt tggagctgtc atgctgtaaa    82500
tatcctcgtg aggagaagct tccatccttt tggaataata acaaagcctc attaattgaa    82560
tatataaagc aggtgcacct aggtttgtaa aattttctta ttaattccct attaatacaa    82620
aatagagcat ctggcaagac ctctgggttg actaaacgca agcctttatt tatgctttgt    82680
```

```
agttatagcc tcatttcagt gccagatctg atggttaaga attctctctg catgagtatc    82740
tgcagtgtgt gagaaatgca gtgcccactc attcatagaa aaggaagcat gatgcatgtt    82800
cctttaatat gagggtataa aaatccagag taccaggtgg tcgtggtggc tcatgcctgt    82860
aatcccagca ctttgggagg ccgaggcagg tgtatcacct gaggtcagga gttcgagacc    82920
agcctggcca acaaggcgaa acctcatctc tactgaaaat acaaaaatta gccaggcgtg    82980
gtggcacacg cctgtagtcc cagttacttg ggaggctgag gcaggagaat cacttgaacc    83040
cgggaggcag aagttgctcc ctccgccaag gagccaagat ggtgccaatg tactccagac    83100
tgggtgacag agtaagactc catctcaaaa acaaacaaac aaacaaacaa acatccagag    83160 tcccctaat tttacatgtt gaatgatcta gaaatctggc aaaatatcag gaaaataggc    83220
tgctactctg ttacatcatc tcccatttag aaaaatacta tgtttgcttg tcactcacca    83280
cgcagtacca aggaccctga gaacactgga cataccactt tgcattttt ccagaattgg    83340 ggtggtgagc tagcaccatt accttcaacc cctctcacct ccgaactctg ccagatgtcc    83400
tggtgctaga atcttgcca gcctgtttgc tgaaggctgg ctggcccta tcacagatag    83460 acagactaaa tgtggcagag agtgatagct ttcaaacgtg cagtggactc accgggagcg    83520
cttgctaaaa cagattgcca ggccccaacc cggagtttct gtttggacca ccttaccacg    83580
tgatgctgat gctgctggtc cagcggctat acttagaaag ccattgcact agagaaacac    83640
actgctagag atgatgatgg aatcttgtac agttcaagtt tattaaccag gtggtgtctc    83700
tttgggcaag gtgtggaagg ctcttctata tttacagagg tgaagttatc tttctccatt    83760
cagaatggct tggggagaga aacatatcag gaattggcat aatagctatg ataccacatg    83820
gagagagaga gagagagagt gtgagtgtgt gtgtgtgtgg gtgtgtgtgg gtgttgaaaa    83880
ggtttgctgc atgggcctac tgcataactg cataattccc ggaattttct gcatgattca    83940
cagcaaagct ttcctcctgc tacaaagaag atggagaagg atgagggaag gtagcacagg    84000
gccagagggc tgagtgcaag gatgattagg acccttcctc ggcacacatc cctaaagggg    84060
atgcccctgc cctctttcat acctgtatcc ccagcctcca tgccctgacc tgaagagaag    84120
tacacaaaga ttactggtaa actcacaggg ctatgtctaa ctggctgagt cgttcatgga    84180
ctaggttgac tccctgtgat aggggatgtt atgaaatatc gttctttctc accagcatct    84240
taataaagat tataaactta ttattgggac tttcaccttc ttcattatgt catcaaacgt    84300
tgtcttgggt tctctcttgc ttagtattct ggtaattctt tctccactag attttcctca    84360
tgaggcatgt catgtattag tctaacattt ctattatatt tctacctcta ttgatccttt    84420
agtttgttaa tctattacta ttattatcat tatcatcatt ttagagacag ggtctcactc    84480
tgtcacccag gctggagtac agtggcacag tcattgccca ctgtaccttg aactcctggg    84540
ctcaagtgat ccttctgcct cagtgtccca agtaagtagg actacaggtg cacagcacca    84600
catccagcta atttttaaa caatttata tagagacaga atcttgctat gttgtccagg    84660
tgagtcccaa actcctgggc tcaagcgatc cttctgcctc agcctcccaa agtgctggga    84720
tcccaggtgt gagccaccgt gactggctct gcctatcctt ttctgaaatt cattcttcac    84780
cagtatcaac atgggtatgg gcgtgcaagt gaacatcaaa tatgctctgt gtaactgcac    84840
tactattttc agaacctcaa tctagctgta aagattattt accaagcact gaattaaggt    84900
gggctttgaa gtatcatgtt gatgtaatat tgccagggaa agggcaatat aaattgcagt    84960
atacctatta ttatttttaa taatttggaa ggcttaccag tccatttgca ctaggttttg    85020 ttttttttgtt tttgagacgg agtctcgctc tgtcatctag gctggagtgc aatggtgtga    85080
```

```
tgatctcggc tcactgtaac ctccgcctcc caggttcatg tgattctccc actcagcctc   85140
ccaatttgct ggaattacag acacccacca tcatgcccgg ctaattttgt attttttgtag  85200 agacagggtt tcaccatatt gcccaggctg gtcttgaact cctgacctca ggtgatccgc   85260
cggcctcggc ctcccagagt gctgggatta caggcatgag ccaccatgcc cagcccattt   85320
gcattaggtt ttataaagaa tgtgtatctg cctgtctcta taatcagatg caaacaactc   85380
actcaaaaaa tacatatatt ggcacatcaa ccctgccccc ttgtggttta agacagatgc   85440
ataacatggt ttaataatga aaccatattt caaaatacca atacagtgtg gttattacta   85500
cttaatagaa aggttctctc cctactagtg cccaataaga aactaatgaa tattttgttt   85560
gtgaagaatg gcagcaaaca ccctttatt ggtattgctc tggtttaaag acattattga    85620
tattcgtcaa actgcattgc atttactggt tccattttac caattgctag gatgcttctg   85680
agtttctgag gttttgaccc atctggaagt ctctgagcca ccttgtctgg aaggaaagg    85740 ccttctgctt tagtggaagg gccttgccaa gagggtagag gctaggtag agcccaagct    85800 gttttgtcat ctggcgatgt ttgcaatctt gagcaagcac ttgtctgaat ctcagtgtag   85860
tcaacagaaa gttgagagta atagcatcag ccttgcctcc caccagcctg ttctaaggct   85920
tcagtggtgt tattccttca attagaactc actgcagacc tcaactgaaa ctcgggcccc   85980
ttggtgctgt gttgtcctgc ttagaggatg atttactagg ttcaagttga gatgagggtg   86040
tcggcagaca ttaaaaccaa agtagcaaag gagggcaagt ctgaattcta gaggcttaaa   86100
atgtcttgct tgtcccggtc tctgaggaga agcaaagatg agccagacac ggtgttacct   86160
gcctgctgcg gccctgtctt tcccctggac tcctcaaagc agatctgaac ctagagagca   86220
agggaatggc tcacagcatc cagaaaccta agcaacctgg gcataaaaga atctggtatg   86280
tgctgagttc cagaagcctg tgagccacag atgtggatct gttatcacat ccaaaatagg   86340
aggcaactgt gaccatgcgg tggggacatg ggcacaaaca agcagtctcc taagtactgt   86400
cccagctccg actctaaatt gtggccaaca gatgcagaat tctagtgctt gcccagccaa   86460
gacttttcat tcatgaagct ctaatccatt tccaagggaa aaagagcttt acatttctcc   86520
catgtatctc cccatctggc cacagaattt atatctcaga ttttatgtct tctcatttgt   86580
attgtatctg agcattttc aaattttcct ttttttttt ttaatatagt gttggctctc     86640
tctgcgtctc ttagggtcta ccagtctttt tttcaatgtt tcaacttcag catatagaaa   86700
taaatcacat tttctggtaa aacaattact tccctcttaa gtaaaaggtt tggtggtatg   86760
tagacaaaat attgtaaaga catatacaag ctaaagcacg cttttatttg gctggtggga   86820
ggggttttcc tttgaatata aattccatac ataagcatgg tctgtgtttg cccagtaaca   86880
gtgatattcg catacccag gcttccatag ctggaagaac catctttagg tttaggtaag    86940
agtcatatga aagtgagtct ttgggcctgt aatcccagca ctttgggagg ccaaggtggg   87000
cggatcactt gagatcagga gttcgagacc agcctggcca acgtggtgaa acccatctct   87060
actaaaaata caaaaattag ccaggtgtgg tggtgggcac ctgtaatccc agctacttgg   87120
ggtgctgagg caggagaatc gcttgaaccc gggagatgaa agttgcagtg agccgaactg   87180
gtgccactgc actccagcct gggcaacaga gggagacttc aatttaaaaa aaagaaagt   87240 gaatctttgg gttattaggg gatgacgaat gagggtcaaa ctggaatatg aagattttca   87300
gacatttctt caaatgcaaa ttgttcttcc ttttctatc tttgagggta ggcagaccgc    87360
aggttgactg gagccttgat tcagctgcag cacacactga tacgtaggtg ttgttcaagt   87420
ccctgaggcc atccaaaatc actgtcatgt gactgtcaaa aaagtcaaat ctgttctatt   87480
```

```
aaagtgtaac tgcttctagc caagaagaaa tttgctgcct ttttttaaag ggtaccatga   87540
cttttttttt tttttttttt tttttttggt gtcttctgcc aactactcat tactagtacc   87600
ctgaattcta tttcatcatt atctccaatg ttaaagaatg gtgtaatgtt agccgggcgc   87660
gatggctcac gcctgtaatc ccagcacttt gggaggctga ggcgggcgga tcatttgagg   87720
tcaggagttc aagaccagcc tgaccaacat ggagaaaccc tgtctctact aaaaatacaa   87780
aataagatgg gcgtgatggt gcgtgcctgt aatcccagct acttaggagg ctgaggcagg   87840
agattgcttg aacccgggag gcagaggttg cagtgagctg agatcgcgcc attgcagcct   87900
gggcaacaac agcaaaattc catctcaaaa aaaaaaacaa aaaattgtgt aatgtcagtt   87960
tcaatgatag ctctgcttca tttttatgc acttgatttt cttcgatttg gttggttttg   88020
gggaagtcaa caaaaaatac aaaagatgcc aacagacaca acaccatcca gcacaagtta   88080
ccttgctgaa acgcatggat tttctaagtg gcatgaagac tgtaaactag ctcagagccc   88140
tggaaaagga ataatatgc atagcttctt ccctcacata ttcctgcttt gtggaacaaa    88200
gttgaattaa gactccagaa attcatctaa tatattctcc ccccgccaca ccacatagtt   88260
tttcttaatc caaataagag gaaaggaaag aaagccaggc ctggtggctc acacctataa   88320 tcccctgcact ccagcacttt gggaggccaa ggtagatcat gtgagctcag gagttcaaga  88380
ctagcctgtg caacatggcg aaaccccacc tctacaaaaa aatacaaaaa ttagccaggt   88440
gtggtggtgt gtgcctgtag tcccacctac ttgggaggct gaggtgggag gactgcttga   88500
gcatgggaag tcaaggctgc agtaagccct gatcacacca ctgcactcca gcctgggtga   88560
cagagcaaga ccctgtctaa aaaaaaaaaa agaagaagaa aggaaagcaa gaattaatgt   88620
ttgttgatcc tcctgttctg tgttacttac atttaatctt cacaaccatc ctgggtggtg   88680
gtatattatc cccatttcat aggtgataaa attgaggctt gggaatgttc agtgacttga   88740
gaactagaat tcaaatcaaa acctgactag gttctttctg tcacaccaag ctatgatgat   88800
gggtacacgc tatatttatc acatatcaaa ggacctccta aggggggcac agtgtaaata   88860
gctcttcaaa ataatgccat tgaagctgag tgtggtgcct cacacctgta atcccagcac   88920
tttgggaagc ttaggcaggt ggattgcttg agcccaggag ttcaagacaa gcctgggcaa   88980
catggtgaaa ccccatctct acaaaaagtt aattaattaa ttaaataaaa caaaataatg   89040
ccactgaaac ccaaggaata aatgcgtaat caggttacca aattattacc aatttatgat   89100
tgggtactac ctaaacatca aaaggatatg tatcaagcag taggaataaa tataaatgga   89160
actgtgttta aaaagagag ggcaaagagg aacacacgaa gtgaaaatag aagtttacac    89220
agttgtatag agaaagggag aaggaaatgt ggcattttcc tcctcaggag acaaaaaatg   89280
aagagtcagg aactaaatag gacagaaagt ataataaaag gcaacctagg tcagatagaa   89340
gtttgttgaa gttcaagata aacattgttt tgctaaatgc caaaattttt atttttcact   89400
ttaaccgttt ctgggggaaa ctgttacgtg tgcctcgtat ttttctgccc taataaataa   89460
ttattgagca taactgtttg gggagagttc aagatcatct tactattgta gctcttcatt   89520
ctcatttatg ttattgggga cttaggcagc ttcaccttaa ggtaatatga tttgacgctg   89580
gagtaaacaa actagatgtg acacgtagga tctaaaataa gaaaggtctt aaaatataaa   89640 tggctttta aaaattgtac tcctgaaatt ttgagagggg ctgtcgagac tatcatgggt    89700
tgacggctag gctgggccac ttcgttggct gtgtgagttt gaggaggtta ttttaataag   89760
ccagagcctt agttttttc atctgtaaaa tcatgataat aattgatgac acagagctga    89820
tatgagaatt taatgagaaa atgctcattt ggtagttagt acagagcctg gaatatacta   89880
```

```
agtgctcaat aaatattggc tgctgttact ggccaatcga ttccatgctt ccaagaagcc    89940
ttgtgattat aattttgctt cccatgtagt tgcactacaa gacaaaacta ttgagtccct    90000
cgcacacgta aatattttgt tgtaactaat acattgacac cgtttttatt taggatttta    90060
tggaatccac caatggttgt agtacagttt ggtgactgag taaataactt ggaagtgaca    90120
ggaatggatc ttaggttgtc atctgtgttc tctcactgtg ataatacgta ctaatataaa    90180
tgggctattc aacaacgaac aaatttaagc tataaatcag attagtaatt ttgactgtat    90240
tttaagttac atcaaaaata agttttttcc ctctctaaca cttaatatta actcacaaca    90300
ttgagttagc taataaatat tgcatatatt gttcttaaat atttataata atttttatat    90360
gccataaaat atggtattaa tatttaattt tattttgtc ttgcaggtgt aaagggtcaa    90420 gttttgatc agaatggaaa tccattaccc aatgtaattg tggaagtcca agacagaaaa    90480
catatctgcc cctatagaac caacaaatat ggagagtatt atctccttct cttgcctggg    90540
tcttatataa taaatgtaag tatgcaatgc tagttattgt tattaaaata ttatagaact    90600
cataatactt attcacccag aaggaatcca aaataagtct aggaagttca aaagtagatc    90660
catcgagaca gaaagaaagg atagtgtcag acttgcaatt ggcaggaggt ggaagaggtg    90720
gaaattatat gaaaaaaaaa aaaccacaa aaattcatat tttttccctg atggcaattt    90780
ttaaaaaatg gaagccaaat cctatctctt gtgatatctt ttatgattaa aatgtaaccc    90840
gattaataat aaagaataag caatgtagca aaggtagttt atagtttccc aggatacgac    90900
acaacaccca ttccacggca tacactttct actataaaaa atgaattgga taagttcct    90960 tagaattcat tttataagtg aaatctgatc cacaaatttt aacactatat tcagcaaatg    91020
ataaacatat tttgcagccc ttttttcatc gatgcaagta aaatttcagt ctttaattcc    91080
ataaaatata tatttctgag tcattttatc cgaagacagg aaggcatgga ctaatttgag    91140
cctgagtgga tttatgtgaa agaactaaat gaataagtat tgatatagtt ggccagattt    91200
tgcctctttc tctttgatgt gaatttctct gagaaattca ggattcttct attttgctta    91260
gtggggctta tgccaaccat agcagtcatt ctatatagag ctaatcctgg gagaaggtag    91320
tcatctcttc tgtagtgaaa actgagttgg tattttatta tttcatcttg aggacatcat    91380
ggaaaaaaca tggttttag tttataaaac tatagaattc agagcctcca tgctccatgg    91440
gttctcccca aggtgcctag atgtgaggct tatcaattgc taatccttt aggaatttct    91500 actcctgccg agaaaatgga tagagcttga aaaatctcaa ctcactgtga atctttgtct    91560
aaaaaggccc tttattttcc tcctatttac tgtgatattt ctattctatt taaaaatatg    91620
attttccctg tagtgaatct aaacttatat gcaacctcat aaataagcca cacctttaga    91680
ataaagttat gaattgttca tttcccatta gttagactaa cacagtacac attgacccta    91740
gatattagtt ctaggataat atttgaaggt aagactctgg acattgaaat gaatgtgtaa    91800
aatacatacc aatgagtggt tatgtaaatg tcattcccca ttttttccct tctccaccat    91860
atataataaa agcatttctc agtagacatt gcctgtagtt agtttagcat ttgtcttgtc    91920
ctgatcattt cctccactaa aaaaaaaag aaagcctaac caaagattca ggctgatatg    91980
aacaaaacca ggtaaaatca aagcttttaa aggagggtgg atgtggtggc tcatgactgt    92040
aatctcagca ctttgggagg ctgagaggca ggtggatcac ttgaggtcag gagttcaaga    92100
ccagcctggc caatgtggtg aaaccctgtc tctactaaaa atacaaaaaa ttacctgggc    92160
atggtggtat gcacctgtaa tcccagctac ttgggaggct gaggtaggag aatcgcttga    92220
acccgggagg cggaggttgc aatgagccaa gattgagcca ctgtactcca ggctgggtga    92280
```

```
cagagcaaga ctctatctca aaaaaaaaaa aagaaaaaag aaaagaaaga aagaaaagct  92340
tttaaaagaa gcaataggct tgtaggtcag ctgaaaagaa attagtaagt tgagaaaata  92400
attctacttg aaaataatct tgatatccaa ggaggatgtt aaatacacac ttgggacaaa  92460
gggaaagagt tatctcttta cccttctgcc ccacgaaaag gatggtggca gaaacatctg  92520
ctgcttcctt ctcttgactt acattgccag atgaggtacc catctgtcct tatttcattt  92580
tgtaattctt ggcaacagca ttcacaacgc tggtctctgt caacaggcat tggataactc  92640
agcctgcagg accaaatctg ttgctggccc agaggtctgg tagattgtta catgcattgc  92700
acaaaggctg cattttagtg atggatatca gtgttttcag tgtgggcacc acgaaccatc  92760
ttaagtcact catataattg tctcttgttt cttctcaggt tacagtccct ggacatgatc  92820
cacacatcac aaaggtgatt attccggaga atcccagaa cttcagtgct cttaaaaagg  92880
atattctact tccattccaa gggcaattgg attctatccc agtatcaaat ccttcatgcc  92940
caatgattcc tctatacaga aatttgccag accactcagc tgcaacaaag cctagtttgt  93000
tcttattttt agtgagtctt ttgcacatat tcttcaaata aagtaaaatg tgaaactcaa  93060
cccacatcac cacctggaat cagggattgc tcactccagg ttactgcaac cctaactcac  93120
tctagtggga ccttgactgg agaaactcca cgatcttcct gaagaagaga atggatgtt  93180 tccaaattcc acaataagca atatgtggtg ataatgaaaa gaatgattca gtcttgacgg  93240
tgaatggaag acacttacct aacaagtact gctcatttac actcaaatta atcttgaagt  93300
agtcttaaaa tgtgtaagaa gttaaaactt gagaagcaaa aaaatgcctg caaaagaag  93360 atcattttgt atacagagaa ccggatgaat ataagcaatg aagatgaaca tttattgatc  93420
ttctacatac aagacttcac cataaggcca ggagcagtgg ctcacacctt gtaatcccag  93480
cactttggga ggccaaggtg gcggatcac cctgaggtta ggagttcaaa accagcctga  93540
ccaacatggt gaaaccctgt ctctactaaa tattagcggg gtgtggtggc gggcacctgt  93600
aatcgcagcc tttcaggagg ctgagacagg agaatcgctt gaaccctaga ggcggagttt  93660
gcagtgagcc gagatagtgc cattgtactc cagcttgggc aacagagtaa gactctgtct  93720
caaaaaaaaa aaaacaaaaa caaacaaaca aaaaaaacac ctcaccatga gtgctacatg  93780
tgaatagata ttaagtgcca tatataatta gttctcagaa gaagggagaa atgatcatag  93840
gactgggaat tgttttgcaa acgttctagg agatgtgaga gaaaatatgt aaccacatct  93900
tagtggccca agaaaataca ggcctgaagg gataagattg tgtctctata gagcttcaaa  93960
gcatacaggt caattaagaa agcccctctc tctccagagc cgtttcccta gcttttggca  94020
cctggatgcc acagtcctcc attaggctga tgactccaaa gatgtaactc tagcctcttg  94080
cctgagcttc agactcgcgt cccactgccc acaggacaca tccacctgga tgtgactcac  94140
aggtacctcc aacccatcat gtggagatac tcatcctgtt cccctagag ctgctcttcc  94200 tgctgcattc tctctctcaa ttactgggac caccaagcta ggaacctggg agtcatcctt  94260
gatactttct cttcctcctt aatcctgtgt attcagcaag taactaaagg ttggtgttgg  94320
ccaggcatgg tggctcatgc ctgtaatccc agcattttgg gaggccaagg cgggcggatc  94380
acttgaggtc aggagctcaa gaccagcctg gccaacatgg tgaaacccca tctctactaa  94440
aaaaaaaaaa aaaattagtc gggcgtggtg gtgcatgcct gtaatcccag ctactgggga  94500
ggctgaggca ggagaatcgc ttgaacctgg gaggcagagg ttgcagtgag ccgggattgc  94560
gccattgtac tccagcctgg gtgaagaagt gagactctgt cttaaaaaaa aaaattggtg  94620 ctgataaaata ttgatgaatt ctgctctctg ctctctatgg ttgtcaacac tgcagagttg  94680
```

```
aggcctcata tctcacctgc actgctgcaa cagcttactg gtcccttgct cccagccttc    94740
tcctcttcag tccatcgtcc acacagcact ggggaagggg agccacttga aacaaaagtc    94800
aacaactggt tgtagttcat aaacacagag ctgtttgtgt ccctgtatc tggaatgcca     94860 ttatgaccca ctacattttt tctttcctac ccctcttaaa actcagttca ggtagcagct    94920
ccactaggaa gccttggctg accataatcc cattcaattc catttcacct cttcgcaggc    94980 agtctgggt tagggaccct ttctctttgc tccccaaaat aaactggtta tctctactat     95040
tggatttaca acattgtatt ataatcttct ccatgtgtgc cttctctagt agaatgtgag    95100
ctctttgagg ccaaggtcta tttaatttgt ttgaaaaatt cattgttata tcctcaaagc    95160
ctagcacata gtaggtactg aatgaatgaa tgaacaaggg gtgccaggag actgctactc    95220
ccagtccttc ccagaaactg cctagggctt tgagtcattt tatgaagcta ggtcttaatg    95280
cgtaggcaac ctcccagctc actatgaacg ctgacagaag agtgttttca tgtctataat    95340
caagaattcc agatacattc cttttactga accttgaatt gatcctaaga ttggtagtaa    95400
aggtattatg ttacctccta acagcactac aaagtacctt tttttatcag aaaaaaattt    95460
taccattagg actcaatttg aagtactaat gcttctcaag ttctccacta tgagagttac    95520
cctgtattag accgttacct ataagaatta aggggtaaag cactaaacag aaaagaaaaa    95580
aaaaatagca actctggtga gcagatttct ttcctttctt ccttccttct cctcttccta    95640
ccttcctccc tcctttccct ctcctcccct tctctccctt tccctccct tcccttcctt     95700 ttcttctttc ctccgctccc ctcccttcc ctccccttcc catccttctt tctctttttt     95760
ttacttaatc cccagtgtga cagtaatata ggctgatttc tagaagtgtg gtgtattact    95820 catgaaagt gagttgcctt ggttattact ttcaattgaa agttctatgg gatctagaaa     95880
tgagacatac tggcatggag agtgagaacg acaaaggaat gaagagctac aggagcattt    95940
aggccatttc tatgccaagc ttattctaca tgcacaaaat catacatgtt aataaatata    96000
aacaaattgg aggcttattt aaaccaatta tgaaatctgg taatttgtgc agcagcaata    96060
gatgataaca aaaaaaaact cataataatc tgaatatctt gatcatttgt atttaaagaa    96120
gcagtaatta tatacttgaa agtacataat atagtattgc aaaaatgact ttggtatatt    96180
acaaattaaa agtatataag atgaaacttg atttgctatc aagccccaag caattttca     96240 actgggcatt gaattctaac ttttctaaga tagcaatttt tgaagagaca cgaacaaaaa    96300
tctgaattag ttcatgagcc ttaatgtaaa tctcttgctg aaatagtttt taaaatcaga    96360
atttagttat ctatcagact caaaatcatt taaagactaa caaaacacaa tcatgatatt    96420
ctaactgtgg tcaaaccagg tacccaagcc acctccctgc ccaacgcctt tccggctttt    96480
cccctccctc ttgggctggt ggttatgctc ctccagctct agttcagcta taattccttt    96540
tatagagaaa ccaacctgat acacactttc atgatgggag aaaaatgtgg gagtgaaatg    96600
gtatttagaa agcagcagtc aggcacggtg gctcatgcct gtaatcccag cactttggga    96660
ggctgaggca ggcggatcac ttgaggtcag gagctcgaga ccagcctggc caacacggtg    96720
aaaccccatc tctactaaaa aaaaatacaa aaattagccg ggcgtggtgg caggcacctg    96780
taatcccagc tacttgggag gctgaggcag gagaaatcgc ctgaaccag aaggcagagg     96840 ttgcagtgag ccaagatcac atcactgcac tgcactccag ccgggtgac agagcgaacc     96900 tctgtctcaa aaaaaaaaa agaaaaaaga aagaaagaaa aaaggcagaa gccctggatt    96960
caaatccgcc acacattcag tttctttatc tgtaaaatgg agaccacccc ccgccacgct    97020
gaacggtgat tctgtgactg gtaagagatg ctacattttt ggtgcttgtt caggtggagg    97080
```

```
aaagatgata gttaacactc aggtaataag tattttgaag gcagtataat ataccttctt    97140
aaagagtata cctactcaaa tgttggtaaa tgttgacatg attgaatcta aatggcaaag    97200
agtattttag aaaaacatta agtccctgca gataaatgac agtgttgatt tggatgctta    97260
attacattca gacatgaact gttggatgta tctgaaatgt taaaagcttt ttctcaacat    97320
ttccaaaagt cttccaaga aatcaatgtt atgttttgtt ccagaagcaa atttgcattt    97380
gtgatctgtt tctaaaaatg gtacaagtta gctctgttta gaaagtaaaa atatctgatg    97440
ttagattgga agtatctctt cctggggaat ccagaaagat aagcatagca tattgtctta    97500
ctgcaataga taagttgctt attgagaagt ctggttgtta ttctatatgg taacaataca    97560
gttgatgtat attttatgat agatccttta tattttcctc atgactttag aaggggggaag   97620 ggggagaaaa ttatgatgac cagactagtt aaagagcatt gaaagtccac agtactgtag    97680
ctaaagtaga agtttgggtt tgttatagac tttacattat atcaactaat aagcagatac    97740
tgtacagtat tgctcaccat tttatcatac ttttgcatat gaactactcc attgcctttt    97800
atagatgttt tatagctgat cttaccagtt ttcctggtaa cttttttttat ttctttttt    97860 ttttttttgag acggagtctc gccctaacac ccaggttgga gtgcagtgcc gtgatctcgg    97920
ctcactgcaa cctctgcctc ccgggttcaa gcaattctcc tgtctcagcc tcccgagtac    97980
ctgggactac cggtgcctgt ctccacgccc ggctaatttt ttgtatttgt agtagagacg    98040
gggtttcacc gtgttagcca ggatggtctc gatctcctga cctcatgatc tgcctgcctc    98100
tgcctggacc tcccaaagtg ctgggattac aggcgtgagc cccgcgccc agccactttc    98160 tttaatacta taactaagaa tttattaaaa tgcacaaatt gtctaagact gtaaagttta    98220
tgggggagag gccatgacta cctctgaatt tagtaaattt aaaatatttc tgattctcaa    98280
taaagaacta atatccatat aaataatgct ttttttcccat tatgttacct gaaaataagt    98340
acttatgcaa gtaaacaaa gtccactaaa aataactgat taccaccaaa taaagcttgg    98400
gaaagaccaa acttaatgac cttttatgag gcaataacat tgcaacaact cttcaaagtc    98460
cagatagttc ttccagaaca agttacatat gctatatgtt atatatatta tatataatac    98520
attccaaatt aatttgtgtt gtggggcagt gtgttccatg gacaagatga tggatggaaa    98580
gtatgccttc tggtcagaaa aaatatttga aaattcacaa tttatattaa tgtaataaag    98640
aatctgagaa atgcagaaaa gaaatggatt tcccaaacat gctaagctat gggaccattt    98700
ccttaaataa tacagcctcg taccatccct ttggattaac ataccatat ttccaaacac    98760 attttgggaa atactgatat atagagaagg cttttgttct gaataacaaa ttttattgat    98820
ttccaggtgc ttttgaaata cagagaacag tggtaaacaa agaatttgcc tccagtagga    98880
actgaaaaac taacagtcct aaccctgct aatatcgact tagtcatagg acagaggatg    98940
ggctcaagct tacatctgct ctttgaaaca cgctaaacaa ataatagttt aaatgagaca    99000
ttgctgagta ggaaatggct aaattacagg taccaatttt taaaaagtga cgtctcaatt    99060
tagaaaataa acaggaaata gtttctctgt tttcaagaga atttcattac atagaagcct    99120
cttaagcaga agttccctgg tatatttacc tagacttcaa cgtttaaatt tgcagctttt    99180
tttttttttt ttgggacgaa gtctcgctct gtcacccagg ctggagtgca gtggtgggat    99240
ctcggctcac tgcaacctcc acctccaggt tcaagtaat tctcatgcct cagcctctcg    99300
agcagctgga attaacaggc acatgccatg acgcctggct aattttttgta tttttagtta    99360 agacaggggtt gcaccatgtt gcccaggttg gtcttgaatt cctggcctca agtgatccac    99420
ccacctcagc ctcccaaagt gctgggatta caggggtgag ccatcacccc cagccaagg    99480
```

| | | | | |
|---|---|---|---|---|
| gttttttgtt | tgctgtttga | caactgagaa | tagaactatt | atttctctgc tctcttggag | 99540 |
| tggtctctca | gcgctgttaa | gagtctacca | agcgtagtga | ctcacatctg taatcccagc | 99600 |
| actttgggag | gccgaggcga | ctggatcacc | tgaggtcagg | agttcgagac tagcctggct | 99660 |
| aacatagcaa | aaccccatct | | | | 99680 |

<210> SEQ ID NO 4
<211> LENGTH: 51039
<212> TYPE: DNA
<213> ORGANISM: Homo sapiens

<400> SEQUENCE: 4

| | | | | |
|---|---|---|---|---|
| tggtctctca | gcgctgttaa | gagtctacca | agcgtagtga | ctcacatctg taatcccagc | 60 |
| actttgggag | gccgaggcga | ctggatcacc | tgaggtcagg | agttcgagac tagcctggct | 120 |
| aacatagcaa | aaccccatct | ctactgaaaa | tacaaaaatt | tgccaggcat ggtggctcat | 180 |
| gtctgtaatc | ccagcacttt | gggaggccga | ggcaggcaga | tcacgaggtc aggagttcaa | 240 |
| ggctagcatg | gtggctcatg | tctgtaatcc | cagcactttg | ggaggccgag gcaggcagat | 300 |
| cacaaggtca | ggagttcaag | gctagcatgg | tgaaccccg | tctctactaa aaatacaaaa | 360 |
| aattagccat | gcatggtggc | atgcgcctgt | aattccaact | actgggaggc tgaggcagga | 420 |
| gaatcatttg | accttgggag | gcagagtttg | cagtgagctg | atagtgcc actgcactcc | 480 |
| aacctggagt | gagagactgt | ctcaaaacaa | acaaacgaac | aaacaacaac aacaacaaaa | 540 |
| aaaaaaacgg | ccaggcgcag | tggctcacac | ctgtaatccc | agcactttgg gaggccaaag | 600 |
| caggtgggtc | acctgaggtc | aggagttcga | gccagcctg | ccaacatgg tgaaacccg | 660 |
| tctctactga | aaatacaaaa | actagccagg | tgtggtggtg | gaccctgta atcctagcta | 720 |
| ctctagaggc | tgaggcagga | gaatcacttg | aacctgggg | gcagaggttg cagtgagccg | 780 |
| agatcgcgcc | acttcagtct | agtctgggcg | acagtgaaac | tccatctcaa aaaaaaaaa | 840 |
| aaagggtct | accgttagtg | dacaccttta | gtcttccaac | gagatacttc cacctcccac | 900 |
| cttgtggtta | aaaaatgctt | aactttgggc | tgggtgcggt | ggctcatgcc tgtaatccca | 960 |
| acactttggg | aggcagaggc | aggcggatca | tgaggtcagg | agttcgagac cagcctggcc | 1020 |
| aatatagtga | aaccctgcct | ctattaaaaa | tacaaaaatt | agctgggcat ggtggcaggc | 1080 |
| gcctgaattt | ccagctactc | gggaggctga | ggcaggagaa | ttgcttgaac ccaggaggca | 1140 |
| gaggttgcag | tgagccgaga | tcatgccact | acactccagc | ctgggtgaca gaacgagact | 1200 |
| tcgtccccc | caaaaaaaca | aaaagcttaa | ctttgaagag | atttggtctt ctcagatgcc | 1260 |
| tcctataaaa | agaaacaaat | gtgagaaaag | gtagaaaagg | cctttttgt agggagcaat | 1320 |
| tttttctaaa | aaggctttc | agccaagacc | ctctctctta | caattctgac accatatcaa | 1380 |
| cttttaagac | tactttttc | ttagaatgct | tcttttttgc | catttattgc acaaacaata | 1440 |
| atttgggggg | ggactttaaa | aaatcataat | caggccaggc | acagtggctc aatgcctgta | 1500 |
| atcccagcac | tttgggaggc | cgaggcaggt | ggaccacatg | aggtcaggaa ttcgagacca | 1560 |
| gcctggccaa | catggcaaaa | ccccatctcc | actaaaaatg | aaaaaattag ctgaaataac | 1620 |
| acagctactt | gggaggctaa | agcaggagaa | tcacttgaac | ccaggaggtg gaggctgcag | 1680 |
| tgagccaaga | tcacgccatt | gcactccacc | ctgggcaaca | gagcaagacg ccatctcaaa | 1740 |
| aaaacaaaca | aaaatcaca | atcagtgaga | ttaatgttta | atgaacatac tgttattttt | 1800 |
| tatttttta | agagacaagt | ctccatcgt | ctcctaagca | gagtgtagtg gcgcaatcat | 1860 |
| agctcattgt | aacattggac | tcctgggctc | aagtgatcct | cccacctcag tctcccatgc | 1920 |

```
atgccaccac aattttttgg atacaggctg tcattatgtt gcccaggctg atctcaaact    1980
cctggcctca agtgatcctc cttccttggc ctcccaaagt gttgagatta caggcgtgag    2040
tcacagagcc tggcccagga tgttatttta aaattgtctt tttgtcttct aaatcaacaa    2100
gaacttgata gttgctttca atgccaatca acatccttta ctactgtata cacaatgtat    2160
ttatttgaca tttgaaagga gatacggctg ggcgcggtgg ctcacgcctg taatcccagc    2220
actttgggag gccgaggcgg gcggatcaca aggtcaggag atcgagacca tcttggctaa    2280
cacggtgaaa ccccgtctct actaaaaata caaaaaatta gccaggcgcg gtggcgggcg    2340
cctgtagtcc cagctactcg ggaggctgag gcaggagaat ggcgtgaacc tgggaggcgg    2400
agcttgcagt gagccgagat tgcgccactg caatccggcc tgggctaaac agcgggactc    2460
cgtctcaaaa aaaaaaaaaa aaaagaaag gagatacaaa aggatgttac aacctgctat    2520
ggcaagaaga tacaaggaa catattggta tgaacagaat acctcagagt tgagtgtata    2580
aaaaaggctt aattcaccag atgcagtggc tcgcacctgt aatcccagca ttttgagagg    2640
tcaaggtcaa gacacgagga ttgcttgagc ccaggagttc aaggccagcc tgggcaacat    2700
agcaggactc tgcctctaaa aaagtatat atatatatat aatgtacaca cacatacata    2760
cataaacaca tatgtattat atatatatat gtaatatatg tatattatat ataatatata    2820
tattagccag gcatggtggc aacaggcctg tgttcccagc tactcaggag gctgcagtga    2880
gtcatgtttg cgccactata ctccagcctg ggtgacagaa tgagaccctg tctcagcaaa    2940
aaacaaataa aaaacttcaa ggtggagtag gggttaattc aaggctacct aagctggatt    3000
tggggtgatt atggtcgagt ggatgcaaac agaatattaa acttccattc attaaaagtg    3060
cttactacct gccagacccc atactaggct ctatagattt attgtctcta aggtcactag    3120
gcgagtaagt accagatctg tgactttgaa cttcccacta caataagctt atgaactttg    3180
tttaagcaaa aaaggtttga aaagtgaaaa gcaagcaccc attttcatagt gttctaaaag    3240
tctaaaataa tccagtagaa catcagagat aaaatccaaa aagcaagttt ttcccccaat    3300
atttaaatca gggaagcaac atgatggtat ctgtaaacta taactgaacc aaaaatagga    3360
ccaaacgtag tgaaatccat ttagggagat attactgtga tcttgaagga aggcctactt    3420
aatacaggac agtgggctgg ggaggtgtga accaaaaata gacacaggca aaagcgctaa    3480
aatttaaccc tgagaaataa atgaaattca cctacaaaat aaatggaata aatttaaaag    3540
gtgaaatttt gggcttggcg tggtggctta cacctgtaat ctcagcactt tgggaagcca    3600
agacgggcag atcacttgac cccaggagtt tgagaccagc ctgggcaaca tggtgaaact    3660
gtctctacaa aaaatacaaa aattaggccg ggcacggtgg ctcacgcctg taatcccagt    3720
actttgggag gccgaggtgg gcggatcatg aggtcaggag ttcgagacca gcctggacaa    3780
catgctgaaa ccccatctct actaaaaata caaaaaaaat agccaggtg tggttggcga    3840
gcacctataa ttccagctac tcaggaggct gaggcagaat gcttgaacc tgggaggtgg    3900
aggttgcaat gagccgagat tgcaccactg cactccagtc tgggtgaaag agcaagactc    3960
tgtctcaggg cgggtggcag cggggtcggg ggaggtgggg ggaaggttag ctggacctgg    4020
tggcttgcac ctgtggtccc cagctacttg ggaggctgag gtgggaggat tgcttgagcc    4080
caggaggttg aggctgtagt gagtcatgtt tgcagcactg cattccagcc tgggcgacag    4140
agcaagaccg catctcaaaa caaaacaaac aaaggtgaa attttggaat taggaaagat    4200
gctattttta taaattggct ttaagctgtt ggctggacat ctaagttgta gcattctgaa    4260
ggcagcagag atgtgggatt gtaggactga acatgaaaa tgcctatcga atttttttta    4320
```

```
aagtctttaa aggagagctt taaaggaaag caatacgaat tcaagtatgt ttcagtacca    4380
ctcctctctc taaagacaat caactatggt tttcattcaa atactatta ctctaacgtt    4440
aaatatttga gtacagcaat catttcagat gcattatgaa taagttactg aacacgcctc    4500
ccatctgctt gctttacggt tttattttgc ctttcgtttg ttagctcatt ttataatttg    4560
ttacttctga acaccttcca agtgctggtg ctttcagata tctacctcaa agtattattt    4620
gtaaatgtca aaaagtccct cttacatata attgaaagct ggctacatgg tagacaatat    4680
gatcacaaac ttttaaacaa ttttttaagc tgaagaaata cttttctttt ttataagtat    4740
caaatcaaaa tgtaattcag catccaccca taaagcgcaa ctaaaaactt ttcacaatgc    4800
cattaacaac ttgtggttac catcataagc ctacagacct acacactaat tatctttaaa    4860
acccttatta ggctgggcgt ggcggctcac gcctgtaatc acagcacttt gggggggccaa   4920
ggcgggcaga tcacttgagg tcaggagttt gagcccagcc tggccaacat agtgaaactt    4980
catctctgct agaaatacaa aaattagcgg ggcgtggtga cagggtgctc taaccccagc    5040
tacttgggag gctgaagcag aaccacttga acacagccag gaggcagagg ttgcagtgag    5100
ccaagattgc accactgtac tccagcctga gccacagagc aagactccgt ctcaaaaaat    5160
aaataaaaat aaaataaaac ccttattaag gatttaaaaa atcttaatta tataatgcca    5220
aaagctagtc cccgtctggc ttaggggccc acaagctcct gctttaaagc cagttttttt    5280
gttttttttct gatgtactta catttgtgcc tcacaatcaa gaggttccca gcttggtgga   5340
actttcaaag atgaggcaga aaactaaaca ggcaattaca atcttacttt tcacgctgac    5400
aagtggtacg gtggctagcc caaactcccc tccctgtccc agctacctcc cttatagacc    5460
attcacgatc acttaggcca ggctgccatg tgacctaaga gaagacaggg agaacacagc    5520
atttcttact cctactaact tgcaacatca ttctctcaag ttgctctcat tggaggctcc    5580
caactgcttc aagctgccca gtgatatttg tatttctaaa gtgggcaggc atggccattc    5640
cagaaaaaga aacacattca gacttgtgcc ttttgttacc caaatatatg atattcaaat    5700
aatttctatt ttaacaactc ataaaaattt aagatcaaat aattgcattc ttgaaacaat    5760
tcttaatcat ttattttcaa cacgtgtact ataaagaacc taagaaatca gacaattta    5820
ataacccata aacatgttga atccatttgc agatttaaat tttgtaaaaa tagctgtcac    5880
tgcctccata tatcaagtgt actatgttta taatcacatt tatgctaccg atactcctca    5940
gaaaaaaaca gattctgctt ggttctagct tcagtattat gaactccaat aatgctttga    6000
ggacctccaa aggaaaaaaa cagattctac taggttctag ctgaaatatt atcaactcca    6060
aattgaagct gaagtattat caactccaaa taatgcttcg aggacctcca aaaaaaagag    6120
attctgcttg gttgtagctg aagtattatc aactccaaat aatgcttgga ggacctccac    6180
aggtaaacta ctaatccctt tggccattta ttgagacaga cagagagaga gagagagagt    6240
tttgaagcaa caatgtacca ttagtaaagt tgctgtgcag aattacctca gtcctattct    6300
aagcttacag ttcagttgat tttattgtct tcacctaagt atatacaatt cacatatggg    6360
agaaaaacac taaatcaaga tggttatttt cactgttttg cttaagattc atatttaaat    6420
ataaatcaag aagttaatcc acagtttgag agatacttat attagaaatt ttaaatgtta    6480
aatacataat tgtaaatatg gtgtatgtac tgtttcacat acaatgggta ttgatcaaat    6540
cagtgtaatt agcacaccca tcagctcaaa tatcatttat ttgtagcaag aacattcaat    6600
acattaacta tagtcaccct actctctctc tctctctctc tcaataaatg gccaaaggga    6660
ttagtacttt tacctttgga ggtcctcaaa gcattatttg gagttcataa tacttcagct    6720
```

```
agaacttatt ccttcaaatt taactctgta cccattaaaa gtggttttgt gtgcaattaa    6780
cagacacatg ttctacccat acattgtttt ccaaaattat tgtgtggctt taaaaaaaaa    6840
aaaacccaca caacaaattg caaaaggcac tgagataaca tctgcttcta gatcattgct    6900
aggctcgaaa aataaagctt gttctaccag gaatgacaag ttagaactta gtatttgcca    6960
aagcagaaat tatatagtgt cagttatttc aggcaaacct tattcggctc tcatccccaa    7020
ctatctgtca gaacaattaa aagagatcaa aacagtccag cataactagg cttcattata    7080
taaggccatt ttgttctaag acactaataa accaaaataa gaaatattaa aatcaaaata    7140
aaagatatta tttgagctat tttcatacaa actgttggtt ccttatatcc tcccttctat    7200
aataaagggc atattttact gcaaagaaaa ttttacttta tatatatcac tagccataaa    7260
tttttgaatg tcattaatta catgttgtct agtaccatta accaaatagc gtaactattt    7320
tatgtccaca tttcacttct gtatttacaa acatatcagt aaagagttaa caatgagatg    7380
cgatcaaaca tccatattat ctgttttgta gacagcaatg tagatgattt tgtaatcacc    7440
tttcatcgga gtgaccttat ataaaaaata agtcaataat ttagaggttc taagtctcca    7500
aaggagattt tcaaatgtaa atatagaaat ggttatagat aatgagattt ttaggaaacc    7560
tctgccatgt ctgcatcctg ttaactgtta tatcatcttt tcttccagct gcgttccttt    7620
gcctgcaaca ggggtcaaga tgagttttgc ctgacttctt tgatgtcctg aactttccgt    7680 agtcctttt cttgaatttg ttcattataa atatagcttg gcatttgttt gatcttttca    7740
actgtcttca ctgcatcagt agttttattc catagttctt gcagatattt gacaggcttg    7800
ttactatatt tttcaaattc aaatccactg taagctcatt attagcagtt gctttacaga    7860
atgctttagt ccacctaacc ttttgagaat tgcacttctt ttaaagtttt tgtgacatttt   7920 atgtttatac aatctgaaca ccttgcaaca gctgcagatg aacatcatga tgtggtcagg    7980
gtagatgggt cccaaagaaa ctaacacttc tcagtgctga gctcggatgg gcctccactg    8040
accaaacacg gagcttgaga ggaagtcaag aggtatcttg gaattccaca tgctgaccct    8100
gtcattcttg aaggaaaatg atgcataatt tctgaataat tcagaaagaa cttaacaatc    8160
tttccagtta gttttttaaat aacaattctg tttatcaaat ttctgaatta acttttctga    8220
attcacgggt ttctaaaact ggccttaagc aaaagtctga aacctaggct gggaaccatg    8280
taacccaggc caagaaggta ctttaaagtg tcttagagtt gttttttcaac ttaggggaa    8340 acaacagatt ccattaaatc ccataaagga ttttttttgtg tgtgaaaaag ggcctgatgt    8400
aatctaggtt agactcagga ggctttaaca agttttgtct tacgggtaaa tggtggctat    8460
tttcacagat aacatcatta ctcccatccc ttactatggt ttatacaaaa gaggctggag    8520
aataagtaca ttttttacagc cgggtgtggt ggctaacgcc tgtaatccta cttagcactt    8580
tgcgaggcca agacaggagg atctcttgag cccaggagtt cgagaccagc ctgggcaaca    8640
cagggagacc ctgtctctat tgttaaatca agaaaaccta aaaaacattt tcatttacat    8700
agcaccaaat ataagagcct ttttttttttt aacctagaaa gagtattttg gagagagaaa    8760
ctaaggatca gaaggtttaa gagtatcaaa aatctgaggc caggtgcctc acatctgtaa    8820
tcccagcatt ttgggaggct gaggtgagta gatcacttga gtttaggagt tcaagatcag    8880
cctggctaac atggtgaaac cctgtcttta ctaaaaatac aaaaaaatca gctggtatgg    8940
tggtacatgc ctgtaatccc agttacttgg aaggctgagg caggagaata gcttgaaccc    9000
agaaggcgga agttgcagtg agccgagatc actccactgc actctagcat gggtgatgga    9060
gcaagactct gtctcaaaaa aaaaaaaaaa aaaaaaaaaa aagagtatct aaaatttaaa    9120
```

```
tactaattct tggctggaca tggtggctca catctgcaat cccagcactt cgggaggccg    9180
aggcgggtga cctcacttga ggtcaggagt tcgtgaccag cctggccaac atggtgaaac    9240
cctatctcta ctaaaaatac aaaaattagc tgggcatggt ggtgcatgcc tgtaatccca    9300
gctgctccag aggctgagcc aggagaatgg cttgaacccg ggaagcggag actgctagat    9360
catgacactg cactccagcc tgggcgacag agagactcat ctcaaaacaa acaaacaaac    9420
aaacaaacaa aaaacaaaa aactaaatct ttcacacatt ttctctttat atcaaaggta     9480
ctaagtgaca tttaggccgg acgcggtggc tcatgcctgt aatcccagca ctttgggagg    9540
ccgaggtggg cggatcacga ggtcaggaga tcgagaccat cctggctaac acggtgaaac    9600
cctgtctcta ctaaaagtac aaaaaattag ccaggtgtgg tggcagatga ctgtaggcca    9660
agctaattgg gaggctgagg caggagaatg gtgcgaaccc gggaggcaga gcttgcagtg    9720
agccaagatc acgccactgc actccagcct gggtaacaga gcaagactcg gtctcaaaaa    9780
aaataataag ttacatttaa atgtcatata catatttaag aaaaaaaaaa accaagtact    9840
tctcatttaa gacagagtag aaattattta aaattaggag ttggtgtaaa ggatgagcta    9900
catattcaag tcaaattata gtaagtattc actattccac taccaaagta ggtcaattat    9960
actaaagaga agaaatctat gtgaattgag gcattttctc actttgatat atgtgaataa   10020
atttcaggtt gtctaaattc ctagggttat atagttagaa atatataatt ctcttataga   10080
caggtcaact aggggaaata agttagcaca atcatttgaa ttggttgtct acatactggg   10140
cagggcttat tccttttctt tagcttcttt gcacatgtaa agcaggccat aagatgtcct   10200
gttttgccat ggacaatgca accatttta ggtcgacctt gacaaatcac acaaggttca    10260
atggcattaa ggggcaaact agattccaca ctctcttctt tgtcttgggt ttcttcccctt   10320 tcaaactctt tcacatcttc ttggctgcta taaataatgc tactagaagt tgatggctga   10380
gaatagtctt cactttcttg tgattgtgaa gcttgtgtaa ttttatcatc attttcctca   10440
acacatgact ctctggaatc attcactata gttttttttac aatcaggaac atcaaagccc   10500
tcttcagctt gtgttgagtt ttccagtttg gctttctcag agatttcccc tttatctttc   10560
cctttatctt caggaagcca attctcacga agggcccaac atctgttgca atgtgatgga   10620 aggggggat tcatttcatt gcatgaagtg catttccaat agtccttcaa tgaaataaga   10680
cacacagtca gtttctgtaa ccctttaact gctcagtcac aggaatgcta gcaactttgc    10740
tatgtctaag gtaaagtata tcataggggct caatattcag tgtttcatgt tttatataaa   10800
atagtcactg taaacagcat gaggactata gttagttata tattggtata ctggaaattt    10860 actaaagaa tagattttag gtattttaac catacacaca agaaaggtta actattcaag    10920
ataatggatt acattaattt gcttgactgt agtgatcatt tcactattta catgtgtgtc    10980
aaaacatcac gttatatgtc tcaattatac acaaaacaga ttttaaagg tcaatatgta    11040 acagtctctc ctaaagtaga gtaagtacac ccatttttt cacccttacc atcctgaaaa    11100
attctaaact aaaaatatat taactgtgat gtgatattaa tcatgtacct ataaagttat    11160
ctgtttcagg atacaaatgc agttgcttcc tttagttgaa gcaagtctat gggatctttt    11220
actctgtcat gcagcctata tccactccct taaaggctca accctaggcg ctattccaag    11280
agtccatccc atcaatctag atgaaacctg cctcctcgag aaagacttcc taatccacca    11340
gtgactagaa ctaccttaga agtactctaa aaccatggct taactgagta ttccctaact    11400
ccatccacaa gagaaatgct aaaacatttt tcacagcaag tattgctgct aaaacctatc    11460
atccttggtc actaaccgta atatcctttc ctttacctgt ctatcctttc ctgtgttctc    11520
```

```
atctttgtaa ctgctcaatg cttcttcctt ttcccaacgt tttatcccac aaacctttcc   11580
accatgcaat ttggataaca aactctccca catcccagc cttttacat aacctatctt    11640
cttgccttag ctgaagcatg gttcttgcct gaggacattt aacaagtgaa aactcttaag  11700
taagaggtat ttccgtaacc attttgagat tgcctcacaa atgatgttaa gacaggagca  11760
ataaagatag actattcatt cttctttttt caagttatag aaggggtttt ttcacagctc  11820
ataaaaccaa agaaaaaggt cttgcaatat gggagtaaaa gtgcatcaaa aagtccaata  11880
aattccaaga tgaatatcta aaataatttg agtcttaaaa tagatttaaa aaattaaaag  11940
tatctaaaat attttactca acttgacatc aaatgattca attagttatt tattttctaa  12000
tacagtaaaa attttggaaa ctcttgaatt ttcatccttt tttgcacttg aataattagt  12060
aactgtctat aactcagaaa aaatggaatt tatttcctat tcaaatataa taaaggcaat  12120
attaagaaca aaaactaaag cacaatagtt ttaaaaaaac ctataatacc tcaggaactc  12180
agtgaagtat gcatgagatg taaacattta agtgttaatt tctttaatgg caaatcctac  12240
cacattctat aatacaaatc agtaataaaa atgtttacat ttggctgggt gtgatggctc  12300
acacctgtaa tccttgcact tgggagact gaggcaggtg gatcacttga gcccaggagt   12360
tcaagaccat cctgggcaac atggtgacat ttctacaaaa aatacaaaaa ttagctgggg  12420
tgtgatggca tgcacctgtt attccagcta ctcaggaggc tgaggtggga ggatcacttg  12480
agcctgggag gtgggggctg cagtgagcca tgatcacatc actgcactcc agcctggaag  12540
acagggcagg accctatctc aattgaaaaa aaaaaagtt tacgtttgac aaggttggca   12600
aaatgttggt aatagttaaa gctgggtgat gagtatactg gagatacact gaaattttcc  12660
aaaataacat caaaatgtac aaattcagct gggcagtgac tcatgcttgt aatcccagca  12720
ctttgagaga ccaaggtggg cagatcactt gaggtcagga gttcatgacc agcctggcca  12780
acatggtgaa accccatctc tactaaaaat aaaaaaatta gtggggtata gtggtgcatg  12840
cctgtaattc cagctactca ggagactgag gcacgagaat cacttgaacc tgggaggtgg  12900
aggctgcagt gcactgagat tgcaccactg cactccagct tgggagaagg gtaagaccct  12960
gtttaaaaaa aaaaaaaaa aagttcaaat tccagcacct aaaaataaaa attatagcta   13020
caggtctcat cacaacaaat aaaagaaaaa tgctttaaat tattcagact ttacaaaaac  13080
attttaactt tataaaaatc agttcatttc agaaagaagc tagatatagt ctcctaatct  13140
tgaccttaat gaaattttta tttcttaaaa aagtagatgt atacttacag ctaaggaaat  13200
ttcaggatct tcttcaaatg aatctgtatc actctcccct gcctgataca cagtaacttg  13260
atatacctaa taaaacacat tcattagcat caattcatcg ccctatttcc ttcaatcaga  13320
aggcttccta gtaataagtc ctaaacaaat atcatgtact acaatatatg agaaagcctt  13380
agacaatatc aaatagagta agtgagtgta aaggggaaa aaatggagga gagagaaatc   13440
cttacccaca atggtaaaag tcaatacaaa ggatgtttag gatgaataaa acaaaacatt  13500
cagctaggtg gttttacttc ataaataact aatatggaga tattaaataa tagggaaata  13560
gctagaaatg ttaaaggcag tcacttctgg gaaacagatc tctaagggta ctacttgact  13620
ttaactgtat gcatgtttta ctttttataga agtaagtta atattaaaac agtagttgaa  13680
ttatatgttt ttaaaagtga acagaccatt ataataagca tgttcattga ggtctattga  13740
cttcttggca attagtagta atataataat ataaatcaga tgataaagaa ctatgaaatc  13800
ctcaagtcca caaccaatg tgttagttta aacaaatcaa gaggtaaaga tttcaagtga   13860
aatctgaata atattatttc aatctcaaag tcaatgaaca tagaaaatat ttaataattt  13920
```

```
tccaatataa ttagagggga aaaaaaatac tacctcatca tcttcatctg agagttcttg  13980
tccttcttca ctaaggctat aatcttctga gtcgagagat tcaacttcaa attctacact  14040
aaactgatct gaaactgaat cctgatccaa ccaatcacct gaatgttcac ttacaccagc  14100
atcaagatcc taaaacaaga aaaaaatata taacttaata aacatcacct cttgacctct  14160
gtatctgttt cctaactcat ccctgtgcct ctgctgctgc cagcagggtg taacagttgg  14220
gggatgggcc tgctgctctg atccgggact tcccgaggga gatcggcggg cagaagacta  14280 ggcccccccag ccagccatcc cggagccggt tgccacgcac atttcctcct cagatccatc  14340
ctgcatactg aaactagatt aaggtttcaa ggttattact acattatttt ccctgttcaa  14400
aaccccactg cataaaggaa aaacaccaaa gcctcttggc atcgaaagta cctacagtgt  14460
gactgtatta acatcttcgt ctgtcttcaa ctagacaccc ctcctccctt actaaatatg  14520
gataatcccg ccagatctag attgcttcct caactaatct tggcatttca acttccacac  14580 tttcccccctc taactagaat aatttcagtt tcaaaatcct attcatcctt ctttgactaa  14640
gcctttgtca ataccataac tgaaaaggct cttccacctt taattatcct tactacttgt  14700
ataataatga attatatagt ctcacacata aattatgcaa aacataattt tgcaggcatg  14760
tttctcatct gaattatata tactttgagc taaaacctgt cactcatctt tctatgtcca  14820
aattggtaga atacacgtaa caagacacaa cacttgtaat acttatgggt ttttttttctt  14880 agaaaaatgt ctcgagtcat agatacttat gttttttaat aaactttgag attttctttt  14940
aaagagcctt tagacaatta aaaaaaattc tgtagctgct catctgattc ttcgtttcag  15000
gacttcaata aattgtataa gaacctagta agaccttcag ggcaataata tttgctgtca  15060
gtggctaagg gtaggagcat atataagcag aaggctacaa ttggaaaaag tctagaagtc  15120
gggatatggc ttattctaca cttgccacta agtagctaat ttaaccttaa acaacatcat  15180
ttaacttatt ttatttattt tgagatggaa tcttgctcca tcacccaggc tggagtgcag  15240
tggcctgatc tcagctcact gcaacctaca cctcccaagt tcaagcaatt ctcctgcctc  15300
agcctcccaa gtagctggga ctacaggcgc atgccaccat gctggctaa tttttgtatt  15360 tttagtagag gcagggcttc accatgttgg ccaggctggt cttgaactcc tgacctcaag  15420
caattcaacc gccttggcct cccaaagtgt taggattaca ggtgtgagcc accatgcccg  15480 gcccttttttt tttttgagac aagagtcttg ctctgtcacc caagatgaaa tgcagtggca  15540
tgatctcagc tcactgcaac ctccgcctcc ggggttcaag ctattctcct gcctcagcct  15600
cccaagtagc tgagattaca ggtgtccact accacacccg gctaattttt atgtttttag  15660
tggagacggg gtttcgtcat gttggctggg ctggtctcga atcctgacc tctagtgatc  15720 cgccacctcg gcctcccaaa atgctgggat tacacctgtg agccacctcg cccagcccat  15780
atcatttaac ttctaaaggc tgtagctact tcatctagaa aaggagctta gattaaatga  15840
tttccatatc tgtatcagtt ttaaaaacag aaacaaagta tattatttta cagcctctga  15900
catcaaaaga ctttttttaga gtaatgttag gaaggagagt aaaagcaaca ttcatcaagt  15960
tgcagctcaa attcctaaca agggctctac taccaatcag attagaatca caagtcaagt  16020
taggatacaa ttaacactaa caaagtaacc caacaaacca aatacttcaa ctaactaaag  16080
tctttagtgc actaattta gaataagggg gtaaatcaca agaaacatta aatctcagaa  16140
aacatactct acggtagggg tctgcaaact gtggcccatc acccatcgac ttttataaat  16200
aaagttttat tgaacacagc catgcctatt tgttgacttg ttgtctacag ttgctcctgc  16260
attacaagag cggggctgag tagctgtgac agaaaccatg gcccggcaga gcccaaataa  16320
```

```
ttaactatgt ggctctttac agaaagtttg ccaactcctg tcctaggata ctataaaaat   16380
actataaaaa ataccatgaa aaaatgcaat attgggagtg gtttttaaag ttttggctaa   16440
tgttcgcaaa agaatgcccc agaaactatt aaattatctc tctctatata tatttttaaa   16500
atatataaaa taaatattta aaatatatat ttatatttat ataaatagta atatatataa   16560
tatatacagg tgcctgccca tttatattta cataaatata tatttttata tttatataat   16620
tatattttta tatttatata aatatatata tttatattta taaaatata taattatata     16680
aatatatata acaatgtaat atataatata cattaatata taatagattt ataattatat   16740
attatatatt tatacattat ttaaatataa atatatatat atatatattt tttttttttt   16800
tttttttttt tggagacaga gtctcgctct gtcacccagg ctggagtgca gtggcaccat   16860
ctcggctcac tgcaagctcc acctcctggg ttcacgccat tctcctgcct cagcctcccc   16920
agtggctggg actataggtg cccgccacca cgcccggcta attttttgta ttttttagtag 16980
agacggggtt tcgccgtgtt agccaggatg gtctcgatct cctgaccttg tgatccgccc   17040
gcctcagcct cccaaagtgc tgggattaca agcatgagcc actgcaccag acctaaatac   17100
tatatattta aaaagcatca ggctggaggt ggtggctcat gcctgtaatc ccaatactct   17160
gggagccaaa gcaggagaat cacataagcc cagcggtttg agaccagcct gggcaacagg   17220
ccaagatctc atctctgaaa aaaaaaaagt aaaaaaaatt agccaggtgt ggtggtgcac   17280
acctgtagtc ccagctaact ctcaaggctg aggaggaagg attgcttgaa cccaggaggt   17340
tgaggttgca gtaagccatg atcatgcgct gcactcccgc ctgggcaacg gagtgagaga   17400
ctgtctcaaa aatttaaaaa atatatattt ttttaagcat cagataggct tgctctgcaa   17460
agatcttaga tctttgtagt caaaaatacc tagaattgtt tgaattccaa ttgtgacaat   17520
tagttgtagg aaccttaaac aagttattta aaaccccagt cttagctaaa aatggaatct   17580
gaggctgcaa agatgacaga agatcataat ataaactgca tggtgtacag tctagaacac   17640
agtcttagtt tcccacaatt tattaaaccc caaagaaaga aaagatggga gaggaatgca   17700
ctttcccttta actcccttca caaactggtg aatgatgaca cccaatgatg actacaacat   17760
tctcaaatga gggaaattaa acgaagaag aaaaaaaaac tggccctacc aaaagctttc     17820
acaactaggg acttaacctg aaaaacgaga ttttgttgtt gttgtttgag atggaattc    17880
gttctcgttg cccaggctgc agtgcaatgg cgtgatctca gctcactgca acctccgcct   17940
cccgggttca gcgattctc ctgtctcagc ctcctgagta gctagattac aggtgcccgc     18000
cactatgccc agctaatttt tggtattttt agtagagatg ggttttcaca acatgttggc   18060
gaggctggtc ctgaactcct gacctcaggt gatccgcccg cctgggcctt ccaaagtgct   18120
gggattacag gcatgagcca ccacgcccgg ctgagatttt ttatagatag gatttttaa     18180
gagaatgcag gacaggacta acaaaaagaa aaaagaaat acccctctac tccacacgag     18240
ttattaagaa attatttag gcaaatggag aggaaagtg gtccttggaa ggtttttcgt      18300
agctccagaa aaatttcttg tctagcataa aagccctggc tcttaaaggc tggcaacctt   18360
taagatgcaa atgcaagagg gtccacccaa catggcgatt ccaccgttg tcctcttgcc     18420
cttgctccat caggtaccta acagcatggc cgcccccaca taaccccgtg tgtaaaatgt   18480
catggcatcc tgcatttgtg tattaaagga ctggggtggg agggccagtt ttcttgaggg  18540
ctaaatgaca tgcctggtca aaccaatcct ctgagcccta tgcaaataag acaccacccc  18600
ctccagccgt cacataaaac tggctagtat tgtcagaatg taaggtctcc tctttcagct   18660
ttagagcccc cctccctctg tctgtgtaag ggggagcttc ttccttctgc cttctccctt   18720
```

```
cttgcctatt aaacgctctg ctccttaaaa ccactccacg tgtgtccgtg tcgttttatc   18780
taattcaact caaaacaaaa aacctggtgt tcctctactc ctcaaagcca tatcagtaac   18840
aaggcagtgt cccaggtaca aagcaggaac aaggactcta aatatcattc agctagaatt   18900
ctgatataac tttaacaaaa actatacatt aaatagggt ccgggcaggt ggctcacatc    18960
tgtaatccca cactttggg aggccaaggc aggcagatca cttgaggtca ggagctcaag    19020
accagcctgg ccaacatagt gaaacccat ctctactaaa aatacaaaaa ttagccaggt    19080
gtggtgatgg gagcctgtaa tcccagctac tcaggaggct gagacatgag aatcgcctga   19140 accgggagg tggaggttgc agtgagccaa gattgcacca ctgcactcca gcctgggaga    19200
cagagagact caatctcaat aaataaataa atagggtata ataattctct ttttaaccaa   19260
acttgtaggt tggatactca tcaagtttta attggattca attttatcac atatatttcc   19320
gctcaagagc ctatttttc cactggattt attaaatgtt ttcattttg tcattaatga     19380 tctatctccc aatgaaggca agaaccatat ctaccttgac taccactgta tctgcagtgc   19440
catctcaact gtatggaatt tggtataaac ttaaatatct acaaatgaag aacctgctct   19500
cagactgagc aggagctcat catgccatct agcggtctac ataagtaaca gctccgttag   19560
gtacagtaac tctagagggc aggtatgcgt tcatacaatc actgctttgg aagagaaaaa   19620 aagataaatac aggaagtaac aagaataggt aaaagactag gattactatc acaattggtt   19680
ccacttccta catcttctag agtactatac aatgattact aatacccaga ataatggcca   19740
tgagacactg ccatattacc aaaaaatgta tccaatcctt tggtttccgt gggcgacatt    19800
ggaagaattg tcttgggcca cacataaaat acactaacaa tagctgatga gcagaaaaaa   19860
aattgtaaaa aaaaaaatca taatatttta agaaagttta tgaatttgtg ttgggccaca   19920
ttcaaagcca tcctggcata tggcccacag gccatgggtt ggacaagctt gattaaagac   19980
atacaaaaca aaatattcca tttgtcaagc attcttgtta acaaaaaaat tttttaccaa   20040
acttctttca gtgacatctc ttaagaaatg ctgctcacta atattttgga agtctgtatt   20100
agtaatgaga aagtactgat actctcccgt catccatgca ataataaacc tgcatttttt   20160
tttttttttt ttgagatgga gtctcgctct gtcacccagg ctagagtgca gtggcacaat   20220
ctcagctcac tgcaacctcc aactcctggg ttcgagcgat tctcctgcct caggccccca   20280
agtagctggg actgcaagca tgcgccacca cgcctggcta ttttttgtat tttcagtaaa   20340
gacatggttt catcttgttg gccatgctgg tcttgaactc ctgacctcag gtgatccacc   20400
cgcctcagcc tccgaaagta ctgattacag gcatgagcca ccgcacccag cccagtataa   20460
acctgtattt tacagcataa gtaaatagaa cttacctgat gtctagacct atttggcaaa   20520
tgttaagttc agactatgct gacttttttg ctgatggctg taataaaata tatttttact   20580
ctaaatagtc aaatttgcct taaaatgcta aaatatttaa ctgaaccaaa ttttggttt     20640 tgttcctttt ttaaaaagtg taactctcaa attctcaaac aactctatac tccaatttat   20700
ttgactgtac tattggtgca gtggtccaca aatattctct aatacataca gtgacattga    20760
taattactaa tactactact aattttacca ataccggtgt tactccacta ttttccacat   20820
ttctcacaat accttgggtt gaaggtggag atcaatatag tagttttatt ttaaagtaaa   20880
atttagcact gtgttttcta tcaatctcgt aagcacatg tacattctat ccgtatcctt     20940
attaggactg ccaggactag actttgaaca gtaagagtct tgccttactt aaaatgagaa   21000
cattaccgga ttcgatggcg tccctgtaga ttcactgcta ctgcttcttt cacaacatat   21060
ctcccttatt acacacagag ccaggctttc atcaaaggaa agggaaatac tatcagattt   21120
```

```
gtggcgtttt ctttgtcgtt caccagataa ttcatctgaa ttttcttctg gatatgtaag    21180 gaaaaaaat aaattgctgt actgtgattt agaaaattga gctgttttga gtacctattt    21240
gtacagaaac ttagtttcaa taaaattagt tcaaaagtta acactgtttt attgaatctg    21300
tccaactgtt acagcagaac actatctgtg tgtatttatt tatttgttta tttatttatt    21360
gtctgagaaa gggtcttgct ctgtcaccca ggctggagta cagaggcaca atctcggctc    21420
actgcaacct ctgcctcatg ggctcaagtg atcctcccac ctcaacctca gcctcccgag    21480
tagctggtac cataggaacg gtaccatagg aatgcaccat tttgtatttt ttgcatagac    21540
agggtttcac catgttgcct aggctgagaa tactatttt aaaaagcttt ctattcttct    21600
ttcagaactt tatctccata catcacaatt taatctatct aataaagttt ttattaacca    21660
aaaaatctag gaattttttt ctgtcaaaac caaactttaa aatataagag ctcatctgtt    21720
tttttccgaa aagagccaaa gtgtttaatt tactcatatg gtattcttaa tgtttcaatt    21780
tcttcagtac cctacacttt ttcttttgag acagagtcac actcgaccac ccaggctgga    21840
gtgcagtggt acattctcag ctcattgcaa cctctgcctc ccaggttcaa gtgattcttg    21900
tgacttcagc ttccaagtag ctgggattaa aggtgcacac caccatgcct ggataatttt    21960 tgtattttg gtagagacag ggtttcacca tgttggccac actggtctca aactcctggc    22020
cttaagtgat cctcctgcct cagcctccca aagtgctggg attacaggcc taagccacta    22080
agcccggctc ttcagtaccc tatattttaa acagaaatca aaccagtaa aaagtttcca    22140 tttcatttta aataataaat tatctctgaa tgggtcagaa tgttagacaa atccgttaga    22200
cataaatgag aatactacct tatactagac ataaaaatga attccaggtg gattaaagat    22260
ctaaatataa agaacaaaac cattcaagta cctataacaa aatattctta taatgctggg    22320
gtggagaagt atttcataat actgcaaagt cctcaataaa aagactatca agattagacc    22380
atgtcaaggt ttacatgaca aaataaaata ccaaacaaaa gttaaaaggc aaaggtcaaa    22440
ttcgaagata atatctgcaa catatatagt aaaaattacc catagtatac atattataca    22500
aagtcctacc aaatcaagat agactgtatt ttcttttaag gaaacaggaa aaagcaagtc    22560
acagaagaaa tacaaatgac taataaacat atgaaaaatc ttgagtcatg tacttgagta    22620
atagaaaaaa aaactcttac ctcctaggga tcaaagaaat gcaaagtgaa atgatatcat    22680
ttttcaccca tgagaatgac aaaaattaaa atgagatagt atcacagatt tctgaaagga    22740 cttttttat catttcttg agacaaagtc tcactcttgt cccccaggct ggagtataat    22800
ggcacaatct cggcacactg caacctccac ctcctgggtt caagcaattc tcctgcctca    22860
gcctcctgaa tagctgggac tacaggtgcc caccactgtg cccggctaat ttttttgta    22920 tttttagtag agacggggtt tcaccgtgtt agccaggatg gtctcaatct cctgacctcg    22980
tgatcctccc tcctcggcct cccaaggtgc tgggattaca ggcgtgagcc actggacctg    23040
gccgggattt ttacgtttta tcgagatcac aagttctgca cgtgagttct taatcatgtt    23100
tgtgttccct atttttaaaa aggtgatctt ggccgggctg caattataaa taatgctgta    23160
attagtatct ctacatataa atctttgaat tttttattac atccttagga tagattacta    23220
gaaatggagt tactaggata atgttaagaa ctctaagact tttttttctt ttcttttttt    23280 tttttttta agagggagtc tcactctgta ccccaggctg gagtgcagtg gtgcgacctt    23340
ggttcactgc aacctccaca tcccaggttc aagcgattct cctgcctcag cctcccaagt    23400
agctgggatt acaggcgcct gccaccacac ctggctaatt tttgtatttt taatagagat    23460 ggggttcac catgttggcc aggttggtct cgaactctta acctcaagag atccacccgc    23520
```

```
ttcggccttc caaagtgctg ggattacagg tgtgagccac cgcaccaggc catctaagct   23580
tttttataat ccgaaaaatt taatcaattt ttacccactt ttaccaattt acagaccaac   23640
agtttatcag tgctaataca caagttatta gcactgatga gtaaggatga gtaaaaattt   23700
tatttttact aatttgatag atcaaaagga caccctttg  gcattttta  ctatctgtaa   23760
agctaaaaat caccaaaatt caccctctcc ccatatttat tagtcattcg tatttactgt   23820
gagaaatttt tgtgaactgt ctgcccttt  tgctatttga agttttaatg ttttccttat   23880
tgatttggga agacttttta tgtaatacag atattaacag tcaaatttaa agtgactatc   23940
tttcaaatat gttgtattct attttt catt taactttt aa actcatttga aattcatttt   24000
ggcataaggt acagatctaa cttcaccttt tccccaagta actaccattt gttctagttc   24060
cacctctgcc ctagacacct ctgcccttcc tgtcttctgc ccgcatgtac gagattctgg   24120
tctgggttca tttattctgt ttcactgatc tgacattctc tttcatctga atcatacggt   24180
cttagttact gcgacttcct caggcaacag ccttctcgtc tactacgtct actaactgtt   24240
ctcaactatt ttctctctgt caactatttt ctctctctct cttttttta  gacagtctca   24300
ctgtgtcgcc caggcggagt gcagtggcgt gatctcggct cactgtaagc tctgcctccc   24360
cagttcatgc cattctcctg cctcagcctc ccgagtagct gggactacag gcacccgcca   24420
ccacatccag ctaattttt  gtattttag  tagagatggg gtttcaccat gttagacagg   24480
atggtctcga tctcctgacc tcatgatcca cccgcctcgg cctcccaaag tgctgggatt   24540
acaggcgtga gccactgcgc ccggccctta tctcttcatt tctaaaatgc tatttacttt   24600
ctgttttaaa actcataggt atgtactacc atttattaaa aataacaatt taaaaattta   24660
actgttaagg tgactaagaa taatggtgaa aatagagttt atatgcctgt ctcctattat   24720
cttt ctttt  agacgaagtc tcacacggtt acccaggctg gagtgcagtg gcgcaatttc   24780
ggctcactgt aacttctacc tcccgggttg aagtgattct ccttcctcaa cctcctgagt   24840
agctggatta caagtgtgcg ccaccaggcc cagctacttt ttgtatttt  tttagtagag   24900
atggggtttc accacgttgg tcaggctggt ctcgaactcc tgacctcgtg atccgccagc   24960
ctcggcctcc caaagtgccg ggattacagg cgtgagccag gcgtgagcca ccacacccca   25020
gccacctcct actatcttaa cagagagttg gctaactata aactccagtg gggcacagta   25080
aactgtgcct gctgtagtca gccagaaaaa tattgctaaa taagcaattt gtaaatcaaa   25140
taaaatcacg aatgaaaaaa actcagaggt taattcatct caaccaaaaa aagggaacaa   25200
tttaattaag tctaaaagca ctaatttcat tagagaaaga atatcaaaaa gctgtgtgaa   25260
tgcgtcaaat aaatattcat atatacctgt ctcactaatt gctctccttc tagatgaggt   25320
agatggtcta gaaaccaaat gtgaagatga aggtttctct tcctgaagct cttgtacaag   25380
gtcctaagca tttaggaaaa aaataaaata caacaaactt aacataacca gtaagctaac   25440
ttgttgtaaa taacctttcc aatttgcaaa taatattaca ttagaatgag aaatttactt   25500
agattacctt ttgatcactc ccaccttcaa ggtgacacct gttctcactc acagatgtac   25560
ctgagtccga tgattctgag agaaaagaaa aaggatcaga aacttggtgg tgggcggggg   25620
gcggcggggc gctactcagt agatatgcta tcagtctaac acaaaccctt atgcaattta   25680
accttttcaat aaacattaaa catgtatttt ccaggtggca tcctcatact aaatgttgca   25740
gatgtaaata aaataattca actttaatgt agaagagtaa agtataatca agacattaaa   25800
agactgttag ataaattagc agagagacag gagagtcatt attttggtag ggacagggag   25860
tgtctgagaa acaaagaatc aggaaatatt ttgtaggaca atatgaaaat agggctagga   25920
```

```
aaggccattc cagaccaaga aaacgccatg tgaaaaagta tccaaaagca aactaacaac   25980
agttcctgtt gcaggacacc acaagcagtt cattattact ggaatgtagg caggttcaga   26040
ctgtaaagga tcctgtggtc tagccaaagc aggactcatg ctgtcattcc cttatcactg   26100
cattcttccc cgcagatact tcagaatctt ccttaatgcg atgttgcagc cactcaccat   26160
taaaaaggat ttttgtccaa gaaatgaaac tgatttctag ctcacagaaa atattacatc   26220
cagagagcaa taatgaaccc ctaaatggta attttaagca gaagagtgac aaatcactct   26280
agcaaaacat aagaaaaaga gggcagaggc aggaaaacca gtattagaca attgcaataa   26340
tacaaactaa aaactattaa agcctaaact aaggcatgga aaacaaattc cagagaaatt   26400
aaataggtaa aaaccaacaa gacctggtat tgatataga aggcaaggaa gaaaggagtt   26460
aagatgattc caagattcca acttgggtga ataaatgagt ggtaccattc actaaaagag   26520
aaactttaga aagataaaca gattggatgg gaagataaca aactgagtta ttcaggcaca   26580
taggtttcat ttgtagttgg atatacagac tttgagctca aaagtcaaag tttcagagtt   26640
gggatataca gacaattatc atcaaatacc ctttactacc cccttggaa acattttcat   26700 cttaacagtg aactcatgcc tggacattaa cattttgaaa ttatgcatta tcatagatta   26760
attttctctt tatactatgg gtaaggcatt acactaattt tcttaagttg tacataatag   26820
gttatattgt ccaggaattt tggattagta taaacagatg ctacaaaaaa gatgtaataa   26880
aaaggaagcc ctaggctggg tgggtgcagt ggctcacact tgtaatccca gcactttggg   26940
aggccaaggt gggaggatca cctgaggtca ggagtttgag accagcctgg tcaacatggt   27000
gaaacccttt ctctactaaa aatacaaaaa ttaaccggac gtggtggcag gcacctgtaa   27060
tcccacctac tcgggaggct gaggaaggag aatcacttaa acccgggaag cagaggttgc   27120
agtgatccga gatcgcacca ctgcactcca gcctgggtga cagagtgaga ctccatctca   27180
aaaaaaaaaa agtgacaaag ttgagaacat ggaataggag ttctgaagtt aattctactg   27240
atatctaaac caaactcaga ctgcaaataa gtaatttgta agtttccatc tcaataatac   27300
aattttctta gtaatgtgcc aaagtttatt taaacaaatg aaggaatgaa tacatcaggg   27360
ttacatactt cagaaaactc aaactactac tacaaatact acaattgtat atttagctat   27420
cacacaattt cttaaagagc tttaaaacaa caggtataca tatgtaacca acctgcacat   27480
tgtacacatg taccctaaaa cttaaagtat aataattaaa aaaaaggaa ataaaaagga   27540 tacaatctaa agctcaaaaa aaaaaagagc tttaaaacaa taaaatgcca aatcatcagc   27600
ctaataacta cttttatttt gggataaaat ggagatactt ttctgggctt taaatcctaa   27660
ctttggaaga ataagtattc aattcaacac atttattaaa taccatatta ataaaacact   27720
atagtgtgtg atgcacaatg caaacctgaa taggacacag gtaacaaaaa tataaacaag   27780
tgcaacagcc agacgcagtg gctcatgcct gtaaccccta aactttggga ggccgaggtg   27840
agaatatctc ttgagctcag gtcaagacta gcctgggcaa catagcaaca ccgtctctac   27900
caaacataca gaaaaattag ccaggcgtgg tggagcacat ctgtagtccc agcaacttgg   27960
gaggctgagg gggaggatca tttgagcccct ggaggtggag gatgcagtga gccaagatta   28020
ccactgcact tcaagcaggg tgacagagtg agagcccatc tcaaaaacaa acaaaaaaac   28080
ccacaagtaa aacaaagcaa ttttacaata aaatctgaat atggaataga ggaagtacaa   28140
gggagtggtc aattcattct aggaactaaa caagctcctg agaggtgttt ttttgttttg   28200
ttttgttttt gtcttttttta agagatgagg tcttgctctg tcacctggac tggatggcat   28260
gatcacagtt cactacagtc ctgacctccc agcctcaaaa aatcctcctg cctcagcctc   28320
```

```
ctgagtagct aggactacag gcatgcacca ctataccaag ctgattttg  tagttttgc   28380 agagttagga  ttttgccatg ctgcccaggc tggtcttgaa ctcctcggct caagtgatcc 28440
tcctgcctta  gcctcctaaa gtgctggaat tataggcatg agccatcaca cctggcctaa 28500
gagcatttct  taactgtagt tcgaggatgg gctttaggag cagtgtagtg tattagagac 28560
agctctaagc  agcactcaaa agcaaactgt gagaccgggt gcagtggctc atacctgtaa 28620
tcccaggact  ttggaaggcc gaggcaggca gatcacaagg tcaggagttc gagaccagcc 28680
tggccaacat  gctgaaaccc cctctctact aaaaatacaa aaattagccg ggcgtggtgg 28740
catacgcctg  tagtcccatc tactcgggag gctgaggcag aagaattgct tgaacctggg 28800
aggcggaggt  tgcagtgagt cgaaatcatg ccactacact ccagcctgag tgacagagca 28860
agattccttc  tcaaaaaaaa aaaaaaaaaa aaagcaaact gtgtacatct cttcccaact 28920
ccatgttttt  agccttcaaa tgagagtatt atactatgga agtcagcaag cacataaatc 28980
agggcttttc  tcatggaaag taggttgtaa aacacttatt gacttaccca tgtatatata 29040
catgtgcatc  tttctggaac aagaacccaa tgcttttatc agcttattaa agagagatgt 29100
gacccaaaaa  taaccagtta agaaacggaa gtaggaacat aaaattccac ttccacaaat 29160
tggtaaacaa  aattttgtct ataaccaaag aaaaagactc atccttcatc cttacacatg 29220
gtcctaccta  ggtaacaata ttatttccca aagcctttca atacattttc aaggtagatc 29280
actcctaaac  aggagctttt gaaattacag accttccaaa ataaatccta actctgatat 29340
cccaagtcta  aattgatcta acaggatatt taacttacca ttagaacctc agtatgtggt 29400
tttagttcat  atgtacttct aataaattta tcatactttt attacaatat ttaattaaag 29460
caacttttaa  agagaatcac aattataaaa catatgcaca taaacaaaaa tgtcttttaaa 29520 acgttttat   ggtatttatc catgatgctc aaaattaact taccctgctg attgactact 29580
accaagttcc  tgtagatcat ggtatatatt ttccttgtag acagaaaaaa aaaaaataac 29640
aagagatgta  cattttagaa taaaaatttg tattaagctg gatctaacca gacttctaca 29700
tacatactta  gtatgaacta ctgcacacat tcaaaaccaa atttatcatt ggcaagcttg 29760
taggcactta  aaagcacaat aattagtagc acaatgatta tgtacagcta cttttaataa 29820
ttactaaagt  ctctctagct gaaagatttc acactaccaa ttcctgaaat gtgctttgtt 29880
tggactttac  cagaagaccc ccaaaaaatg agtatgcaag caggaagagg ttgaacatac 29940
ttattttcaa  acaggaatgt ttttagctct gtgcttagta gcaaactgcc aaaaaaaagc 30000
attgagttat  gcaaaatcca ttaaatacaa actgccaaaa aaactattga gttacgcaaa 30060
atccattaaa  taggaatttg attataatct tgactttcat caagcttcaa cttcctttct 30120
tgatcttaaa  acgtattaac agaggccggg cgcagtggct cacagacacc tgtaatccca 30180
gcacttcgga  aggccgagtc cggcagatca cccgaggcct ggagctcaag accagcctga 30240
ccaacatgga  gaaacccccat ctctactaaa aatataaaat tagctgggca tggtggcgca 30300
tgcctgtaat  cccagctact caggagactg aggcgggata tcacttaaa cccgggaggc 30360 agaggttgcg  gtgagccaag atcacgccat tgcactccag cctgggcaac aagagcaaaa 30420
ctccgactca  gggaagaaaa aaaagaaact tattaacaga taaagcagta ctcattcatt 30480
caataaatac  agactgaaaa cctaccacgt accagtcact ggtactatgt accagacacg 30540
ggggaaaaca  aagaatgaaa cagaaatgta tatgccctca tgaagtttat atcctaacag 30600
gaggataatt  catttacccc agtattcgtt gatgtcacaa tggattttc  cttttgtttt 30660 taaactaagg  atttaagaga gtgtttgtca caaaatattg tttctcactc aatattaaga 30720
```

```
ggaaatatga atcccaacta tcttttttca tccttgggaa taaggataca gcaacctaaa    30780
cccacaatat ttttaattca tatccttttc aagtcagtaa tttctcctat ttcttatctc    30840
tcaacattta gaattcaagt ccaaggaaat catacttcca aacattatcc gaagattcaa    30900
tattcagacc aggcacagtg gctcacgtct gtaatcccag cactttggga ggccaagaca    30960
ggcagatcac ttgaagtcag gagttcgaga ccagcctggc caacatgca aaaccccatc     31020 tctactaaaa atacaaaaaa ttagctgctc atagtagtgt gcacctgtaa tcccagctac    31080
tcaggaggct gaggcaagag aatcgcttga acccaggagg cagaggttgc agcctgggca    31140
acagagcaag acttcatctc aaaaaaaaaa gaaaaaaaat agaagattca atattcaata    31200
ggtaaagaaa tcaccaatat accaatatag ttattttaa aatttataaa attaaaccat      31260
atataccaag gccacgtata aaatgacaac atatatggat attaaacaga agtgactcat    31320
caataaaaaa taataattat acatatattt gtaatatata taattatatt atatgtatat    31380
tataatatat aatatacaaa ttataataca aattaagaag ctagatgaaa tttaaatata    31440
gtactatatt cataactagg ttaaaacaca cagttgcaca taatacacaa atgactggta    31500
aaaatacctt ttgttaacaa actacagtcc ttttttttcc tttactttc ttagttttct      31560 gtcatctcct aatgttcaat aataatatat actatgttta caataataag gttgttttaa    31620
agttataaaa tcccttgctc agctgaggaa gttatgtttt ttaataaaat aaaatcccat    31680
ttaattatca tcttttcagc tatactattg agcattaaat actagcagaa gctagttaat    31740
tgtctcaggt gaacgtattc attccattta ttaatgtaat gaatgctaag gctcaacacg    31800
gattgcctgt gctaaaccaa atgtgacaaa gaattccaaa tgtaggccgg gtgtggttgc    31860
tcacatctgt aatcccagca ctttgggagg ccatggcagg tggattaccg aaggttagga    31920
gctcaagacc agcctggtca acatcgtgaa accctgtctc tactaaaaat acaaaaatta    31980
ggcatggcag caggcacctg taatcccagc tactcgggaa gccgaggcag gagaatcact    32040
tgaacccagg agacggaggt tgcagtgagc caagatcatg ccactgcact ccagcctggg    32100
ccatagagca agactccctc tcaaaacaaa caaacaaaaa aaagaataat tttagaaaaa    32160
tatatattaa aaaaattttt ttttcagatg cagttttgct cgttgcccag gctggagtgc    32220
agtggcgcaa tctcggctca cctcaaccac aacctccacc tgcctggttc aagtgattct    32280
actgcctcag cctcccgagt agctggaatt acaggcatgc accaccacac ccagctaatt    32340 ttgtatttt agtagagaca gggtttctcc atgttggtca ggctggtctc caactcccaa     32400
cctcaggtga tccacccgcc ttggcctctc aaagtgctgg gattacaggt gtgagccacc    32460
gcaccaggcc tatttctaga aatattacct gggttaaatt ctgctggtta agtgccataa    32520
tgataggtga caatgaaaat gatctccaaa ataactaagg ctcaaatgta agcctttacc    32580
acgtggtggt atactgtttc tggaataaaa agttataata gctacagcta atacttgaat    32640
gctttgtatg tgcccaaaac tatgcttttt tatacaacgt ctctcttcaa gagctttaac    32700
ctccacatga agtatttaat tatccctatt ttataaatgg ggaagcaggt ttaaaaaggt    32760
taatttatct agtcacaaaa ctagtaaatg attgggctag gtttcaaaca ctggtttata    32820
agatgccaga gctcaggttc tcaaataata tgccgcagag ctaaaaaatt aagtttcagc    32880
atgtctttaa tatgtttcaa cagttttct ctgacaaaag tgaatgaggg tagaggtgaa     32940
ctgaaatgtt agcccagatg gcttttaca atggactaaa ctgaagaatt acctgtgctc     33000
tttcacagag aagcttggca cgccaaacaa atctcctaga agatcatttg aacaatatac    33060
aatatgttgt tgcttctcat catataatcg tttagtcata atatactggc caagataaaa    33120
```

```
aagaacctga aatacaaata tgatttctga gcattaaaga aaactaaatg ttagttgtaa    33180
atacatttaa taatatccta tttatctgaa tagggGtaaa caaccaggaa ccatatccac    33240
aactatgtag aacaaccatt ttgtacttag aagctacttt tggctgggcg cagtggctca    33300
cacctgtaat cccagtactt cgggaggccg aagcggatgg atcacgaggt caggagataa    33360
agaccatcct ggtcccatct ctactaaaaa tacaaaagtt agccaggcat ggtggcagac    33420
acctgtaatc ccagctatta gggaggctga ggcaggagaa ttgcttgaac ccaggaggtg    33480
gaggctgcag tgagccgaga ttgcgccact gcactccggc ttaagcaaca gagtgagact    33540
tcatctcaaa aaaaaaaaa aaaaaaaaa aaaaagctac ttttaagcct tttccattta     33600
atttgacaga agcagaaata actgcttctc tatttactta agcaaacctt aaaatgtgag    33660
gtttttttcc ttgtagactt taactctgcc cagatactta gatactaaca tattaggaag    33720
ggaaaaggca gcaaaataaa aaactgtatag ccaaaaagt tgcagaaaca aaaatcaact    33780
aaaatatggc agtggtctgg agccacttag taaatagtca taaatactat aaacctcaat    33840
agcctctgag gtcaccagag gaggaagaca gaaaaacaat caatcaatga cagctacaaa    33900
acagtttgag agaattctga gaatgaaata aaccctctaa ggtatcaatt tactccatat    33960
tatgataaat aatcaaaata atgactttga accattaata aaagttaaat tatattccct    34020
gtgctgcatt aagacaagaa gttggcaata cattttttaag atatccagat ataaacctat   34080
taacaactac ctaaatacat atggcatttt acagtttaca atgtactttt ataagtatta   34140
tctcattctg atatttcata agattattat cactgtatta gaaatgaaga aattgcgttg   34200
ggcacagtgg ctcacacctg taaatctagc actttaggag gccgaggtaa gcagatccct   34260
tgagcccagg agttccagac cagcctgggc aacatagtga aactccatct ctacaaaaaa   34320
atacaaaaat tagccaggca tagtggtaca agcctgtagt cctagctact gcagacactg   34380
aggtgggagg atcacctgag cccacgaggt ccaggctgca gcgagcagtg atcatgccac   34440
tgcactccag cctgggcaag agagtgagaa actgtcacat aaaaaaaaa aaaaaaaaa    34500 aaagaagaa gaaactggcc ccagctcttc tgactcttaa tccaacgctc tttttactac    34560
ccatactagc tttcactacc ttcctgtgtg ccccagaaca aagatcctat aactgagaac   34620
tatatcagac aatacataca ctactgttac atagtttagc ataagcattc taagtctttta  34680 tgatggcctt ggccaatttt ctcatttcta tctactgcta aatccatact tttttgtttc   34740
cttaactgat tatccaatga taataaggtc aatcccaaat tagccttaaa ataccatttt  34800
aacctggccc tttcctacaa acactgtctt tggatttaac tggctaagca ggcatcggcc   34860 ttaaggaat attcttatgt gactgtggat tggacagatt gctgtccagc agtgggaaag   34920 gaaaaggaa gagaacttag atttattcta ccaaacatcc tttaaggaag tttctaaaag   34980
tatagctgga gaggaaaaag aaaaatggaa gctcttcctg ccccactata ccgttgtaag   35040
aaagaaactt aaatgttttta agtaatctga gtcccataaa ctaagtggga gagacagaga  35100
acaggcatat ttcaatcaca ctgaaattct gcctaaggtt gctcaatctg tcactgaaaa   35160
tcatgcttct gtgcacaaat ttaaaggtgg ggaatgcatt aaaatgctgg aaccattaga   35220
tagaatatat ggtcatgaat cagctcacct ctatcccaga aagatcagta tactgtactc   35280
atgtatctct agtgcagaag ttcttaacct gggatccagg gatgcccaag aagtccttgg   35340
atagaattca gggggtccat taatttggat gggaaaaaaa aaattctatt cttattttca   35400
caaacttcta actagaattt agcttttcct tcgattataa atgtaggcaa caaatcacaa   35460
cagtattaat acctgtgatt tcatcaccaa caaaaatcag aggtgttttc ctatcatact   35520
```

```
gtacttatgg caaacatttc aaaatatgac ttatattcct cactatatca agataatatt   35580
tattggccag gcatggtggc tcatgcctat aatcccagca ttttgggagg ccaaggcaag   35640
tggatcacct gagactagga gttcaagacc agcctggcca acatggagaa acccccatctc  35700 tactaaaaag acaaaaaatt agccaggcgt ggtggcaggt gcctataatc ccagctactt   35760
ggaagggtaa ggcagaagaa gggcttgaat ctaggaggcg gaggttgcag tgagctgaga   35820
tcgtgccact gcactccagc ttgggtgaca gagcgagact tcgtctcaaa aaacaaaaaa   35880
acattatatt tattatatct tcttctaaat cttagtattt attatgttaa taacaaaagc   35940
acacatatca caaactagtt tactattttg gtaaccgtat tttagtatgt ttcctttgta   36000
attctataca ttttatttca tacatttaaa aacatgattc tgggaaggag tctaccaaag   36060
ggttgacagc ataaaatggt caagcaccct tacggggctt ccatttatct gagttcctag   36120
ctgagaaatg aaactcgagt ataattagaa ttttcagctt taaaatatag tccaaacgac   36180
cacaaaatta aatgttgctg cttaatgaaa aatccttcta tatggccaat ttctccacat   36240
ggtcttgaaa actttaagta tggctacatg taactagtga gatactactt atctcttgat   36300
tcagcttacc tctttcatag tataagtgtc tttttgtgca ccaacagact ttaataactt   36360
caaaagcaat ggctttggtc taacctataa agagaaaaga actgctatta tacttccaaa   36420
attatcccag aactataggc cctgcagcaa acatatccat caagttcaat aaaggggatt   36480
tggaaaaaat gctggggagg atcaatcat tatgcaagta tcatggaatc atcaagtatc    36540
agttgtgatc acagacagta tccaatccaa aagagcaaag attacttttt ccttcagcta   36600
tttatattac ctgcttactg ccttacaaac aaccataaat tactgagatc caatgagctt   36660
accgtactga tccaacgagc ttattgcaag ctaacttaga gaatcaaaga gaatgaata    36720 aatctttaga gtgggtcctg ttatcaatct tctctttcta aagattaggt tcctgaaggc   36780
tagagaacct aactaactaa cccaagctga caagggtaat taagaacaga tcagagataa   36840
caacccaggt ccctcaacta caactcagca ttttcttcct actatatcat gctgcctctt   36900
agttagtcta catttcaaat atctacttga caaacattta ttgagcttct actatgcact   36960
ggacagtggt aggtactgca aaagaaatta caaataagac atatgacctg tatgcaagga   37020
gcctgccaac tagattaggg gtcaattttt ttctgtaaag agccagactg taagtatttt   37080
aagcttttca tacaaatggt tctatccaag taaaaagcat ggctactatg taaaccaacg   37140
ggcatggttg cattccagta aaattttcct tacagaaaga aaggcagctg gctgggagag   37200
gtggctcttg cctataaccc cagcactttg ggagacagtg ctagaggttt gcttgaggct   37260
aggtgttcaa gaccagcctg gccacactg agagactcca cctctacaaa aaaatttaa     37320 aaactaaaac aaaaacaggt aacaggccaa agttggctga caggctaaca tttgcctgcc   37380
ccttatctag aggttttaca aatggtcttg agaaaaataa ttgtcatggg ggaggggaat   37440
gtaatatact atgcactttc tcccttcctt ttggtttatc aaaatctgca aaactcaagt   37500
atctttacag cttgccacta ccacacaaac tggtacctct gcacctctct ttaatatgcc   37560
ccggtcctct gtctaacttt aaaatctgac agcaccccca ttggggatgc cttaaaaaca   37620
gatttttaaa aattgcctat ttccagctaa tcaataaaac aaatattatt taacaattga   37680
aaaatttaaa atacatatag aattgaatta ttaattttc tgatcacttt ttttttttt     37740 aactgtgctt acatatgcac tttactttca ggctaaagaa tggactctct caaaaaagat   37800
ttaaaaataa cctttttttct cctgaatttt tattatatgc tatattagct tcaaattaga   37860
taaaataatt caaagtaaaa atctgtaatg gaagccaggt gcagtggctc aggtctgtaa   37920
```

```
tcccagcact tgggaggcc gaggcaggca gatcacctga ggtcaggagt gtgagaccag   37980
cctggccaac acagtgaaac tccgtctcta ttaaatatac aaaaattacc caggtgtggg   38040
ccaggcgcag tggctcatgc ctttaatccc agcactttgg gaggccaaga caggcagatc   38100
aggaggtcag aagttcaaga ccagcctgga caacatggtg aaaccctatc tctactaaaa   38160
gtacaaaaat tatccgggtg tggaggtggg tgcctgtaat cccagctact cgggaggctg   38220
cggcagaatt gcttgaaccc aggaagcaga ggttgcagtg agccgagatc atgccactgc   38280
actccagcct gggcaacaga ccaagactca gtctcaaaaa aaaaaaaaaa aaaaaatctg   38340
taatggaaag ccatcagtat attagtgact taaaagacat gtattaatga gaaaacagct   38400
ataaaagata atagcatttg taatcttaca ttgaagaaca agaaggtaaa ttacaggtga   38460
agatctaaat atttaaaaaa tttaaatcta gaagaaaata taggaatata tttgcaagat   38520
cttgggacag gagagttctt ccaaagcatg atatgaaatt caaaagccaa caaattttac   38580
ttcacagaat tgttctcaat ggggaaaaga caacataaaa ttaaatgcta cattagtaaa   38640
caacaaaagt taaatatact tgaaacacat agagctactc caattactaa gaaaaatttt   38700
aaaaaactaa aaggaaaatg gacagataag actaggcaag tcccagaaga aataaatgac   38760
ttaacaaaat ggaggcctgg tgcagtgatt cacgcctgta atcccagcac tttgggaggc   38820
cgaggcaggc agatcacctg aagttgggag ttcaagacca gcctgaccaa catggaaaaa   38880
ccccatctct actaaaaata caaaattagc tgagcgtggt ggcgcatgcc tgtaatccca   38940
gctactccag aggctgaggc aagagaatcg cttgaacccg tgaggcagag gttgcaatga   39000
gacaagatct cgccattgca ctccagcctg gcaacagga gtgaaactct gtctcaaaaa   39060
aaacaaaaac aaaacaaaa aggaaaggtg cccagcctca ccaagaaact agagaaaaat   39120
gaatttaaac aatggtacag tacctttat caaaaaaata gtaataataa taaagaggc   39180 caggcgcagt gactcacgcc tgtaatccca gcactttggg aggccgaggc gggcggatca   39240
ccaggtcagg ggatcaagat catcctggct aacatggtga accccgtctc ctactaaaaa   39300
tacaaaaaat tagccgggcg tggtggtggg cgcctgtagt cccagctact cgggaggctg   39360
aggcagggga atggcgtgaa cccggggaac ggagattgca gtgagccgag attgtgccac   39420
tgcactccag cctgggagac agagcaagac tccgcctcaa aaaaataat aataataata   39480 attaaagatt ggtgatattc agtattggca ggagtgaaac tgttagagcc ttttggtgag   39540
caagttacca gtagcaatca aatagtaaaa ttgagaactc aggagttcta attctctaaa   39600 atcttttct tttcttttt tttttttag acggagtttc gctcttatcg cccaggctgg   39660
agtgaaatgg cgcaatcttg gctcaccgca acctctgcct cctgggttca gcgattctc   39720 ctgccccagc ctcctcagca ggggattata ggcgcgcgcc accatgcccg actaattttt   39780 gtattttag tagagacagg ttttcaccat gttggccagg ctagtcttga actcctcatc   39840
tcaggtgatc ggtccgcctt ggcctcccaa agtgatggga ttacaggggt gagccaccga   39900
ggccagccta taattctata aaatctttct tacagaaata gtcacacggg atgcatgtac   39960
aaagcggcac tatctgtaat actcaaaaac aggaggcaat ttttaaaaac ctatcagtaa   40020
aggcataaat aatttttaaa atggtatact catgctgtgg aatactatgc agccattaaa   40080
aagaattctg tagactttat ttattgacaa ggatgcaagt cacagaacaa ctacagtttc   40140
atcttgttag tacaacaaac aggacaataa catagattta aattcaaatg taaatatatg   40200
tgggtacgca cacaaaaaat ctaaaaggaa acatggagca aaaagcctgg aattttcagg   40260 ttttactttta aaatttctct aatgacaaaa atctttaaaa caagcacgaa taacttttt    40320
```

```
gactttttaga aaccattttt aaaaattaaa tactgggagg tcaaaaagga aaaaaaaatc   40380
agtcacgtaa caaacgtaac ttcaaccacg cttaacaatg taatggaact aattttttaaa   40440 gcaaatgtgg caaatggcta aaaaaatact gaccagttct taacagtttt taactccacg   40500
cagttacgcc agaggtagca cactttaagc tatgcacata caattttatt tacagagcca   40560
tgctacaatt gaggtatacg aaatttagtt tatcacttca taaaataaat tattcttaaa   40620
agttacacga gacaaaaata ctaaccaggg tctcttgttc cgaagctgga atctgtgagg   40680
tggttacagc accatcagta ggtacagaca tgttggtatt gcacatttgc ctacaaggaa   40740
aaaaaagaca cgatgaaaac tggaaatcat gaaacatctg tggaaaatac atcatatata   40800
aagaacataa acaacagtta aaactaaagc tacaagcaag tcggtgctta cctggatcag   40860
cagagaaaaa gtggcgtgcg tccgtgccca caggtctacc ctccaatcgc cactgaacac   40920
agctgggaaa atgcatggtt taaatagccc cagctggaga caagtcagga cttaactcct   40980
tttactgcag tttcggaacg tgtctgaact tgaccagctc aagaggaaaa gctgagtcaa   41040
cctgcccact gaaccggccc aatcccgccc agactacgcg cagcgttcac actagtgacc   41100
cgacaggcac ctgcgatcat ccggacctcc cgcgccaag cggccccgca gccccggcc   41160 cccgtgacct ttaccctgaa ctcccgcgga gacctccgaa ccaccccac ccccaccgcc   41220 gcgagagccg tccgaaatcc cgccctcctc cctggcggcg actgcctagc cccagtccaa   41280
caaaacctcc gcaaagccac gtgccccatg ccccgcgccc cgcgcccga gccccagcc   41340 acgaaccgca caaggctgc gaacgggcag aggctgggaa ccagcgatag aggggacacc   41400
gtcagagccc agacccaaaa gtgaccgctc gctgccgggc cagtacctgc tcctcaccat   41460 ccgggggtttt cgcgcttgga gtcggggtc cctcaagact ccccagtttc cttcacgggg   41520
cgcgcggaag cacgacgccc tgggcctcgg ggatcattcc actctccggg ccagggcact   41580
gggcgctcgt acgcactaat ccggggaggg acggtgctcc tggctgcgaa agcagcagga   41640
tctcggtcag aggggtcgcg gccgcccctc gggctcggct tcttgctcca tctttccgac   41700
acacagggcc acacaggccc cagaagcagc caagctcgcc gcggtgcctc ggtgcgcgcc   41760
ccctaccgcc cgaggggagc gcgcgggtcg tcgcggcgca tccgggcatt tgtgcgcgcg   41820
cacacaaccg gccccgcttc cgccaattgg gtcggggct cggccgcacc acctccggga   41880
tgatggagtg gggggtgtcg ccccgcgggc gcggcgggct gtgaggcggg gtggggtgt   41940 tggccgcgag ctgagagggt ggggctcggc ctggcgcgga gccagcaagg tttggcgctg   42000
tgacactcct ttagccgttg cgctatgttt gtatttcttg tgtttacact tcccgcccgc   42060
ggtggaaact gcgacaaatg cggatctccg tgtcgctgtt accaaaaaga aaccaaaatt   42120
aacagctgtt taatatatta agcccactcc accagccgct ggagttgtac ccaaatgagt   42180
tattttaagg cctgttttta aaaagatta aaaatagcac ttaaggcagg cttatacacc   42240
ggtgcataca gctgttctgg ttggagaacg aagatgctgg ttaccgttgg cggggagggg   42300
agcggttact ctgcgctttt agaatgtttg ggtttggctg ggcgcggtgg ctcacgcttg   42360
taatcccatc actttgggta ggccgaggcg ggtggatcac ttgaggtcag gagttcaaga   42420
ccaacctggc caacatggga aacgccgtct ctactaaaaa ctacaaaaat tagtcgggcg   42480
tggtggcggt cacctgtaat cccagctact ctactccgga ggctgaggca ggacaatcct   42540
gtgaacccgg gaggcagagg ctgcagtgag ccaagatcat gccattgcac tccagcctgg   42600
gcgacagggc aagactctca aaaaacaaa acaaagtttt gggtttgtta atctacacat   42660
tcattatcat taaaatatat acttatatat tatgcactca ttctgactca cctactttcc   42720
```

```
cacagagatg tggcaaaaac gttttttgatg cggtctcata aattgaggac ataaagaatt    42780
gagttagcta aacccaaaaa cacagccatt gcaaagaagg aacacgtttc ttctctggcc    42840
agtaagtgat tagctccttg tgaacaagga cctttttta taaagttata tccttccctt    42900
ctgcagcttt ttttttttta taaagttata tccttccctt ctcccgcttc ccagcctacc    42960
agaaaggaaa cttccttaaa catagtggtc actcagttga tttaagttga ttgccaatat    43020
tattaactta agagatttaa tatgtggctt ttaaaaagat aatctcatct tcatcagatc    43080
atatacagtg gggtttctaa tagactcagt gcttgaccct ggatgaaaga aaatctcaag    43140
cagtgagaaa atgtaagcat gaaaagataa gtgataggct gcgcacggtg gctcacgctt    43200
gtaatcccag cactttggga ggctgaggtg ggtggatcac gaggttagga gttcgagacc    43260
agcctggcca agatggtgaa accttgtctc tactaaaaat acaaaaatta gccgggcccc    43320
gtggcgggcg cctgtaatcc tagccacttg ggaggctgag gcagaagaat cgcttgatct    43380
cgggaggcag aggttgcagt gagcggagat cgcgccactg cagtccagcc tgggtgacag    43440
agcaagactc catctcagaa gaaaaaaaaa aaaaagaga taagtgatag aggttgatat    43500
ttgttaaata tcaagtgaac gaatgggttt gtgctataaa agttcagaga cagaattaat    43560
tgcttagtaa atgctggagg cagttcacaa aggcctcaga gatcacacat attttgtgtc    43620
ttgaaagatg gtgagactta aataaaagca gagaatattc caggcacaag aaaattatca    43680 aaaatacag aaaggaaaat ataagaggac tgtttgagat acaataaata aatccgtttg    43740
acttgcatga aagtcaagaa gaagttttaa gaacttggag tctccttaaa tgccaagcaa    43800
ggaaatttgg gctttcgaca gagtagacat tagaagcata aaaacaagtg atttgcttca    43860
aactgtattt taacaggacc accaagagta gattcaaact cagaatagtc gggccggctg    43920
ccttctggac cgactttccc ccttctcatt ggccttgtgc tttgaaaaaa ttatcttgac    43980
aaaattatta gagcagaaaa aaaaaggcag aactgataag attagtccctt ttctaatgga    44040 accagaaaag aagggtcaga atgaaggca gaagggagaa gcgggggtgg gggagagaga    44100
gagaagtaaa aaggattcac tcaagaacct ggtattcaaa actacgtgta ccagcactac    44160
cacagcagta tgactcagtg tccacctaaa gcatgatgat actgcttacc aaaaaagtc    44220 tggagggaat gaaagttgg gttagttta agttatgggt cacagaacag aattcggtgg    44280
taaaaagctt aggctgggaa cagagcttga aacagcaaag gaatgagagg aacgaccaaa    44340
aagccaagga ccatatagtg atgtctgaaa aatcagaatc aggtaataat attgaatact    44400
gcaaaagtca gagaaaatgt ggaaataaga aagcaagcga tctggaaagt ggcgagtaag    44460
atggaatatg aggaggttgc tgagagctgg gaggagacgg cagacagcgg ggaaatagac    44520
gtctggaaaa aaaactgaag atcacacaga aagcaggaaa ttcaaatctc ccaaagtgcc    44580
cattgtgatt caggatgata atttccccc gggaccccct ccacaggtcc gcatcctcaa    44640
gaggcccacc agcaacggtg tggtcagcag ccccaagtcc gctagcaggc ccgcccttcc    44700
agtcaagtcc ctggcacagt gggaagccga gtacaccgag gccaggaagc ggatcctggg    44760
cagcgccaac ccgaggagaa gcaggagaaa cccatcctcg ataggtcttc ctctgatctt    44820
cttcccttca ggccaaccag gatctcctaa cccgaagaca gcagacagcc caataatgtg    44880
atcagacagc ctctgggtcc tgatgggtca cacggcttca aacagcgcag ataaatgcag    44940
gcaagaagag atggcgcgac tgccgcgtca acgcgtcctg ggtcgtccgc caagggttgc    45000
actaccgtgg cagacagctg gacttgagca gcggaactt gacttacttg cctggtgatc    45060
cccgttgctc cgcccactgt gaccttgaat cccatgcact gtgacctccc cccttctcct    45120
```

```
ccttcccact gtgattggca ctttgacaag gactgtccca agtcaatgga aagggaaaaa    45180
gggtgagggt taggagaagg ttgggggaa cccaccaatt actcagagta gagagtcaga     45240
cagggccagc aatagcggtt tatcatgctc attaatttgg gatttcaaaa cacaaatgaa    45300
ctcacaccta cccaccccca agtgcatgtc atcacttaaa aagtgagttc catttgaaaa    45360
aaaagaaagc aaactacctg ctcactctaa aagcagttgc tgttgtttgt gactttgcca    45420
tttaaaaaaa tacagaccag ctgctgctgt ttgcttgcat tccacagtta tcttgtgtca    45480
ctttgccctt tgttgtgctt acttgaagtt tctctagagg caaactgctt atttctagta    45540
gcgttgttct tgatgcccaa gaggtgttcc aagaggttga gatactttga gtgtctttat    45600
attctctggg acctaaactc tgcaaacaag gctcacacct gtaatcccag cactgtggga    45660
ggccaaggct ggaggatcta ttgaggccaa gagtttgaga ccagcctgag caacatggcg    45720
aaaccctgtc tctataaatt gcaaaaaaaa attagccagg cgtggtggca ctcacctata    45780
gtcctagcta cttgggagcc agagctggga ggatggcttg agcccggata ggttgtggtg    45840
tgatcctgcc actgcactcc agcctatgtg acagagtgag accatgtctc aaggggaaaa    45900 aaaaagtct acaacagact tatcttgacc caagggccac ttcgtacttg tatttattag     45960
tcataactaa tcttttgtct ttcttttttt ttttttttg agacggagtc tcactctgtc     46020
acccaggttg gagtgcagtg gcacgatctc agctcattgc agcctccacc tcctgggttc    46080
aagtgattct cctgcctcag cctcccgagt agctgggatt acaagcttgt gccaccatac    46140
ccggctaatt tttgtatttt tagtagagac gggatttcac tatgttggcc aggctggtct    46200
cgaactcctg gcctcaggtg atccacccgt ctcaccctcc caaaatgctg ggattacagg    46260
cgtgagccac tgtgcctggc cacaactaat cttttaaagca tggtgaaaac taaacaagat   46320
ttagctcaga aaccgtgttt agaatgctga gtttcacaat atttatgaga ccatctaaaa    46380
ttacagaagt agttcaaatt ccttatgtct ttccaaacat ctggaactga atagtgttat    46440
ttaaaaggca aaatccgggc cggacgcagt ggctcacgcc tgtaatccca gtactttggg    46500
aggccaagac aggcagatca ctgaaggtca ggagtttgag accagcatgt aaaacccgt    46560 ccctgctaaa aatacaaaaa ttaggcgggc atggtggtgc aagcctgtaa tctcagctgc    46620
tcgggaggct gaggcagcag aatctcttga acctgggagg cagatgttgc agtgagccga    46680
gatcgcgcca ctgcactcga gcctgggcgg cagagcaaga ctctgtcctg gaaaataaaa    46740
aagtaaaaaa taggccgggc atggtggctc atgcctgtaa tcccaccact ttggcagggt    46800
gaggcgagtg gatcacctga ggccaggagt tcgagaccag cctggccagc atggtgaaac    46860
cctgtctcta ctaaaaatac aaaaaattag ccgggtatgg tggtcacgc ctgtaatccc     46920 agctactcca gaggctgagg caggagaatt gcttaaacct gggaggcaga gatcatgcca    46980
ctgcgctcca gcctgggaga cagagtgaga gtgagactcc atctcaaaaa ataaataaat    47040
aaataaagta aaaataaaa agcaaaatcc cagcaagtag tgaatacaaa gactttttgt     47100
ttttactttg aaaattaatc aacttttttgt ttgactgaaa catacagaaa cattcacaga   47160
acaattaata ttcaacaaaa gaaaccaccg cctcaagttc ttctgctctg aagaacaaaa    47220
aaagaaaaaa agaaccact acccagaatt cacatttgtc attcctgcat caaacatatt    47280
ttttttatta tttatttatt tattttgaa acagagtctt gctctgtcgc ccacactgag     47340
tgcagtgagc caagattgta ccactatgcc tggctaatct ttagtatttt tagtagagat    47400
ggggttttac catgttggcc aggctggtct caaactcccg acctcaagca atccacctgc    47460
cttggcctcc caaaatgcta ggattacagg tgtgagccac tgagcctggc ctaaataaat    47520
```

```
tttttttaatg aaacattgct taaaaaatta aaatttcact gttattcttt atcccattcc    47580
cctcccttct cttgataatg atcaatttga tgcctgtcca ctaagtctgt gttttataca    47640
ttcactgtaa atttatgaat ccataaacaa cacggacagt aggctgcata cctataagag    47700
gacttgctgg gcaacagaat agtaaacctt agagtaagtt tcaatatgta acaggaaaag    47760
ctctctttat cttttttcagt attgttttgg ctcttcctgg atgttaactt ttagaaccag    47820
tttgtctaat tcacaaaaag aatcctcttg ggattttgct tttcattgca ttggattgtt    47880
agactaattt gacttatttt cagtatgaat tcttcccaga taagaacatg atatatcact    47940
ccatttttag gtctctctta acatccttta ataatgcttt attgtttcct ccttaaagct    48000
gttgtatgtt tggctggctt ttttctgaag tgcttttataa gttttattgc tgttttttaaa    48060 ttacacctttt taaaatttttc ttttcttttt ttttgagatg gagtttcgct ctgtcaccca    48120
ggctggagtg cagtggtgcg atcttggctc actgtaagct ccgcctcccg ggttcatgcc    48180
attctcctgc ctcagcctcc ggagtagctg ggactacagg cgcctgccac cacgcccggc    48240
tatttttttt ttgtattttt agtagagaca aggtttcacc gtgttagcca ggatggtctc    48300
gatcttctga cctcgtgatc cgcccacctc ggcctcccaa agtgctggga ttacaggcgt    48360
gagccaccat gcccagccgt aacatttttat tttctatttg gttattgcta acatatgaaa    48420
caattactca tttttgtgtt ttgatcttat agccagccag caatactgct tttttgttct    48480
ttctgttttt gtttttttgtt ttttgggttt tttttgagac ggagtctcac tctgtcaccc    48540
agacgggagt gcagtggcac aatctcggct cactgcagtg tctgcctccc tggttcaaag    48600
gattcttctg ccttagcctc ctgagtatct ggcactacag gtgcgtgcca ccacacctgg    48660
ctaattttta tatttttact agagatgggg tttcgccatc ttggccaggc tggtctcgaa    48720
ctcctgacct cgtgatccac ccaccttggc ctcccaaagt gctgggatta caggctgtat    48780
tttgttttgt tatacagtac tattagtttt tcagtagatg ctcttggatt ttctatgtta    48840
ataatatcat atgcaaaaat cactaacttg tctcttcctt aaacctctttt ttcatttttct    48900 tacaaccatt ggaatggaat agtagcaatg atagtgggca tcctcatctt attcatgaca    48960
ttagtaaaaa tgcttttaaa atgtgatgtt tgctgtaaat tttaggtaga tgctctttat    49020
tacataaaag tttccttcta ttcctggttt tttgagctta taaaaaagta tgaatcagtg    49080 ttcagttttta tacactgctt ttttatgcac ctagaaatga ccctgtggct tttctccttt    49140
aatctgtcta tgtggtgaga ttatattgat agatttccaa tattgacctt ccttgtttta    49200
ctcagataaa attctactta gttacaatag atctcttttt ttggacatttt atgaactgaa    49260 ttttttaagag gaaaaatatt acacaatgat atgggagcat aattgagttc ctgctcttag    49320
aagataacaa atatttcaga gattttagta ggaatattgc cctgttaaga acgctcaatt    49380
ctctaaagct aagttcaaat aaggcccaat tcttggcctg agactctggt tcccacaagg    49440
gcaatacagg ctgaactggt ttgataactt ttaccattga gagtttttttt tttcttttttg    49500 agacggagtt ttgctcttat tgcccaggct ggagtgcaat ggcttgatct cggctcagtg    49560
caacctccgc ctcccagata caagtgattc tcctgtctca gcctccgaag tagctcagat    49620
tacaggcatg tgccaccaca cccagctaat tttttgtatt tagtagagac atgtttcatc    49680
atgttagtca ggctggtcgt gaactcctga cctcaggtga tccacccgcc tcagcctccc    49740
aaagtgctgg gattataggc gtgcgccact gcacccggcc acgtttaaga gttttaagga    49800
aggaccagga ataatagagg tcatcttttc gtggaacgaa gagtttataa tctcccagct    49860
gacctaaatc tgagatctgt gatcgtatct agtctgaaag ttacagagcc attcagctgg    49920
```

-continued

```
cagaagaaag gtagtgaagt tgaacagcat ccccactctt tggggtggaa aggttgctgg    49980
agtttccccc agattaagtg gttcctggag aagatggaag gagtataagc agttctgctg    50040
gtaactccta aaatggccac tacctgggta atagaaccct ggaagcaaaa gacatagaat    50100
atctattggt agaatgtgct ggactaggga gaaagaagtt gagcttcatt catataccccc   50160 tgctcaactt cctaccagga ccatgccacg agtctttctg gagaaatatc atttggacac    50220
ctgccagatg aagagaactg gtggtcaatt ggtaataatc agagaaactg ggacaaccaa    50280
cagaaaggga cagaaatgtt tcccatgatc tagttgaggt tgttcataca atgaaccaca    50340
gttatgtcct gctaataaaa gggcaactaa ttttgaaggg caattatgta aagaaatgta    50400
attttcctct ccttcctcct tgccaccca actggtatcg ggatggcagg agtcatgtgt     50460
ggttttctat ggctgtgtaa caaattacca taaatgtagt agcttaaagc aacacaaatt    50520
attagctcac agtccatata tcagaaatcc aggtaggctc acctggttcc tctgctccag    50580
gtgtcataaa gcctaaatca aggtgtgggc cagcttgggc tcttaaggat ctagggaaga    50640
acctgctttc tagcttattc aaattgtcag ccaaattcag ttccttgtgg ttgtaggacg    50700 gtagtccct ttttcttgct agcagtgagg accactctca gctcctgaag gcttcctgca     50760
ttccttgcta cacactcccc tccatcttca agccagcaac agggtgttga atcacccttg    50820
tgctttgaac ctgacttact ctcctgctat cagccagaaa aaaactctga cttcaaaggc    50880
tcatgtgatt tgatgaggcc aacccagatc atctcccttt tgccatgtaa tgtaacagaa    50940
tgatgggagt aatatctcct catattcaca ggttcctccc acgcttaaag gggaggggat    51000
catccatagg caaggtcact gggagtcatt cttggaatt                           51039
```

ISOLATED GENOMIC POLYNUCLEOTIDE FRAGMENTS FROM CHROMOSOME 12 THAT ENCODE HUMAN CARBOXYPEPTIDASE M

PRIORITY CLAIM

This application is a divisional application of application Ser. No. 12/795,909, filed Jun. 8, 2010, which is a divisional application of application Ser. No. 10/608,403, filed Jun. 27, 2003 and issued as U.S. Pat. No. 7,754,424 on Jun. 13, 2010 under 35 USC §120, the contents of which are incorporated herein by reference.

FIELD OF THE INVENTION

The invention is directed to isolated genomic polynucleotide fragments from the human chromosome 12q13-q15 region that particularly encode human carboxypeptidase M and human mouse double minute 2 homolog, vectors and hosts containing these fragments and fragments hybridizing to noncoding regions as well as their reverse complements t. The invention is further directed to methods of using these fragments to obtain human carboxypeptidase M and human mouse double minute 2 homolog and to diagnose, treat, prevent and/or ameliorate a pathological disorder.

BACKGROUND OF THE INVENTION

Chromosome 12q13-q15 contains genes encoding, for example, interleukin 22, a protein tyrosine phosphatase, interferon-gamma, carboxypeptidase M and the human mouse double minute 2 homolog; the last two of which are discussed in more detail below. The chromosome 12q13-q15 region is known to be aberrant in tumors such as sarcomas (Oliner et al., Nature 358: 80-3, 1992).
Human Carboxypeptidase M Human carboxypeptidase M is a cell membrane-bound basic carboxypeptidase believed to act by activating, inactivating and modulating excitatory peptides such as the anaphylatoxins and kinins (Tan et al., J. Biol. Chem. 264: 13165-70. 1989). Its expression is increased as monocytes differentiate into macrophages (Rehli et al., J. Biol. Chem. 270: 15644-9, 1995). It is also widely distributed as an ectoenzyme of specialized epithelia and endothelia. Its ability to convert anaphylatoxins to their less active C-terminal des-Arg forms protects against complement-linked tissue damage.
Human Mouse Double Minute 2 Homolog Human mouse double minute 2 homolog plays a key role in modulating actions of p53 (Oliner et al., supra), in part by targeting p53 for destruction (Ries et al., Cell 103: 321-30, 2000). Over-expression of this oncogene increases tumorigenic potential. The human mouse double minute 2 homolog is over-expressed in both sarcomas and some leukemias. In addition to its ability to in effect neutralize p53, it reacts also with a retinoblastoma protein.

SUMMARY OF THE INVENTION

The invention is directed to isolated genomic polynucleotides, said polynucleotides obtainable from the human chromosome 12q13-q15 region having a nucleotide sequence at least 95% identical to a sequence selected from the group consisting of:

(a) a genomic polynucleotide encoding a polypeptide selected from the group consisting of human carboxypeptidase M depicted in SEQ ID NO:1 or human mouse double minute 2 homolog depicted in SEQ ID NO:2, or variants of SEQ ID NOS:1 or 2;

(b) a genomic polynucleotide selected from the group consisting of SEQ ID NO:3 which encodes human carboxypeptidase M depicted in SEQ ID NO:1 and SEQ ID NO:4 which encodes human mouse double minute 2 homolog depicted in SEQ ID NO:2, or variants of SEQ ID NOS: 3 or 4, (c) a polynucleotide which hybridizes to any one of the polynucleotides specified in (a)-(b) and (d) a polynucleotide that is a reverse complement to the polynucleotides specified in (a) to (c)
as well as nucleic acid constructs, expression vectors and host cells containing these polynucleotide sequences.

The invention further relates to a polynucleotide comprising:

(a) a genomic double stranded polynucleotide set forth in SEQ ID NO:3 encoding human carboxypeptidase M set forth in SEQ ID NO:1 and the polynucleotide set forth in SEQ ID NO:4 encoding human mouse double minute 2 homolog set forth in SEQ ID NO:2;

(b) a polynucleotide that hybridizes to one strand of the polynucleotide of (a) and (c) a reverse complement of (a) and (b).
as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (a) with an adjuvant and (c) obtaining antibody from said immunized host animal.

The invention is further directed to a nucleic acid molecule or reverse complement thereof comprising a sequence of nucleotides which specifically hybridizes to noncoding regions of said polynucleotide sequences of SEQ ID NO:3 (human carboxypeptidase M gene) or SEQ ID NO:4 (human mouse double minute 2 homolog gene). These sequences may be used to modulate levels of human carboxypeptidase M and human mouse double minute 2 homolog in a subject in need thereof and specifically for the manufacture of a medicament for prevention, treatment or amelioration of a medical condition. As defined herein, a "polynucleotide fragment" may be a nucleic acid molecule including DNA, RNA and analogs thereof including protein nucleic acids and mixtures thereof and may include a probe and primer. Such molecules are generally of a length such that they are statistically unique in the genome of interest. Generally, for a probe or primer to be unique in the human genome, it contains at least 14 to 16 contiguous nucleotides of a sequence complementary to or identical to a target sequence of interest. These polynucleotide fragments can be 20, 30, 50, 100, 150, 500, 600, 1000, 2000 or more nucleic acids long. Probes and primers may also be referred to as oligonucleotides. As defined herein, a "reverse complement" is a molecule encoding a sequence complementary to at least a portion of an RNA molecule or to a genomic DNA segment and may be used interchangeably with "antisense oligonucleotide". The sequence is sufficiently complementary to be able to hybridize with the RNA or DNA, preferably under moderate or high stringency conditions to form a stable duplex or triplex. A "reverse complement" also includes peptide nucleic acid reverse complement sequences.

The invention is further directed to kits comprising these polynucleotides and kits comprising these sequences. In a specific embodiment, the sequence(s) are attached to a substrate. In a specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to detect a pathological condition or susceptibility to a pathological condition in a subject comprising (a) isolating genomic DNA from said subject;

(b) detecting the presence or absence of a variant in said genomic DNA using a probe or primer derived from a polynucleotide hybridizing to non-coding region(s) of a human carboxypeptidase M gene and human mouse double minute 2 homolog gene; and (c) diagnosing a pathological condition or susceptibility to a pathological condition based on the presence or absence of said variant.

Probes or primers derived from SEQ ID NO:3 (human carboxypeptidase M gene) or SEQ ID NO: 4 (human mouse double minute 2 homolog gene) may be used to identify variants including but not limited to mutations, duplications, translocations, polysomies and mosaicism on the human carboxypeptidase M gene or on the human mouse double minute 2 homolog. Therefore, the invention is also directed to a method for identifying variants of SEQ ID NO:3 and 4 comprising (a) isolating genomic DNA from a subject and (b) determining the presence or absence of a variant in said genomic DNA using the probes or primers.

DETAILED DESCRIPTION OF THE INVENTION

The invention is directed to isolated genomic polynucleotide fragments that encode human carboxypeptidase M and human mouse double minute 2 homolog, which in a specific embodiment are the human carboxypeptidase M and human mouse double minute 2 homolog genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The genes encoding human carboxypeptidase M and the human mouse double minute 2 homolog are disposed in the chromosome 12 genomic clone of accession number AC025423, 150579 base pairs, at, respectively, nucleotides 1-99860 and 99541-150579.

The polynucleotides of the invention have at least a 95% identity and may have a 96%, 97%, 98% or 99% identity to the polynucleotides depicted in SEQ ID NOS:3 or 4 as well as the polynucleotides in reverse sense orientation, or the polynucleotide sequences encoding the human carboxypeptidase M or human mouse double minute 2 homolog polypeptides depicted in SEQ ID NOS:1 or 2 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 3 or 4. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The term "variant" also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. The term "variant" also encompasses naturally occurring variants such as single nucleotide polymorphisms (SNPs).

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human carboxypeptidase M or human mouse double minute 2 homolog genes. These include but are not limited to an expression control element, an intron, a 5'-non-coding region, a 3'-non-coding region and splice junctions (see Tables 1-2, as well as transcription factor binding sites (see Table 3). The polynucleotide fragments may be a short polynucleotide fragment which is between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600, 2000 or about 5000 nucleotides in length may be used.

TABLE 1

EXON/INTRON ORGANIZATION OF THE HUMAN CARBOXY-PEPTIDASE M GENE (cDNA ACCESSION NO. XM_006768) IN SEQ ID NO: 3, 99680 BASE PAIRS; NUCLEOTIDES 1-99680 IN THE GENOMIC CLONE OF ACCESSION NO. AC025423 (FORWARD STRAND CODING).

| EXON | NUCLEOTIDE NO. | AMINO ACID NO. |
|---|---|---|
| 1 | 16641-16796 | 1-52 |
| 2 | 63585-63686 | 53-86 |
| 3 | 77522-77692 | 87-143 |
| 4 | 79077-79262 | 144-205 |
| 5 | 79982-80152 | 206-262 |
| 6 | 82429-82581 | 263-313 |
| 7 | 90406-90555 | 314-363 |

TABLE 1-continued

EXON/INTRON ORGANIZATION OF THE HUMAN CARBOXY-PEPTIDASE M GENE (cDNA ACCESSION NO. XM_006768) IN SEQ ID NO: 3, 99680 BASE PAIRS; NUCLEOTIDES 1-99680 IN THE GENOMIC CLONE OF ACCESSION NO. AC025423 (FORWARD STRAND CODING).

| EXON | NUCLEOTIDE NO. | AMINO ACID NO. |
|---|---|---|
| 8 | 92799-93038 | 364-443 |
| STOP CODON | 93039-93041 | |

TABLE 2

EXON/INTRON ORGANIZATION OF THE HUMAN MOUSE DOUBLE MINUTE 2 HOMOLOG GENE (VARIANT OF ACCESSION NO. NM_002392) IN SEQ ID NO: 4, 51039 BASE PAIRS; NUCLEOTIDES 99541-150579 IN THE GENOMIC CLONE OF ACCESSION NO. AC025423 (REVERSE STRAND CODING).

| EXON | NUCLEOTIDE NO. | AMINO ACID NO. |
|---|---|---|
| STOP CODON | 10089-10091 | |
| 10 | 10092-10664 | 491-301 |
| 9 | 13189-13266 | 300-275 |
| 8 | 13954-14109 | 274-223 |
| 7 | 21007-21168 | 222-169 |
| 6 | 25288-25383 | 168-137 |
| 5 | 25508-25576 | 136-114 |
| 4 | 29565-29615 | 113-97 |
| 3 | 32995-33126 | 96-53 |
| 2 | 36310-36384 | 52-28 |
| 1 | 40646-40726 | 27-1 |

TABLE 3

TRANSCRIPTION FACTOR BINDING SITES ON GENES THAT ENCODE CARBOXYPEPTIDASE M (CpM) AND THE HUMAN HOMOLOG OF MOUSE DOUBLE MINUTE 2 (huMDM2)

| BINDING SITES | CpM | huMDM2 |
|---|---|---|
| AP1FJ_Q2 | 60 | 25 |
| AP1_C | 16 | 11 |
| AP1_Q2 | 39 | 13 |
| AP1_Q4 | 24 | 12 |
| AP4_Q5 | 47 | 27 |
| AP4_Q6 | 22 | 14 |
| ARNT_01 | | 4 |
| BRN2_01 | 29 | 6 |
| CAAT_01 | 7 | 4 |
| CDPCR3HD_01 | 19 | 7 |
| CEBPB_01 | 26 | 6 |
| CMYB_01 | 7 | |
| CREL_01 | 15 | 4 |
| DELTAEF1_01 | 196 | 98 |
| FREAC7_01 | 30 | 29 |
| GATA1_02 | 40 | 25 |
| GATA1_03 | 63 | 21 |
| GATA1_04 | 109 | 46 |
| GATA1_05 | 21 | 13 |
| GATA1_06 | 33 | 26 |
| GATA2_02 | 59 | 35 |
| GATA2_03 | 20 | 19 |
| GATA3_02 | 30 | 23 |
| GATA3_03 | 18 | 20 |
| GATA_C | 61 | 15 |
| GFII_01 | 23 | 8 |
| HFH2_01 | 20 | 13 |
| HFH3_01 | 32 | 13 |
| HFH8_01 | 23 | 7 |
| HNF3B_01 | 10 | 7 |
| IK1_01 | 12 | |
| IK2_01 | 216 | 63 |

TABLE 3-continued

TRANSCRIPTION FACTOR BINDING SITES ON GENES
THAT ENCODE CARBOXYPEPTIDASE M (CpM) AND
THE HUMAN HOMOLOG OF MOUSE
DOUBLE MINUTE 2 (huMDM2)

| BINDING SITES | CpM | huMDM2 |
| --- | --- | --- |
| LMO2COM_01 | 86 | 23 |
| LMO2COM_02 | 85 | 23 |
| LYF1_01 | 45 | 41 |
| MAX_01 | 8 | 4 |
| MYCMAX_02 | 8 | |
| MYOD_01 | 5 | |
| MYOD_Q6 | 49 | 21 |
| MZF1_01 | 187 | 61 |
| NF1_Q6 | 10 | 5 |
| NFAT_Q6 | 134 | 71 |
| NFY_Q6 | 16 | |
| NKX25_01 | 48 | 35 |
| NKX25_02 | 30 | 9 |
| NMYC_01 | 16 | 10 |
| OCT1_01 | 3 | |
| OCT1_02 | 6 | |
| OCT1_06 | 3 | |
| OCT1_07 | 5 | |
| OCT1_Q6 | 5 | |
| RORA1_01 | 8 | 9 |
| S8_01 | 183 | 128 |
| SOX5_01 | 76 | 29 |
| SRY_02 | 38 | 27 |
| STAT_01 | 11 | |
| TATA_01 | 28 | 22 |
| TATA_C | 20 | 8 |
| TCF11_01 | 182 | 51 |
| USF_01 | 16 | 10 |
| USF_C | 16 | 10 |
| VMYB_02 | 7 | 11 |
| XFD2_01 | 11 | 8 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979);

Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 12 genomic clone of accession number AC025423 has been discovered to contain the human carboxypeptidase M gene and the human mouse double minute 2 homolog gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC025423 was compared to the human carboxypeptidase M cDNA sequence, accession number XM_006768 and the human mouse double minute 2 homolog cDNA sequence accession number NM_002392, one of several splice variants.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human carboxypeptidase M gene or the human mouse double minute 2 homolog gene may be accomplished in a number of ways. For example, if an amount of a portion of a human carboxypeptidase M gene or the human mouse double minute 2 homolog gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 15 and preferably 40, nucleotide fragment of the sequences depicted in SEQ ID NOS:3 or 4. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human carboxypeptidase M or human mouse double minute 2 homolog polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:3 or 4 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human carboxypeptidase M or human mouse double minute 2 homolog polypeptide.

A gene encoding human carboxypeptidase M or human mouse double minute 2 homolog polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human carboxypeptidase M gene (nucleotides 1-99680 of SEQ ID NO:3) or human mouse double minute 2 homolog gene (nucleotides 1-51039 of SEQ ID NO:4) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 3 or 4 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention. Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Preferred terminators for yeast host cells are obtained from the genes encoding *Saccharomyces cerevisiae* enolase, *Saccharomyces cerevisiae* cytochrome C(CYC1), or *Saccharomyces*

*cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention. Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention. Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase. Useful polyadenylation sequences for yeast host cells are described by Guo and Sherman, 1995, *Molecular Cellular Biology* 15: 5983-5990. The control sequence may also be a signal peptide coding region, which codes for an amino acid sequence linked to the amino terminus of the polypeptide which can direct the encoded polypeptide into the cell's secretory pathway.

The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention. An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109-137. An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene. Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-50-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell. For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM§1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, carboxypeptidase M activity can be determined by measuring the release of the C-terminal arginine of bradykinin or a synthetic acyl-dipeptide such as benzoyl-Ala-Arg. The human homolog of mouse double minute 2 may be detected by its ability to bind p53.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Antibodies

According to the invention, the human carboxypeptidase M or human mouse double minute 2 homolog polypeptides produced according to the method of the present invention may be used as an immunogen to generate any of these antibodies. Such antibodies include but are not limited to polyclonal, monoclonal, chimeric, single chain, Fab fragments, and a Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum.

For preparation of monoclonal antibodies directed toward the human carboxypeptidase M or human mouse double minute 2 homolog polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human carboxypeptidase M or human mouse double minute 2 homolog polypeptide together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human carboxypeptidase M or human mouse double minute 2 homolog polypeptide.

Antibody fragments that contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451, 570; 4,466,917; 4,472,500; 4,491,632; 4,493,890.

Substrate

In a specific embodiment, the polynucleotides of the present invention, particularly, the polynucleotide fragments for hybridizing to non-coding regions of SEQ ID NOS:3 or 4 may be attached to a substrate or reverse complements of said fragments. A substrate may be solid or porous, planar or non-planar, unitary or distributed. The polynucleotide may be attached covalently or applied to a derivatized surface in a chaotropic agent that facilitates denaturation and adherence by presumed noncovalent interactions, or some combinations thereof.

In a more specific embodiment, the substrate is a microarray. "Microarray" as defined herein is a substrate-bound collection of a plurality nucleic acids, hybridization to each of the plurality of bound nucleic acids being separately detectable. The microarray may comprise a plurality of polynucleotides hybridizing to a non coding region of SEQ ID NO:3 or 4. Alternatively the microarray may comprise a polynucleotide(s) hybridizing to said non-coding region and/or coding regions of SEQ ID NO:3 or 4.

Uses of Polynucleotides

Diagnostics

Polynucleotide fragments containing noncoding regions of SEQ ID NO:3 or 4 may be used as probes for detecting variants from genomic nucleotide samples from a patient. The variants may be allelic variants or substitution, insertion or deletion nucleotide variants. Genomic DNA may be isolated from the patient. Alternatively the polynucleotide fragments may be used to monitor expression of SEQ ID NO:3 or 4 from samples from a patient. A mutation(s) may be detected by Southern blot analysis, for example, by hybridizing restriction digested genomic DNA to various probes between 10-500 nucleotides in length, preferably between 20-200 nucleotides in length, more preferably between 20-100 nucleotides in length and most preferably between 20-50 nucleotides in length and subjecting to agarose electrophoresis. Alternatively, these polynucleotides may be used as PCR primers between about 10-100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998)). Single base extension (see, for example, U.S. Pat. No. 6,004,744) may be used to detect SNPs. Additionally, primers may be obtained by routine or long range PCR that yield products containing contiguous intron(s)/exon sequence(s) and products containing more than one exon with intervening intron(s). The sequence of the amplified genomic DNA from the patient may be determined using methods known in the art. Such probes may be between 20-5000 nucleotides in length and may preferably be between 20-50 nucleotides in length.

Thus the invention is directed to kits comprising these polynucleotide probes. In a specific embodiment, these probes are labeled with a detectable substance.

In one embodiment, the probes are in solution. In another embodiment, the probes are attached to a substrate. In a specific embodiment, the probes are contained within a microarray and are separately detectable. The probes or primers of the present invention could be used to identify patients with or having a propensity for sepsis (SEQ ID NO:3-carboxypeptidase M gene) or for sarcoma or leukemias (SEQ ID NO:4-human mouse double minute 2 homolog gene).

Antisense Oligonucleotides and Mimetics

The antisense or reverse complement oligonucleotides or mimetics of the present invention may be used to decrease levels of a polypeptide. For example, human carboxypeptidase M has been found to form des-Arg9-bradykinin, an agonist of the B1 receptor activated by sepsis. Therefore, the human carboxypeptidase M antisense oligonucleotides of the present invention could be used to inhibit formation of des-Arg9-bradykinin Human mouse double minute 2 homolog antisense sequences may be used to treat sarcomas and leukemias in which the gene is over-expressed.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to
several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50 as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human carboxypeptidase M modulates actions of anaphylatoxins and kinins and human mouse double minute 2 homolog plays a role in cell proliferation. Therefore, the human carboxypeptidase M gene may be used to modulate or prevent complement-linked tissue damage, in subjects in need thereof, for example, those exhibiting allergic reactions to a given substance. The human mouse double minute 2 homolog gene may be used to stimulate cell proliferation in subjects in need thereof, for example, for wound healing and those suffering from neurodegenerative or neuromuscular diseases, ischemic stroke, anoxia, ischemia/reperfusion damage and intoxication septic shock.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science*, 247, 1465-1468, 1990; and Wolff, Jon A, "Human dystrophin expression in mdx mice after intramuscular injection of DNA constructs," *Nature*, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes: a) Biological agents derived from viral, bacterial or other sources and b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in nonproliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^4$-spermine cholesteryl carbamate (GL-67) disclosed in U.S. Pat. No. 5,767,099. Additional preferred lipids include N4_spermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class 1 molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method of identifying a nucleotide sequence variant of a 5'-noncoding region, 3'-noncoding region or intron region of SEQ ID NO:3 or its full complementary sequence comprising
   (a) isolating genomic nucleic acid from a sample and
   (b) determining the presence or absence of a nucleotide sequence variation in said genomic nucleic acid by comparing the nucleotide sequence of SEQ ID NO:3 with the nucleotide sequence of the isolated genomic nucleic acid and establishing if and where a difference occurs between the two nucleic acid sequences thereby identifying a nucleotide sequence variant of SEQ ID NO:3 or its full complement.

2. The method according to claim 1, wherein said variant encodes a protein having human Carboxypeptidase M activity.

3. A method of identifying variants of SEQ ID NO:3 comprising
   (a) isolating genomic nucleic acid from a subject and
   (b) determining the presence or absence of a variant in said genomic DNA using an isolated nucleic acid molecule consisting of a fragment of a non-coding region of SEQ ID NO:3, wherein said non-coding region is selected from the group consisting of a 5'-noncoding region shown in sequence segment 1-16440 of SEQ ID NO:3, a 3'-non coding region shown in sequence segment 93042-99680 of SEQ ID NO:3 and an intron region shown in sequence segments, 16797-63584, 63687-77521, 77693-79076, 79263-79981, 80153-82428, 82582-90405, 90556-92798 of SEQ ID NO:3, noncoding fragment is at least 20 contiguous nucleotides in length or a full complement of said isolated nucleic acid molecule.

4. A method of identifying variants of SEQ ID NO:3 comprising (a) isolating genomic DNA nucleic acid from a subject and (b) determining the presence or absence of a variant in said genomic nucleic acid using an isolated nucleic acid molecule consisting of a sequence segment of SEQ ID NO:3, wherein said segment is at least 20 contiguous nucleotides in length consisting of a contiguous coding and non-coding nucleic acid sequence of SEQ ID NO:3.

5. The method according to claim 4, wherein said genomic nucleic acid is amplified.

* * * * *